US012716095B2

(12) United States Patent
Zheng et al.

(10) Patent No.: US 12,716,095 B2
(45) Date of Patent: Aug. 25, 2026

(54) METHODS AND SYSTEMS FOR MEASURING MULTIPLEX RNA EXPRESSION

(71) Applicant: City University of Hong Kong, Kowloon (HK)

(72) Inventors: Zongli Zheng, Kowloon (HK); Chenyu Lu, Kowloon (HK)

(73) Assignee: City University of Hong Kong, Kowloon (HK)

( * ) Notice: Subject to any disclaimer, the term of this patent is extended or adjusted under 35 U.S.C. 154(b) by 687 days.

(21) Appl. No.: 18/245,599

(22) PCT Filed: Jan. 28, 2023

(86) PCT No.: PCT/CN2023/073581
§ 371 (c)(1),
(2) Date: Mar. 16, 2023

(87) PCT Pub. No.: WO2023/143521
PCT Pub. Date: Aug. 3, 2023

(65) Prior Publication Data

US 2024/0318242 A1 Sep. 26, 2024

Related U.S. Application Data

(60) Provisional application No. 63/304,489, filed on Jan. 28, 2022.

(51) Int. Cl.
*C12Q 1/6869* (2018.01)
*C12Q 1/6806* (2018.01)
*C12Q 1/686* (2018.01)

(52) U.S. Cl.
CPC ......... *C12Q 1/6869* (2013.01); *C12Q 1/6806* (2013.01); *C12Q 1/686* (2013.01); *G01N 2800/52* (2013.01)

(58) Field of Classification Search
None
See application file for complete search history.

(56) References Cited

U.S. PATENT DOCUMENTS

2004/0023207 A1* 2/2004 Polansky ............. A61K 48/005 435/456
2023/0332213 A1* 10/2023 Henikoff ............ C12N 15/1082

OTHER PUBLICATIONS

Song et al. Simultaneous Detection of Gene Fusions and Base Mutations in Cancer Tissue Biopsies by Sequencing Dual Nucleic Acid Templates in Unified Reaction. Clinical Chemistry 66(1):178-187 (2020). (Year: 2020).*
Song Supplementary Data Table 2 [online] Dec. 30, 2019 [retrieved on Nov. 15, 2025] retrieved from https://academic.oup.com/clinchem/article/66/1/178/5688840 (Year: 2019).*
Song et al. Abstract, Proceedings of the Annual Meeting of the American Association for Cancer Research 2020; Apr. 27-28, 2020 and Jun 22-24. Philadelphia (PA): AACR; Cancer Res 2020;80(16 Suppl): Abstract nr 6490. (Year: 2020).*
L. Gandhi, et al., Pembrolizumab plus Chemotherapy in Metastatic Non-Small-Cell Lung Cancer, N Engl J Med 2018; 378:2078-92.
Anne C. Chiang and Roy S. Herbst, Frontline immunotherapy for NSCLC—the tale of the tail, Nature Reviews, vol. 17 (Feb. 2020), 73-74.
Edward B. Garon, et al., Pembrolizumab for the Treatment of Non-Small-Cell Lung Cancer, N Engl J Med 2015; 372:2018-28.
Scott N. Gettinger, et al., First-line nivolumab (anti-PD-1; BMS-936558, ONO-4538) monotherapy in advanced NSCLC: Safety, efficacy, and correlation of outcomes with PD-L1 status, Journal of Clinical ONcology 32, No. 15 (May 20, 2014) 8024-8024.
Tony S K Mok, et al., Pembrolizumab versus chemotherapy for previously untreated, PD-L1-expressing, locally advanced or metastatic non-small-cell lung cancer (Keynote-042): a randomised, open-label, controlled, phase 3 trial, Lancet 2019: 393:1819-30.
Svetlana Kintsler, et al., Expression of prgrammed death ligand (PD-L1) in different tumors. Comparison of several current available antibody clones and antibody profiling, Annals of Diagnostic Pathology 41 (2019) 24-37.
Fred R. Hirsch, et al., PD-L1 Immunohistochemistry Assays for Lung Cancer: Results from Phase 1 of the Blueprint PD-L1 IHC Assay Comparison Project, Journal of Thoracic Oncology, vol. 12 No. 2: 208-222, (2017).
Nicola L. Lawson, et al., Mapping the binding sites of antibodies utilized in programmed cell death ligand-1 predictive immunohistochemical assays for use with immuno-oncology therapies, Modern Pathology (2020) 33:518-530.
Y Jiang, et al., T-Cell exhaustion in the tumor microenvironment, Cell Death and Disease (2015) 6, e1792.
Dachuan Zhang, et al., Scoring System for Tumor-Infiltrating Lymphocytes and Its Prognostic Value for Gastric Cancer, Front. Immunol. 10:71, (2019).
Takaaki Tokito, et al., Predictive relevance of PD-L1 expression combined with CD8+ TIL density in stage III non-small cell lung cancer patients receiving concurrent chemoradiotherapy, European Journal of Cancer, 55 (2016) 7-14.
Jean-David Fumet, et al., Prognostic and predictive role of CD8 and PD-L1 determination in lung tumor tissue of patients under anti-PD-1 therapy, British Journal of Cancer (2018) 119:950-960.
Christian U. Blank, et al., Defining 'T cell exhaustion', Nature Reviews, vol. 19, Nov. 2019, 665-674.

(Continued)

*Primary Examiner* — Samuel C Woolwine
(74) *Attorney, Agent, or Firm* — Renner, Kenner, Greive, Bobak, Taylor & Weber

(57) ABSTRACT

A method of measuring RNA expression level of a target sequence in a sample is performed by simultaneously enriching the target sequence and corresponding RNA and calculating a RNA-to-DNA ratio of the same target sequence. A method of treating cancer includes the step of using the method of measuring RNA expression level of a target sequence. A kit includes components for performing the method of measuring RNA expression level of a target sequence.

17 Claims, 17 Drawing Sheets

Specification includes a Sequence Listing.

(56) References Cited

OTHER PUBLICATIONS

Peng Jiang, et al., Signatures of T cell dysfunction and exclusion predict cancer immunotherapy response, Nature Medicine vol. 24 Oct. 2018, 1550-1558.
Keisuke Kataoka, et al., Aberrant PD-L1 expression through 3'-UTR disruption in multiple cancers, Nature (2016) vol. 534, 402-406.
Bo Gong, et al., Secreted PD-L1 variants mediate resistance to PD-L1 blockade therapy in non-small cell lung cancer, J. Exp. Med. 2019 vol. 216 No. 4, 982-1000.
Angelo Castello, et al., Soluble PD-L1 in NSCLC Patients Treated with Checkpoint Inhibitors and Its Correlation with Metabolic Parameters, Cancers 2020, 12, 1373.
Manuela Tiako Meyo, et al., Predictive Value of Soluble PD-1, PD-L1, VEGFA, CD40 Ligand and CD44 for Nivolumab Therapy in Advanced Non-Small Cell Lung Cancer: A Case-Control Study, Cancers 2020, 12, 473.
Zongli Zheng, et al., Anchored multiplex PCR for targeted next-generation sequencing, Nat. Med. (2014), 20(12):1479-1484.
Russell W Jenkins, et al., Mechanisms of resistance to immune checkpoint inhibitors, British J of Cancer (2018) 118, 9-16.
Jesse M. Zaretsky, et al., Mutations Associated with Acquired Resistance to PD-1 Blockade in Melanoma, N Engl J Med 2016; 375:819-829.
Daniela S. Thommen, et al., Progression of Lung Cancer is Associated with Increased Dysfunction of T Cells Defined by Coexpression of Multiple Inhibitory Receptors, Cancer Immunol Res, 3(12) Dec. 2015, 1344-1355.
J. Nicholas Bodor, et al., Biomarkers for Immune Checkpoint Inhibition in Non-Small Cell Lung Cancer (NSCLC), Cancer (2019) Jan. 15, 2020, 260.

* cited by examiner

METHODS AND SYSTEMS FOR MEASURING MULTIPLEX RNA EXPRESSION

SEQUENCE LISTING

The Sequence Listing file entitled "sequencelisting" having a size of 690,874 bytes and a creation date of Mar. 15, 2023, that was filed with the patent application is incorporated herein by reference in its entirety.

FIELD OF THE INVENTION

The present invention relates to next-generation sequencing. More specifically, the present invention relates to methods and systems for measuring multiplex RNA expression.

BACKGROUND

Clinics widely use next-generation Sequencing (NGS) technology for many molecular diagnosis assays but not RNA expression. However, there are currently no reliable methods for multiplexing RNA quantification using NGS.

Currently-available RNA expression by RNA sequencing suffers from i) low efficiency in quantifying clinically relevant genes; ii) low accuracy in measuring low-level but clinically important genes, such as ALK—the most successful target in precision medicine; iii) high cost, as it allows only whole genome analysis and the vast majority of which are not clinically relevant; iv) not applicable to the most accessible clinical samples such as FFPE tumor tissues. Other non-NGS methods in RNA expression analyses generally associated with low multiplexing ability (e.g. RT-qPCR or digital PCR) and additional sample and workflow are needed (e.g. RNA-Scope and NanoString), in addition to the main stream NGS workflow.

Revolutionary cancer immunotherapy using immune checkpoint inhibitors (ICIs) may bring long-lasting responses in multiple cancers. However, current diagnosis methods, to find the about 20-30% of cancer patients who could benefit from ICI therapies, are suboptimal.

Researchers spend great effort to identify predictive markers for ICIs, including PD-L1 expression, tumor-infiltrating lymphocytes (TIL), especially the $CD^{8+}$ T cells[5]. Higher ORR was correlated with high expression of PD-L1, ORR for PD-L1 tumour proportion score (TPS) of 1% or greater patients and TPS 50% or greater patients was 27% and 39%, respectively[6]. Currently, four PD-L1 IHC assay[7,8] (22C3, 28-8, SP142, and SP263) was approved by FDA as companion or complementary diagnostic assay for different ICIs (pembrolizumab, nivolumab, atezolizumab and durvalumab, respectively) in NSCLC. However, the cutoffs determining high PD-L1 expression vary among different studies[7] (1%, 5%, 10%, or 50% PD-L1 positive cells). Also, the current IHC assays recognize different epitopes of PD-L1. Ventana SP142 and SP263 target the cytoplasmic domain of PD-L1, while 22C3 and 28-8 clones are raised against epitopes within the extracellular domain[9], which might explain the dis-concordance between the SP142/SP263 and 22C3/28-8[8]. Thus, this semi-quantified method for ICI response prediction is imperfect, highlighting the necessity in developing more precise method for PD-L1 quantification.

In view of the above, there remains a need to develop new method for detecting RNA expressions precisely and quickly. Also, there is a need of identifying predictive markers for ICIs, which would be critical for precision medicine.

SUMMARY OF THE INVENTION

An embodiment of the present invention relates to method of measuring RNA expression level of a target sequence in a sample by simultaneously enriching the target sequence and corresponding RNA and calculating a RNA-to-DNA ratio of the same target sequence, including the steps of (a) reverse transcribing RNA into complementary DNA (cDNA) resulting in a mixture of cDNA and genomic DNA (gDNA);

(b) ligating a universal sequencing adaptor to a terminal of the gDNA and cDNA from step (a);

(c) conducting a first polymerase chain reaction process to produce a single-stranded primer extension product including a complementary sequence, wherein the complementary sequence is complementary to the target sequence on the gDNA, the cDNA, or a combination thereof, and is complementary to the universal sequencing adaptor;

(d) conducting a second polymerase chain reaction process to amplify the single-stranded primer extension product; and (e) performing a next-generation sequencing process and calculating the relative ratio of cDNA sequencing reads to gDNA sequencing reads, namely the RNA-to-DNA ratio, of the same target sequence, wherein the target sequence is selected from a group of a gene sequence, an exon of a gene, and a combination thereof.

An embodiment of the present invention relates to a method of treating cancer in a subject containing the steps of testing for RNA expression level of a target sequence by using the method of measuring RNA expression level as provided herein, and applying an immune checkpoint inhibitor to the subject.

Another embodiment of the present invention relates to a kit for performing the method of measuring RNA expression level of a target sequence in a sample by simultaneously enriching a target DNA and corresponding RNA and calculating a RNA-to-DNA ratio of the same target sequence as described herein, the kit includes:

(a) a reverse transcriptase for transcribing RNA into complementary DNA (cDNA);

(b) a universal sequencing adaptor to be ligated to a terminal of gDNA and cDNA in the sample;

(c) a first primer that binds to the cDNA and gDNA sequence at a position that is 3' in relation to the target sequence on the cDNA or gDNA; and (d) a second primer that binds to the target sequence at a position that is between the first primer and the target sequence on the cDNA or gDNA.

Figure 1A:
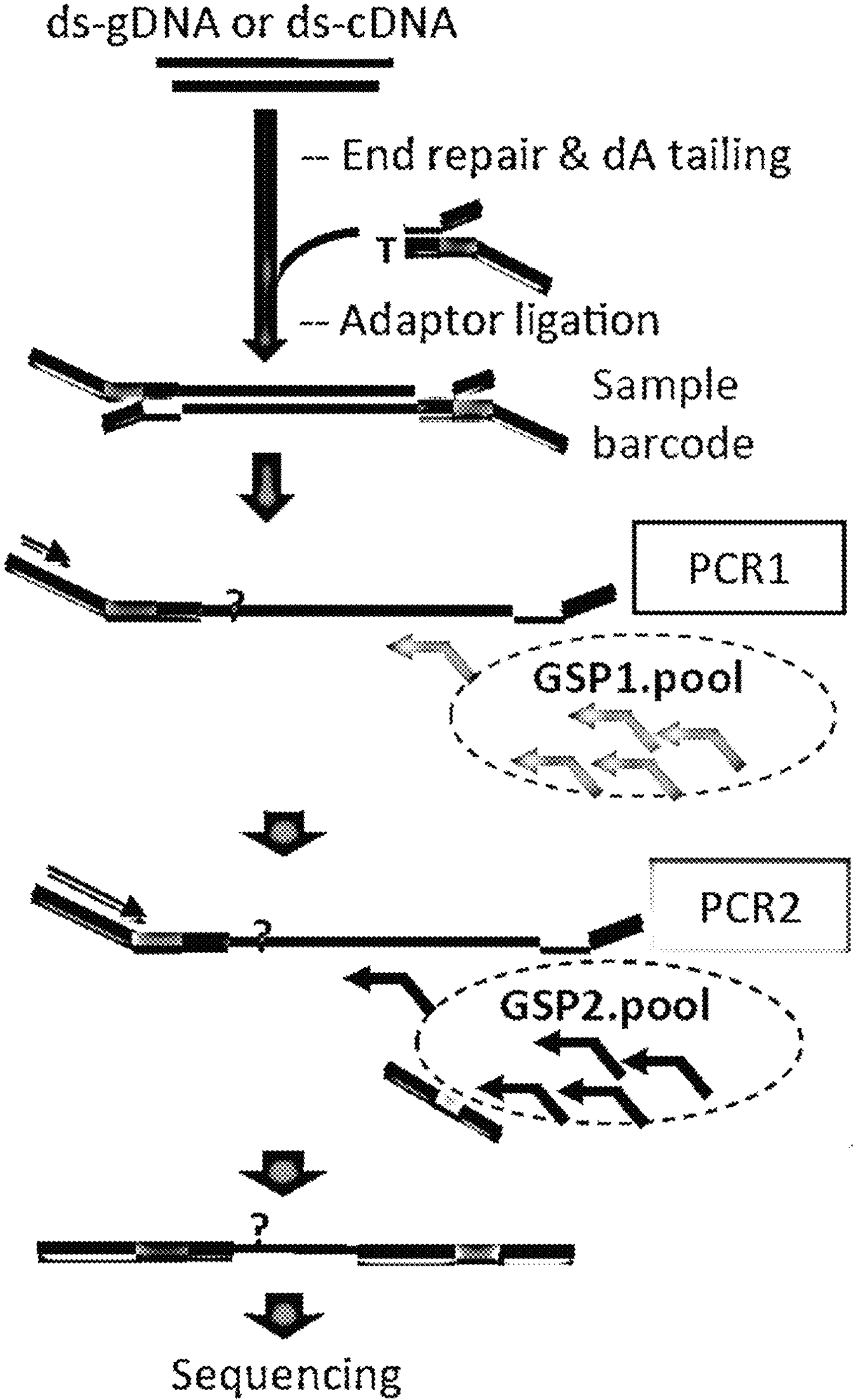
FIG. 1*a* shows a schematic description of the anchored multiplex PCR.

The figures herein are for illustrative purposes only and are not necessarily drawn to scale.

DESCRIPTION OF THE PREFERRED EMBODIMENTS

Unless otherwise specifically provided, all tests herein are conducted at standard conditions which include a room and testing temperature of 25° C., sea level (1 atm.) pressure, pH 7, and all measurements are made in metric units. Furthermore, all percentages, ratios, etc. herein are by weight, unless specifically indicated otherwise. It is understood that unless otherwise specifically noted, the materials compounds, chemicals, etc. described herein are typically commodity items and/or industry-standard items available from a variety of suppliers worldwide.

As used herein, overall survival (OS) is defined as the period from surgery of a patient to the date of the last follow-up or death of the patient.

An embodiment of the present invention relates to a method of measuring RNA expression level of a target sequence in a sample by simultaneously enriching a target DNA and corresponding RNA and calculating a RNA-to-DNA ratio of the same target sequence, including the steps of (a) reverse transcribing RNA into complementary DNA (cDNA) resulting in a mixture of cDNA and genomic DNA (gDNA);

(b) ligating a universal sequencing adaptor to a terminal of the gDNA and cDNA from step (a);

(c) conducting a first polymerase chain reaction process to produce a single-stranded primer extension product including a complementary sequence, wherein the complementary sequence is complementary to the target sequence on the gDNA, the cDNA, or a combination thereof, and is complementary to the universal sequencing adaptor;

(d) conducting a second polymerase chain reaction process to amplify the single-stranded primer extension product; and (e) performing a next-generation sequencing process and calculating the relative ratio of cDNA sequencing reads to gDNA sequencing reads (namely RNA-to-DNA ratio) of the same target sequence.

The RNA-to-DNA ratio as mentioned above represents the quantity of RNA expression level per copy gDNA. The description covers both 5' terminal of a single-stranded gDNA/cDNA and either end or both ends of a double-stranded gDNA/cDNA. In some embodiments, if ligation to single-stranded gDNA and cDNA, then the universal sequencing adaptor is ligated to the 5' terminal of the gDNA and cDNA. In some embodiments, if ligation to double-stranded gDNA and cDNA, then the universal sequencing adaptor is ligated to either terminal or both terminals of the gDNA and cDNA.

The present application develops a method using Anchored Ligation Priming for Highly Accurate RNA expression (Alpha-RNA) for accurate quantification of multiplex gene RNA expression in biospecimen. Without intending to be bound by theory, it is believed that Alpha-RNA is a novel method based on next-generation sequencing (NGS), and can be used for clinical samples of varied qualities, including highly degraded RNA from formalin-fix paraffin-embedded tissues, and thus is broadly applicable clinically. For example, in cancer diagnosis, Alpha-RNA can accurately quantify those genes relevant in cancer immunity, including PD-1/PD-L1 and immune microenvironment genes such as granzyme and perforin and beyond. Alpha-RNA can be used to guide cancer immunotherapy.

In an embodiment herein, the first polymerase chain reaction process includes the steps of:

(i) contacting a first primer that binds to the cDNA and gDNA sequence at a position that is 3' in relation to the target sequence on the cDNA or gDNA;

(ii) extending by polymerization the first primer till the terminal including the ligated universal sequencing adaptor to produce the single-stranded primer extension product;

(iii) dissociating the single-stranded primer extension product including the complementary sequence to the target sequence from the template strand cDNA or gDNA; and (iv) optionally, repeating steps (i) through (iii) one or more times.

In an embodiment herein, the second polymerase chain reaction process includes the steps of binding a second primer to the sequence at a position that is between the first primer and the target sequence on the cDNA or gDNA. In an embodiment herein, the second polymerase chain reaction process further includes the steps of binding a universal primer to the adaptor complementary sequence.

In an embodiment herein, the above steps (i) through (iii) are repeated for from about 1 cycle to about 100 cycles. For example, steps (i) through (iii) are repeated for about 2 cycles to about 100 cycles, or about 5 cycles to about 50 cycles, for example, about 8 cycles, about 9 cycles, about 10 cycles, about 20 cycles, about 30 cycles, about 40 cycles, about 50 cycles, about 60 cycles, about 70 cycles, about 80 cycles about 90 cycles or about 100 cycles.

In an embodiment herein, the second primer is used to prime and enrich both gDNA and cDNA. Without intending to be bound by theory, it is believed that this allows accurate calculation of cDNA-to-gDNA ratio for the same primer because of primer efficiency is then not an affecting factor (in other words 'cancelled out'), and the affection of different efficiencies caused by using two different primers, namely one for gDNA and another for cDNA, may be excluded. For example, as shown in FIG. 1*b*, at the presence of both genomic DNA and cDNA, a single primer near the exon boundary can prime and enrich both genomic DNA (containing exon and intron) and cDNA (spanning enamoring exons).

In an embodiment herein, the sample is selected from the group of a formalin-fix paraffin-embedded (FFPE) tissue, fresh tissue collected by surgical biopsy or needle aspiration, blood, urine, ascites, pleural effusion, cerebrospinal fluid, pancreas cyst fluid, and a combination thereof. In some embodiments, the sample for testing is selected from the group of a formalin-fix paraffin-embedded tissue, fresh tissue collected by surgical biopsy or needle aspiration, and a combination thereof. In some embodiments, the sample for testing is selected from liquid biopsies such as blood, urine, ascites, pleural effusion, cerebrospinal fluid, pancreas cyst fluid, and a combination thereof. In certain embodiment, the sample could be FFPE tumor tissues to which currently available RNA expression by RNA sequencing is not applicable. In certain embodiment, the sample could be needle biopsy tissues to which the amount of material is limited and currently available RNA expression by RNA sequencing is not applicable.

In an embodiment herein, the method is for quantifying the expression of the target sequence selected from those genes related to immune microenvironment, T-cell functions, antigen presentation, cytotoxic factors, DNA damage repair, immune cell adhesion and migration, housekeeping genes, and other disease relevant genes. For example, in some embodiments, the target sequence can be the immune microenvironment selected from the group of CD274, PDCD1, GZMA, PRF1, and a combination thereof. In some embodiments, the target sequence can be T-cell functions selected from the group of CD3D, CD3E, CD3G, CD6, CD8A, CD8B, FOXP3, SH2D1A, TBX21, TRAT1, and a combination thereof. In some embodiments, the target sequence can be the antigen presentation selected from the group of ATF3, B2M, CCR5, CD1C, CD36, CD4, CD74, CD8A, CD8B, CDC20, CTSS, CTSW CDIC1, CYBB, DTX3L, FCGR1A, HLA genes, IFNG, IRF8, ITGAV, MRC1, PSMB10, PSMB5, PSMB8, PSMB9, PSMC4, SOCS1, TAP1, TAP2, TAPBP, THBD, TNF, TRIM21, UBA7, UBB, UBE2C, ULBP2, VHL, and a combination thereof. In some embodiments, the target sequence can be cytotoxic factors selected from the group of BBC3, CBLC, CD47, CNTFR, FASLG, GHR, GNLY, GZMA, GZMB, GZMH, GZMK, GZAM, IFI16, IFI27, IFI35, IFI6, IFIH1, IFIT1, IFIT2, IFIT3, IFITM1, IFITM2, IFNG, IGF2R, IL11RA, IL12RB2, IL22RA1, IRF1, IRF4, IRF9, ISG15, JAK1, JAK2, JAK3, KIR2DL3, KIR3DL1, KIR3DL2, KLRB1, KLRD1, KLRK1, LIF, MX1, OAS1, OAS2, OAS3, PRF1, PRLR, SIRPA, SPRY4, STAT1, STAT2, TNFSF10, and a combination thereof. In some embodiments, the target sequence can be DNA damage repair selected from the group of ATM, BLM, BRCA1, BRCA2, BRIP1, CCNA1, CCNO, CDK2, DDB2, ERCC3, EXO1, FANCA, H2AFX, ISG15, MGML MLH1, MSH2, MSH6, NBN, NEIL1, PARP4, PIAS4, PMS2, POLD1, POLR2A, RAD50, RAD51, RAD51C, TNKS, TP53, UBA7, UBB, UBE2L XCL1/2, and a combination thereof. In some embodiments, the target sequence can be immune cell adhesion and migration selected from the group of CD2, CD274, CD276, CD28, CD4, CD40, CD40LG, CD58, CD6, CD80, CD86, CD8A, CD8B, CDH1, CDH2, CDH5, CLEC14A, CLEC4E, CLEC5A, CLEC7A, CLECL1, CTLA4, CTNNB1, CXCL12, CXCR4, CYBB, ICAM1, ICAM2, ICAM3, ICAMS, ICOS, ICOSLG, ITGA1, ITGA2, ITGA4, ITGA6, ITGAE, ITGAL, ITGAM, ITGAV ITGAX, ITGB2, ITGB3, ITGB8, MIP9, NCAM1, NECTIN1, NECTIN2, PDCD1, PDCD1LG2, PECAM1, PIK3CA, PIK3CD, PIK3CG, PIK3R1, PIK3R2, PIK3R5, PRKCA, PTPN11, PTPRC, PVR, ROCK1, SELE, SELL, SELP, SIGLEC1, THY1, TIGIT VCAM1, VCAN, VTCN1, and a combination thereof. In some embodiments, the target sequence can be housekeeping genes selected from the group of CHMP2A, GAPDH, B2M, and a combination thereof. In some embodiments, the target sequence is selected from genes related to immune microenvironment, oncogenes, tumor suppressor genes, and a combination thereof.

In an embodiment herein, total nucleic acid is used to perform the reverse transcription in step (a) without removing genomic DNA. Without intending to be bound by theory, it is believed that the gDNA can serve as a perfect internal reference to calculate mRNA per genomic DNA copy.

In an embodiment herein, the first primer has a sequence selected from the group of SEQ ID NOs. 1-379, and analogous thereof with an identity of at least about 80%, at least about 90%, at least about 95%, at least about 98%, or at least about 99% to about 100%, of any one of SEQ ID NOs. 1-379. In some embodiments, the first primer can have a sequence selected from any one of SEQ ID NOs. 1-379, and analogous thereof with an identity of at least about 90%. In some embodiments, the first primer can have a sequence selected from any one of SEQ ID NOs. 1-379, and analogous thereof with an identity of at least about 98%. In some embodiments, the first primer can have a sequence selected from any one of SEQ ID NOs. 1-379.

In an embodiment herein, the second primer has a sequence selected from the group consisting of SEQ ID NOs. 380-758, and analogous thereof with an identity of at least about 80% at least about 90%, at least about 95%, at least about 98%, or at least about 99% to about 100%, of any one of SEQ ID NOs. 380-758. In some embodiments, the first primer can have a sequence selected from any one of SEQ ID NOs. 380-758, and analogous thereof with an identity of at least about 90%. In some embodiments, the first primer can have a sequence selected from any one of SEQ ID NOs. 380-758, and analogous thereof with an identity of at least about 98%. In some embodiments, the first primer can have a sequence selected from any one of SEQ ID NOs. 380-758.

Without intending to be bound by theory, it is believed that the novel features of the Alpha-RNA method herein include but are not limited to: i) a single primer near the gene exon-intron boundary is used to prime both genomic DNA and RNA (reversed transcribed into cDNA); ii) a novel method counting the quantities of genomic DNA and RNA is used; iii) a novel ratio based on RNA to DNA quantities of the same primer is developed to quantify RNA expression level per gene/cell, without the need in the conventional method that relies on house-keeping gene expression level, which is often variable across tissues and patients and associated with imprecise quantification.

Correspondingly, the invention's advantages include but are not limited to: i) high efficiency in quantifying clinically relevant genes; ii) high accuracy in measuring low-level but clinically important genes; iii) cost-efficient, as it allows target enrichment and sequencing of most clinically relevant genes; iv) broad applicability and can be used for various types of clinical samples, including the most accessible but low-quality clinical samples such as FFPE tumor tissues; v) high multiplexing ability (over 100s that is sufficient for clinical diagnosis); and vi) can be integrated with the main stream NGS workflow, without extra sample or additional processing.

Based on the next-generation sequencing (NGS) technology that is widely applicable and becoming the main workhorse in clinical diagnosis, it is believed that the Alpha-RNA method provided herein can open a new area for NGS to precisely and efficiently quantify RNA expressions of a set of highly clinical relevant genes. Alpha-RNA can be used to guide cancer immunotherapy, as the inventors have demonstrated in the clinical study on lung cancer patients who received checkpoint blockade immunotherapy.

An embodiment of the present invention relates to a method of identifying or determining a subject who could be responsive to an immune checkpoint inhibitor (i.e., a ICI responder), which includes the steps of obtaining a sample from the subject and then subjecting the sample to the method of measuring RNA expression level of a target sequence, as provided herein.

In an embodiment herein, the subject having high expression of CD274 and low expression of GZMA is identified or determined as responsive to the immune checkpoint inhibitor. In an embodiment herein, the subject having high expression of CD274 at single exon level is identified or determined as responsive to the immune checkpoint inhibitor. For example, the subject responsive to ICI may have high expression of CD274 exon6.

An embodiment of the present invention relates to a method of treating cancer, including applying an immune checkpoint inhibitor to a subject in need thereof, wherein the subject is tested for RNA expression level of a target sequence by using the method of of measuring RNA expression level of a target sequence as described herein before administrating the immune checkpoint inhibitor to the subject.

In an embodiment herein, the subject has high expression of CD274 and low expression of GZMA.

There is no gold standard/cutoff to determine high or low expression of target sequences. However, in this invention, in view of the reportedly about 20% NSLC patients response to ICIs[3,4], we define High and Low expression based on a cutoff percentile 20% among the patient group (>20% percentile as High expression and <=80% as Low expression). The cutoff percentile is calculated by using the RNA expression levels among all the NSCLC cancer patients.

In an embodiment herein, the subject has high expression of CD274 at single exon level. For example, the subject responsive to ICI may have high expression of CD274 exon6.

Without intending to be bound by theory, it is believed that the ability to pinpoint down to a single exon level, in contrast to what is generally available in conventional RNA-seq and expressed as RPM (read per million sequences), allows quantification of alternatively spliced mRNA variants that in certain scenario is important in disease initiation, progression, response to drugs, and patient survival.

The methods provided herein are applicable for cancers of any tissue type, of human and animal, and also any diseases, cancers and non-cancer diseases, where mRNA gene expression level testing are involved.

In some embodiments, the cancer is non-small cell lung cancer.

In an embodiment herein, the non-small cell lung cancer is selected from the group of adenocarcinoma, squamous cell carcinoma, large-cell lung carcinoma and a combination thereof. In an embodiment herein, the non-small cell lung cancer is selected from adenocarcinoma, squamous cell carcinoma and a combination thereof. In an embodiment herein, the non-small cell lung cancer can be squamous cell carcinoma.

In an embodiment herein, the immune checkpoint inhibitor is selected from the group of a PD-1 inhibitor, a PD-L1 inhibitor, and a combination thereof.

In an embodiment herein, the immune checkpoint inhibitor is selected from the group of pembrolizumab, nivolumab, atezolizumab, durvalumab, and a combination thereof.

An embodiment of the present invention relates to a kit for performing the above-described method of measuring RNA expression level of a target sequence in a sample by simultaneously enriching a target DNA and corresponding RNA and calculating a RNA-to-DNA ratio of the same target sequence, the kit includes:

(e) a reverse transcriptase for transcribing RNA into complementary DNA (cDNA);
(f) a universal sequencing adaptor to be ligated to a terminal of gDNA and cDNA in the sample;
(g) a first primer that binds to the cDNA and gDNA sequence at a position that is 3' in relation to the target sequence on the cDNA or gDNA; and
(h) a second primer that binds to the target sequence at a position that is between the first primer and the target sequence on the cDNA or gDNA.

In some embodiments herein, the the first primer has a sequence selected from the group consisting of SEQ ID NOs. 1-379, and analogous thereof with an identity of at least about 80% of any one of SEQ ID NOs. 1-379. In some embodiments, the first primer can have a sequence selected from any one of SEQ ID NOs. 1-379, and analogous thereof with an identity of at least about 90%. In some embodiments, the first primer can have a sequence selected from any one of SEQ ID NOs. 1-379, and analogous thereof with an identity of at least about 98%. In some embodiments, the first primer can have a sequence selected from any one of SEQ ID NOs. 1-379.

In some embodiments herein, the second primer has a sequence selected from the group consisting of SEQ ID NOs. 380-758, and analogous thereof with an identity of at least about 80% of any one of SEQ ID NOs. 380-758. In some embodiments, the first primer can have a sequence selected from any one of SEQ ID NOs. 380-758, and analogous thereof with an identity of at least about 90%. In some embodiments, the first primer can have a sequence selected from any one of SEQ ID NOs. 380-758, and analogous thereof with an identity of at least about 98%. In some embodiments, the first primer can have a sequence selected from any one of SEQ ID NOs. 380-758.

Immune checkpoint inhibitors (ICIs) have shown unprecedented clinical activity in non-small cell lung cancer (NSCLC) and have dramatically changed how NSCLC is treated[1]. Five ICIs have been approved for the treatment of NSCLC[2], including anti-PD-1 antibody pembrolizumab and nivolumab, anti-PD-L1 antibody atezolizumab and durvalumab, anti-CTLA antibody ipilimumab, which is required to be in combination with nivolumab. Although ICIs have durable response and prolonged survival in some patients, the objective response rate (ORR) is 20%-30%[3,4] for unselected NSCLC patients.

Without intending to be bound by theory, it is believed that the development of next generation sequencing (NGS) provides comprehensive overview of molecular and genetic features of tumor profile, which may help ICI biomarker discovery. Several studies have found that structural variations of PD-L1 affect response to immunotherapy. One publication reported that 3' region disruption of PD-L1 leads to its elevated expression, which enables immune evasion of EG7-OVA tumour cells in mice. This structural variation affects multiple cancers including adult T-cell leukaemia/lymphoma (ATL), diffuse large B cell lymphoma, and stomach adenocarcinoma[16]. Moreover, a few publications have reported the existence of secreted form of PD-L1(sPD-L1)[17,18,19]. The function of sPD-L1 on the predictive of ICIs treatment is on debate. One research reported that C-terminal-deficient splicing variant of PD-L1 is highly secreted and this variant contribute to the resistance to anti-PD-L1 treatment in NSCLC[17]. Interestingly, another publication found that sPD-L1 concentration was elevated during ICIs but it did not affect the survival of NSCLC patients[18]. Thus, it is needed to investigate the structural variations of PD-L1 in NSCLC analyze whether structural variations of PD-L1 could serve as a prognostic marker for NSCLC patients.

The present invention develops a NGS-based method to detect the mRNA expression CD274 (encoding PD-L1) and its various splicing variants in NSCLC patients. The present invention finds that the mRNA expression detected by NGS has a good correlation with its protein expression detected by IHC (Dako 22C3). More importantly, survival analysis shows that high expression of CD274 exon3 and low expression of CD274 exon5, encoding the secreted and 3'-UTR truncated forms of PD-L1, has worst overall survival (OS) when compared with other splicing forms or low expression of PD-L1 among all NSCLC patients. These results suggest that detection of PD-L1 expression in NSCLC patients by next generation sequencing could be used to evaluate the prognosis of NSCLC patients and guide personal immune checkpoint therapy. Moreover, the examples herein analyze the NSCLC patients treated with anti-PD1 therapy and survival analysis show that patients with high expression of GZMA and CD274 have longer Progression-Free-Survival (PFS). Without intending to be bound by theory, it is believed that the personalized treatment based on the NGS method provided herein may improve PD-L1 therapy outcomes in non-small cell lung cancer (NSCLC).

Without intending to be bound by theory, it is believed that T cell infiltration is also of vital for cancer survival and ICI therapy[10]. T cell infiltration is an independent predictive marker for gastric cancer[11] and NSCLC[12], patients with higher $CD8^+$ TIL density would have favorable survival. Also, NSCLC patients with increased $CD8^+$ T cell infiltration may have longer PFS after ICI therapy[13]. However, patents could still fail from ICI therapy because of T cell exhaustion. It is believed that the exhausted T cells in the tumor microenvironment have decreased effector cytokine production and cytolytic activity, leading to the failure of cancer elimination[14]. One publication has shown that T cell exhaustion signatures could predict ICIs response[15], patients with higher dysfunction score would have worse survival. Thus, the examples herein will also include cytotoxic marker and combine with PD-L1 to predict the survival of ICIs therapy.

EXAMPLES

The examples illustrate a next-generation sequencing-based method to quantify mRNA expression of CD274 (encoding PD-L1), its splicing isoforms, T-cell activity factors, and other genetic drivers to triage patients for ICI therapies. The method uses anchored ligation priming for highly accurate RNA expression (Alpha-RNA). The examples evaluated Alpha-RNA with two retrospective non-small cell lung cancer (NSCLC) cohorts. Cohort I includes 182 NSCLC patients who underwent surgery resections, with available clinical IHC assay results and were followed up for overall survival analysis. Cohort II includes 33 patients who failed first-line therapies and further received anti-PD-1 therapies, prior to which needle biopsies were obtained, and were followed up for progression-free survival analysis following the treatment. In Cohort I, the mRNA expression of CD274 assessed by Alpha-RNA is highly correlated with routine clinical TIC protein expression ($R^2$=0.51, P value <0.01). By Alpha-RNA, ALK mRNA is indeed expressed in those ALK fusion-positive cases and very low or no expression in ALK negative cases. Interestingly, patients with high expression of CD274 exon6 and low expression of exon4 (presumably resembling those secreted and 3' UTR-truncated PD-L1 isoforms) had the worst overall survival when compared to patients with other CD274 splicing isoforms or patients with low CD274 expression (P value <0.01). The finding is consistent with the results from the analysis of the Cancer Genome Atlas (TCGA) data. Furthermore, it is found that patients with high expression of CD274 and low expression of GZMA have best response and progression-free survival to ICIs (P value <0.01), suggesting that GZMA, in additional to CD274, may be additional predictive marker for triaging patients to receive ICIs therapy. Overall, the data herein demonstrates that Alpha-RNA may be an effective molecular diagnosis assay for RNA expression of multiple genes and their isoforms to guide cancer immunotherapy.

Materials and Methods

Patients and Specimens

Cohort I retrospectively recruit 208 NSCLC patients who underwent surgical resection between 2014 and 2016 at Cancer Hospital of Zhejiang Province, Hangzhou, Zhejiang, China. Pathologic and clinicopathologic staging of the diagnoses are performed according to the World Health Organization (WHO) histological classification and tumor-node-metastasis (TNM) classification system. In total, 75 patients with squamous cell carcinoma and 131 patients with adenocarcinoma are included and basic clinical parameters are recorded. Written informed consent from all patients are obtained, and the study is approved by Research Ethics Committee of Cancer Hospital of Zhejiang Province (IRB-2018-24).

Immunohistochemistry (IHC)

Lung tissues collected by surgery underwent fixation, dehydration, transparentizing, immersion and embedding followed by section at a thickness of 4 m. Epitope unmasking is done by antigen retrieval reagent. After washing with Tris Buffered Saline with Tween 20 (TBST), slides are incubated overnight at 4° C. with primary antibody. The expression of PD-L1 is then detected by detection kit following manufacturer's instruction. The anti-PD-L1 antibody is used to detect the protein level of PD-L1.

Targeted DNA and RNA Sequencing

The example uses the anchored multiplex PCR method previously described for targeted DNA and RNA sequencing[20]. First, total nucleic acid is extracted from formalin-fixed paraffin-embedded lung tissue samples with FormaPure XL RNA kit (Beckman Coulter life sciences, UK). Total nucleic acid is used to perform reverse transcription without removing genomic DNA. Briefly, random hexamer (300 ng/μL) and dNTP (10 nM) are added to sample DNA/RNA and incubated at 65° C. for 5 min to denature RNA. To synthesize first strand cDNA, SuperScript IV Reverse Transcriptase (Catalog no.18091050, Invitrogen), 5× buffer, RNaseOUT and fresh DTT are added and the following program is performed: 25° C. 10 min, 42° C. 30 min, 70° C. 15 min. Second strand cDNAs are then synthesized by incubating at 16° C. for 2 hours with the addition of DNA Polymerase I (Catalog no. M0209S, New England Biolabs), RNase H (Catalog no. M0297S, New England Biolabs), and 10× second strand reaction buffer (Catalog no. B6117S, New England Biolabs). The reverse transcription product is then purified with 1.8×AMPure XP magnetic beads (Catalog no. A63881, Beckman Coulter). Fragmented gDNA and cDNA mixture is ligated with an adaptor and followed by 15 cycles of PCR amplification. The amplicon products are purified and used for a hemi-nested PCR for enrichment of targets of interest. The example designs gene specific primers (GSPIs) and their 3' nested primers GSP2 near the exon/intron boundary. At the presence of both genomic DNA and cDNA, a single primer near the exon boundary can prime and enrich both genomic DNA (containing exon and intron) and cDNA (spanning enamouring exons). Using this method, the RNA to DNA ratio per enrichment primer can be calculated and used to quantify RNA expression level.

Statistical Analysis

Cox Proportional Hazards regression analyses are performed to assess the associations between biomarkers and overall survival. Differences are considered statistically significant at a two-sided p-value of <0.05. R studio, package survival (https://cran.r-project.org/web/packages/survival/index.html) and package survminer (https://cran.r-project.org/web/packages/survminer/index.html) are used to analyze the relationship between PD-L1 and patients' survival.

Results

Targeted Next Generation Sequencing and Immunohistochemistry

Figure 1B:
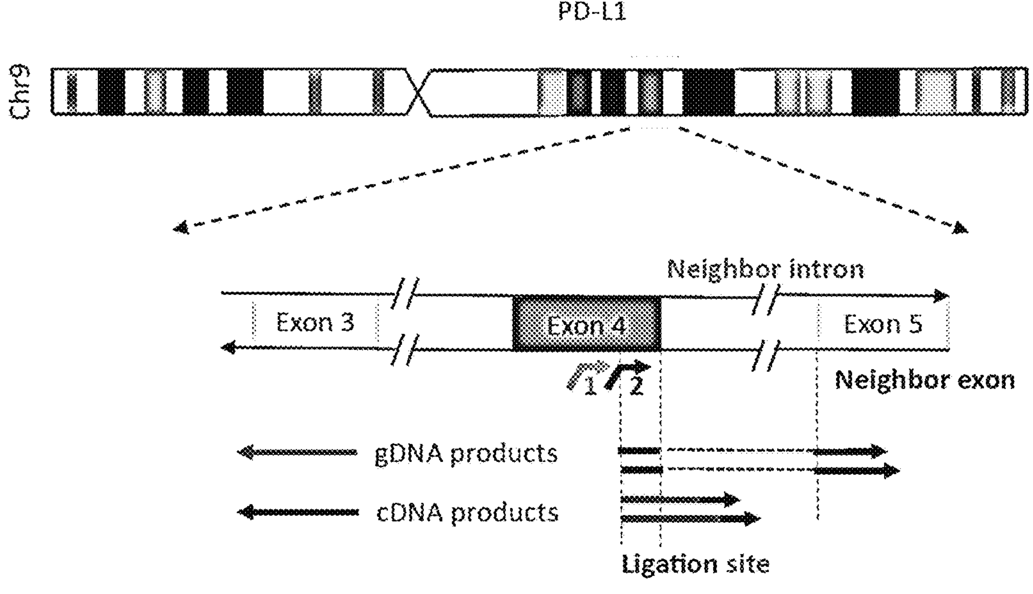
FIG. 1*b* shows a schematic description of Anchored Ligation Priming for Highly Accurate RNA expression (Alpha-RNA), gene specific primers (GSP1s) and their 3' nested primers GSP2 near the exon/intron boundary.
Figure 2A:
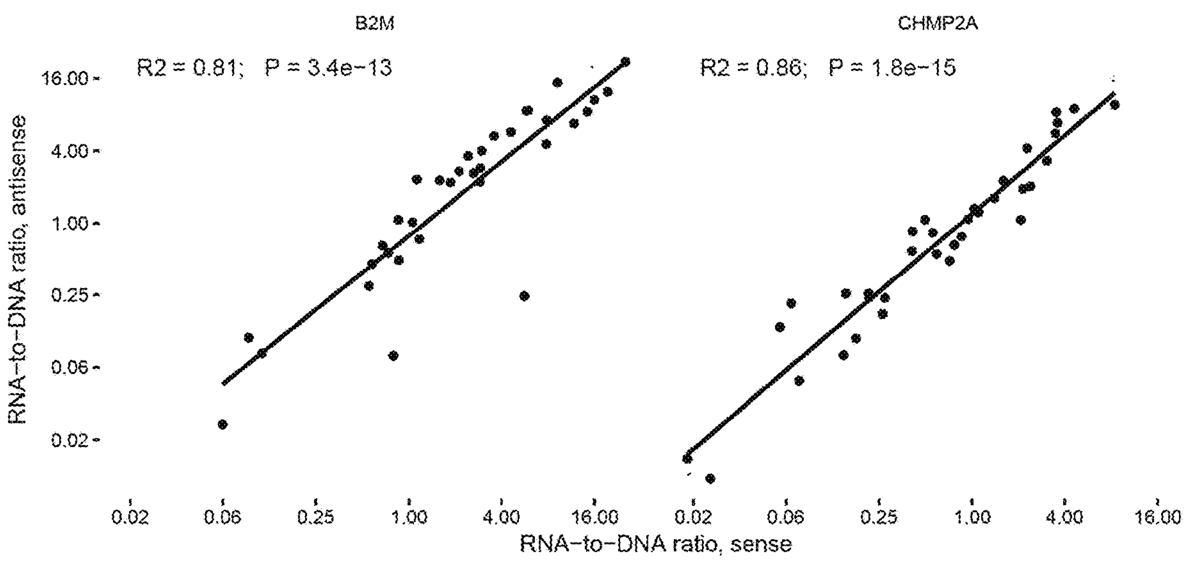
FIG. 2*a* shows a linear regression between expression data from sense primer and antisense primer (left: B2M, right: CHMP2A)
Figure 2B:
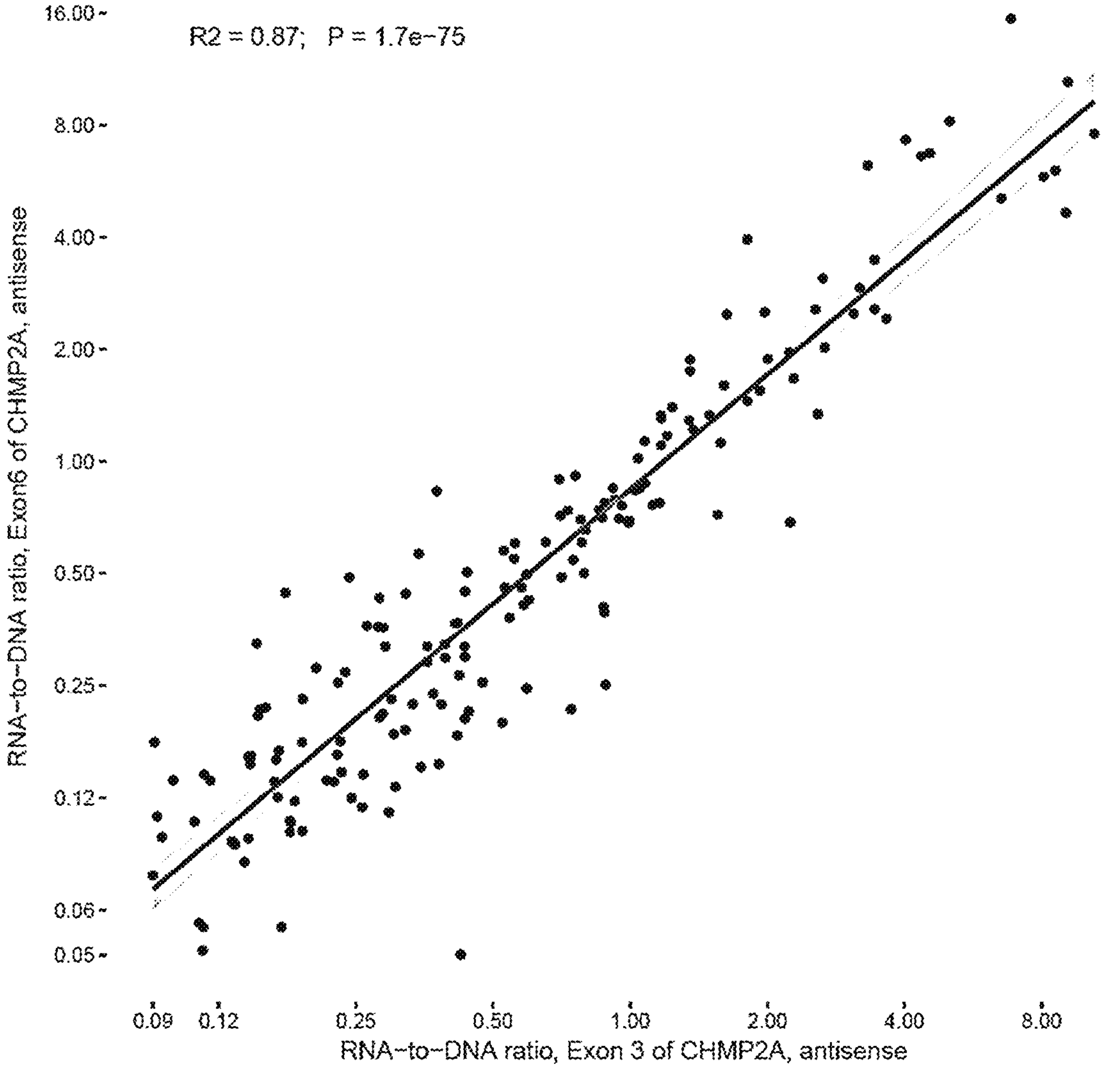
FIG. 2*b* shows a linear regression between exon3 expression data of CHMP2A and exon6 expression data.
Figure 2C:
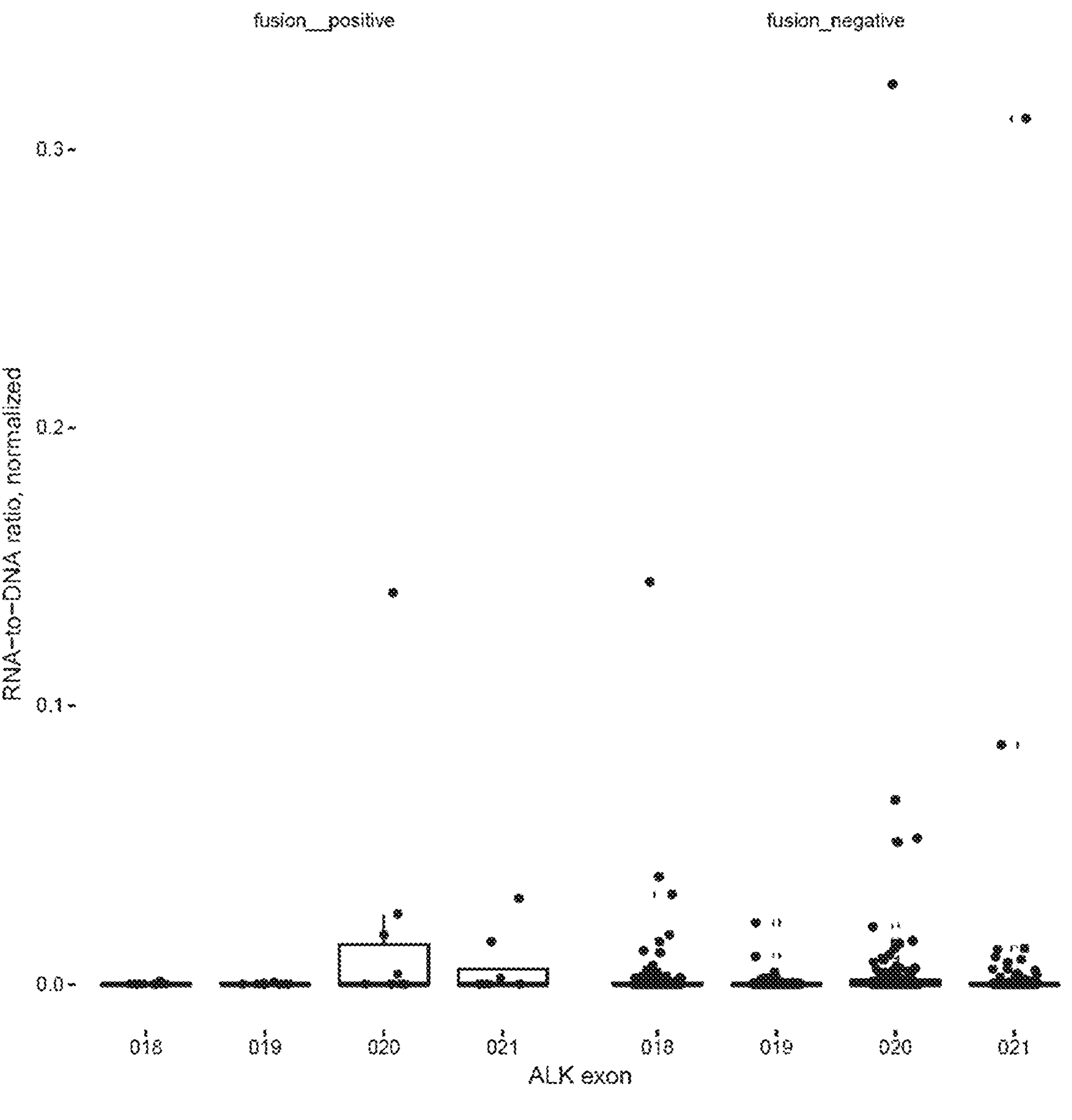
FIG. 2*c* shows a graph of RNA expression of ALK in fusion-positive samples (left) and fusion-negative samples (right)
Figure 2D:
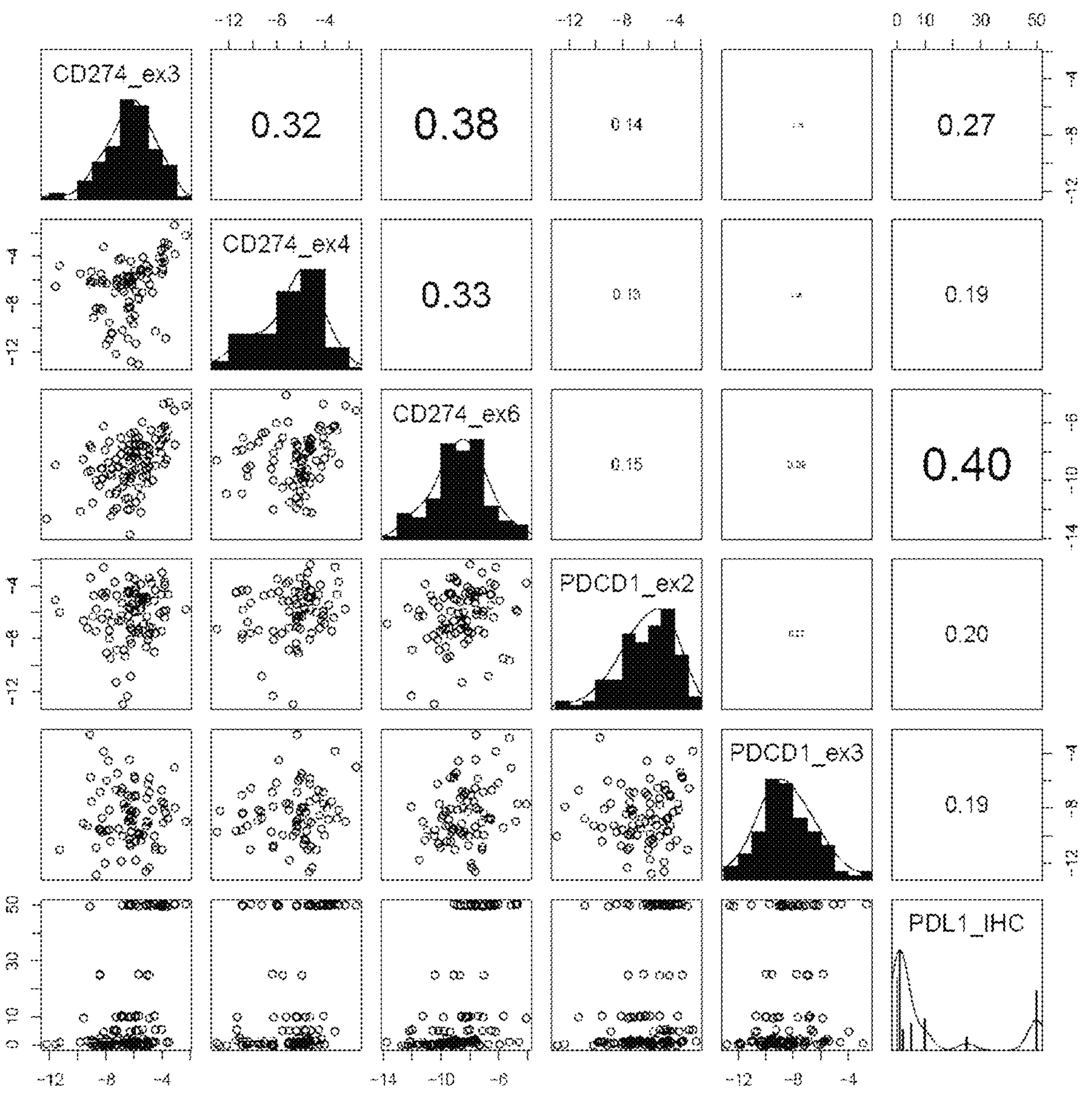
FIG. 2*d* shows a correlation between RNA expression of CD274 (encoding PD-L1) exons 3, 4, and 6 and PDCD1 (encoding PD-1) and the protein expression of PD-L1.

ALPHA-RNA method is based on anchored multiplex PCR, FIG. 1*a* and FIG. 1*b* show the schematic description of the targeted gDNA and cDNA sequencing. To test the reliability of the NGS method, RNA-to-DNA ratio of two house-keeping gene CHMP2A and B2M is calculated with antisense and sense. As shown in FIG. 2*a*, antisense RNA-to-DNA ratio has excellent correlation with sense RNA-to-DNA ratio both in CHMP2A and B2M, the correlation coefficient is 0.81 (p<0.001) and 0.86 (p<0.001) respectively. In the same house-keeping gene, RNA-to-DNA ratio of different exon is calculated, and RNA-to-DNA ratio of CHMP2A exon3 has good correlation with exon6 (FIG. 2*b*). ALK gene fusion and ALK expression are also quantified. As the box plot shows in FIG. 2*c*, ALK gene fusion leads to the up-regulation of ALK, which is consistent with other publications. IHC is the current standard method for PD-L1 detection but its limitation is obvious. Using the new method of this invention, the inventors quantify the expression of CD274 exons 3, and 5 and PDCD1 (encoding PD-1) exons 2 and 3. Also, protein expression of PD-L1 is assayed by IHC. The results showed that RNA expression of CD274 exons 3 and 5 are correlated with protein expression level of PD-L1 (correlation coefficient is 0.27 and 0.40, respectively, Spearman's rank test, FIG. 2*d*). The RNA expression of PD-1 (exons 2 and 3) is not correlated with PD-L1 protein expression (FIG. 2*d*).

Figure 3A:
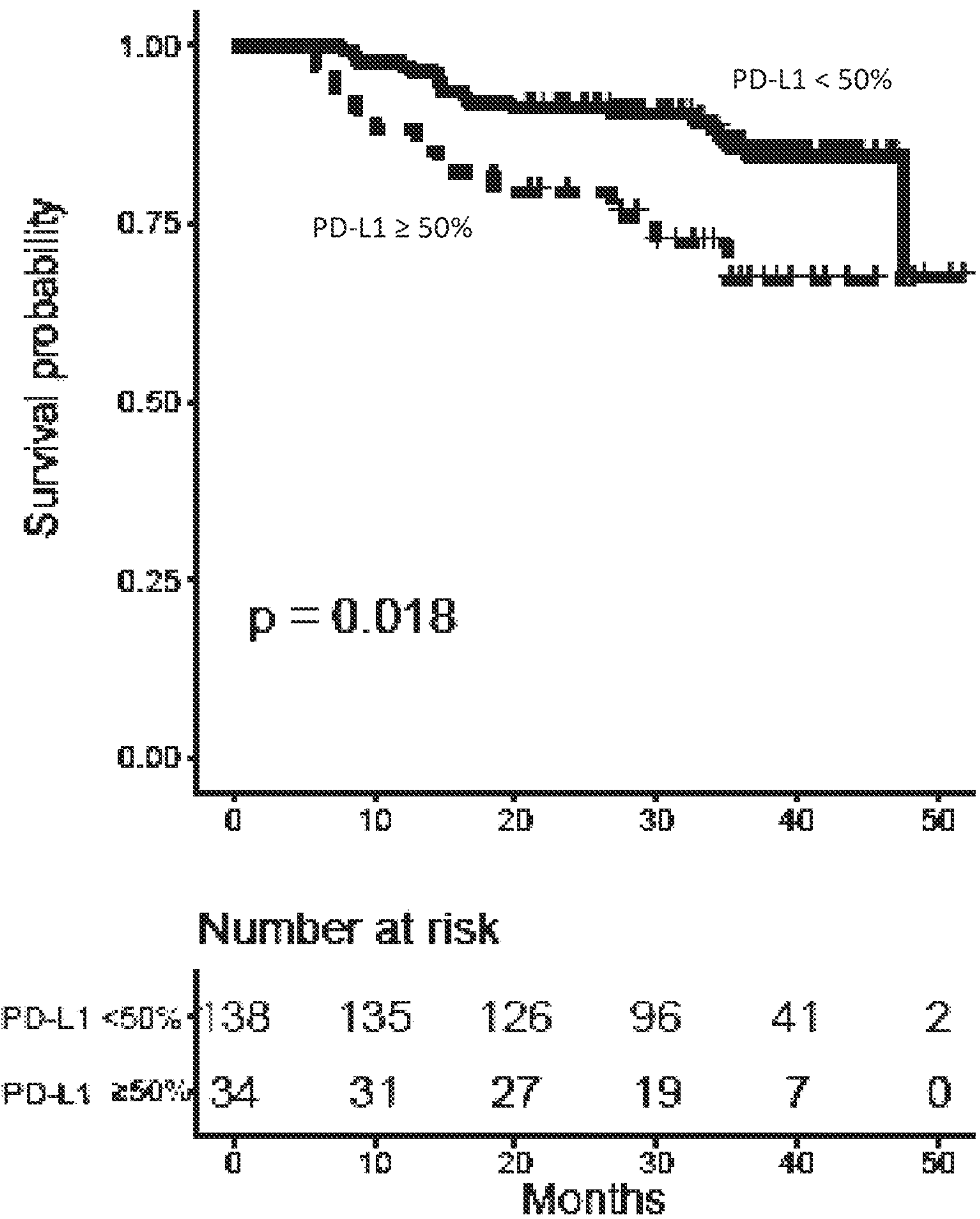
FIG. 3*a* shows Kaplan-Meier survival curves of NSCLC patients with PD-L1 immunohistochemistry staining of tumor tissue showing >=50% positive cells (n=34) and with <50% positive cells (n=138)
Figure 3B:
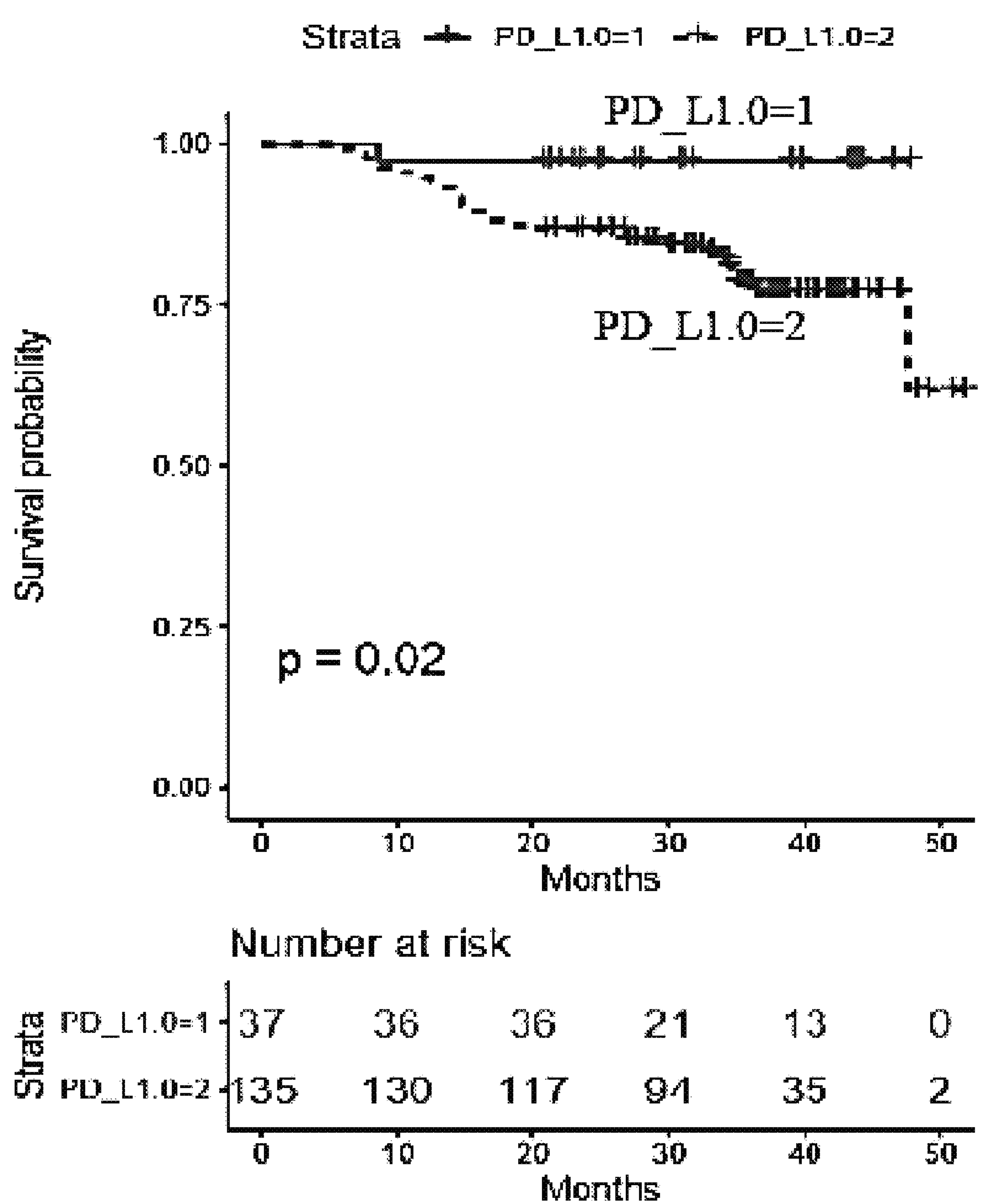
FIG. 3*b* shows Kaplan-Meier survival curves of NSCLC patients with PD-L1 protein expression by immunohistochemistry (IHC) staining of tumor tissue showing any positive cells, i.e., >0% ('PD L1.0=2'; n=135) and no positive cells, i.e., 0% ('PD L1.0=1'; n=37)
Figure 3C:
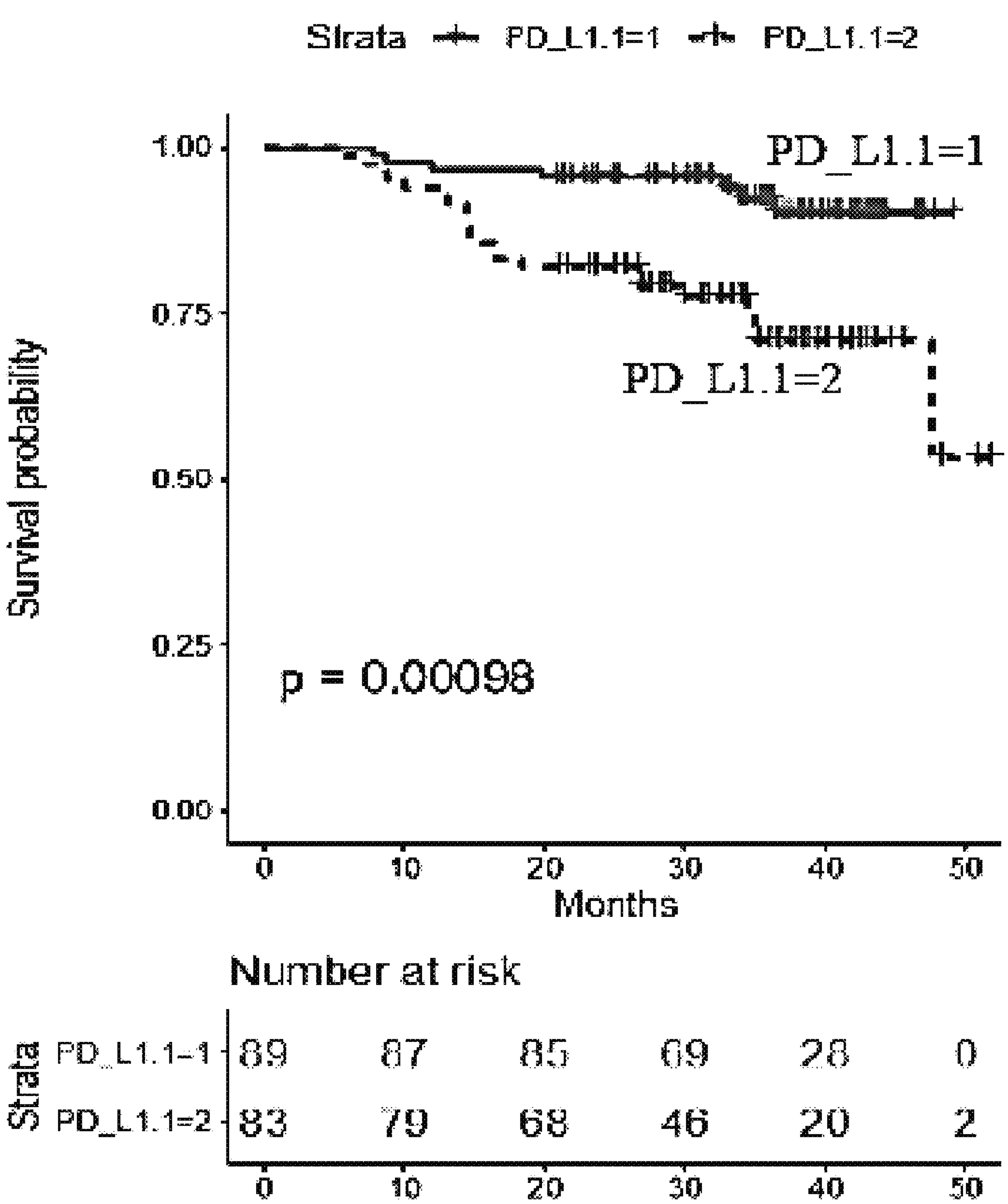
FIG. 3*c* shows Kaplan-Meier survival curves of NSCLC patients with PD-L1 protein expression by immunohistochemistry (IHC) staining of tumor tissue showing >=1% positive cells ('PD_L1.1=2'; n=83) and no positive cells ('PD_L1.1=1'; n=89)
Figure 3D:
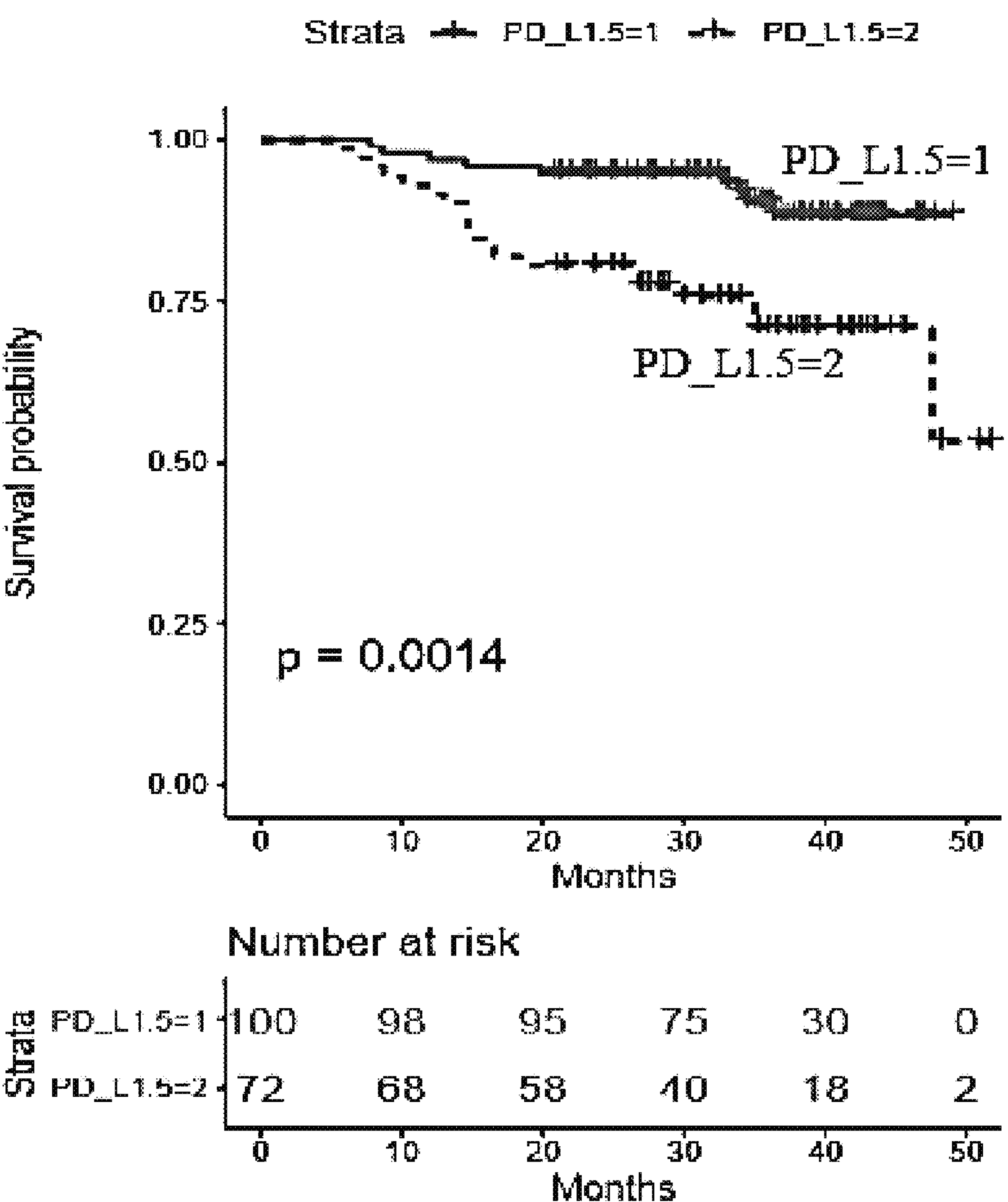
FIG. 3*d* shows Kaplan-Meier survival curves of NSCLC patients with PD-L1 protein 10 expression by immunohistochemistry (IHC) staining of tumor tissue showing >=5% positive cells ('PD_L1.5=2'; n=72) and no positive cells ('PD_L1.5=1'; n=100)
Figure 3E:
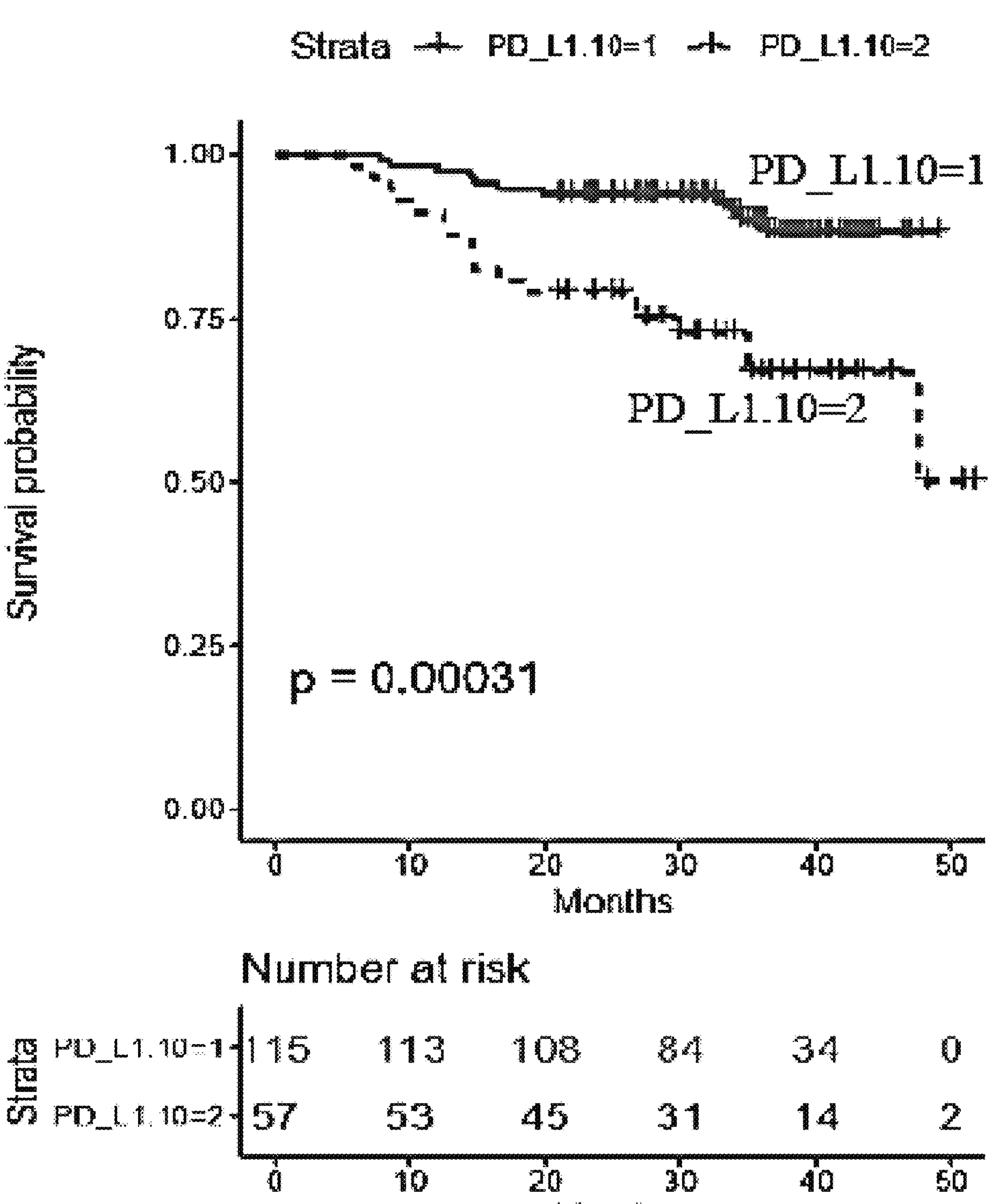
FIG. 3*e* shows Kaplan-Meier survival curves of NSCLC patients with PD-L1 protein expression by immunohistochemistry (IHC) staining of tumor tissue showing >=10% positive cells ('PD_L1.10=2'; n=57) and no positive cells ('PD_L1.10=1'; n=115)
Figure 3F:
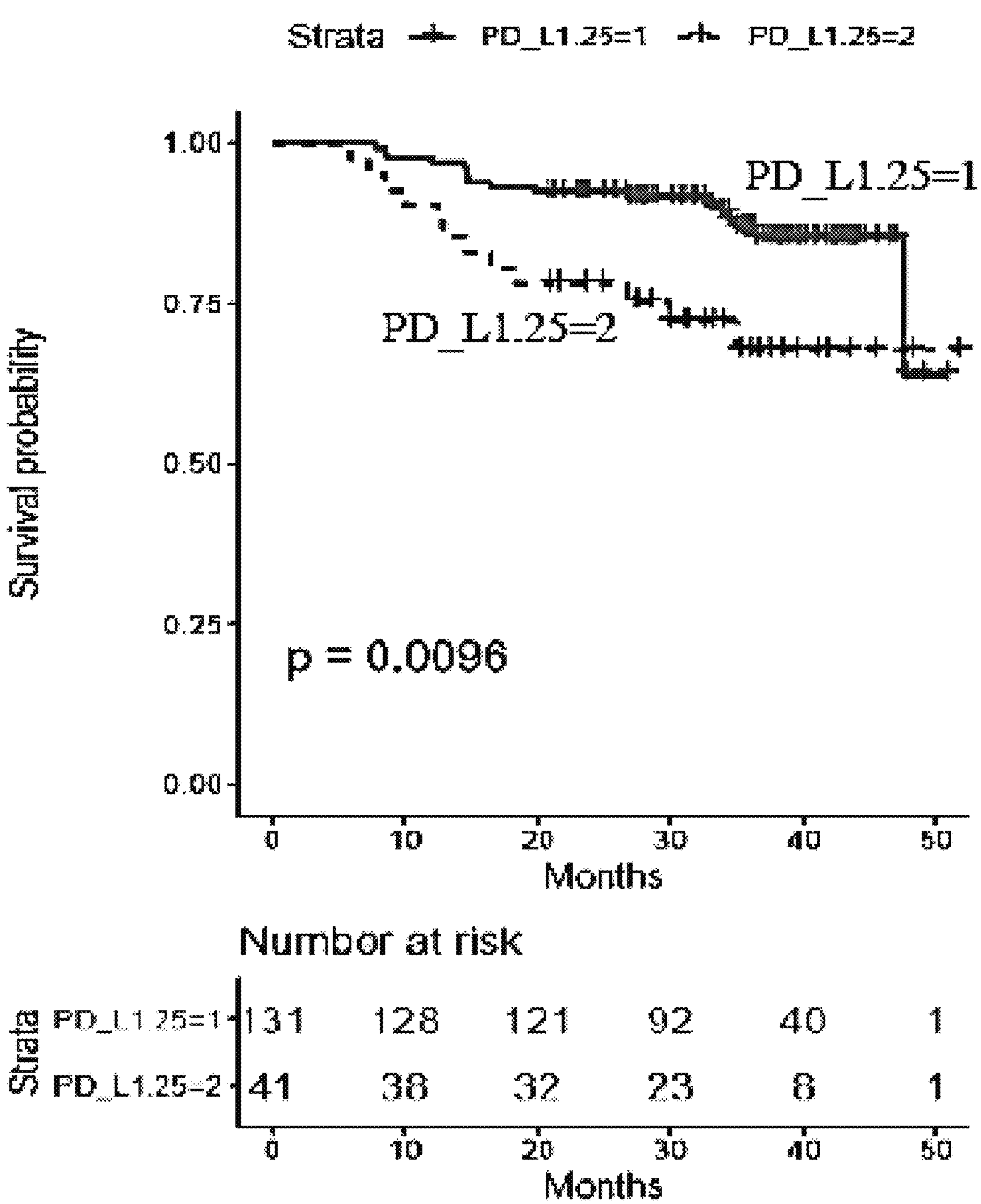
FIG. 3*f* shows Kaplan-Meier survival curves of NSCLC patients with PD-L1 protein expression by immunohistochemistry (IHC) staining of tumor tissue showing >=25% positive cells ('PD_L1.25=2'; n=41) and no positive cells ('PD_L1.25=1'; n=131)
Figure 3G:
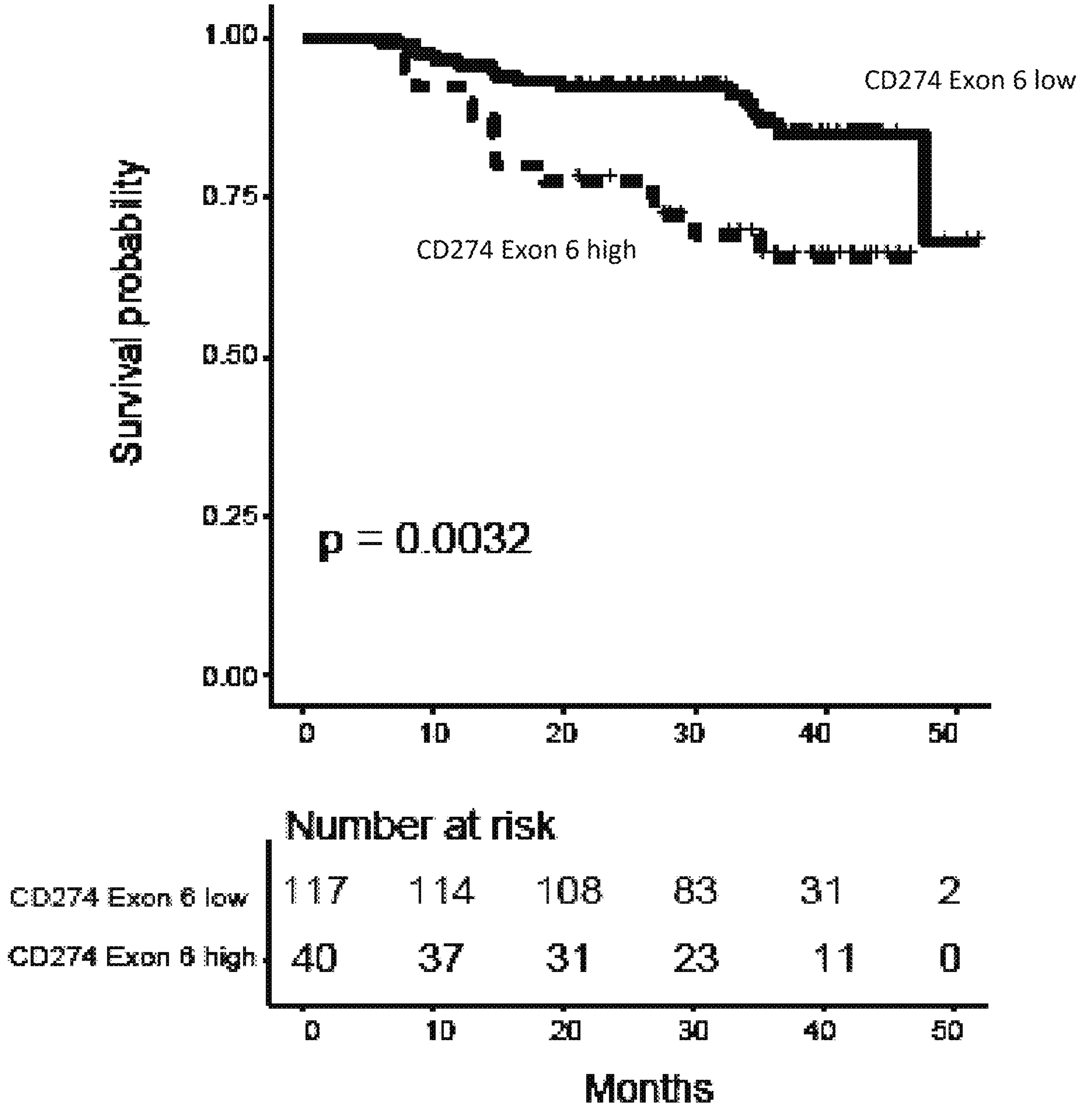
FIG. 3*g* shows Kaplan-Meier curves for survival of NSCLC patients with RNA expression by the Alpha-RNA method showing CD274 exon6 high (n=40) and CD274 exon6 low (n=117)
Figure 3H:
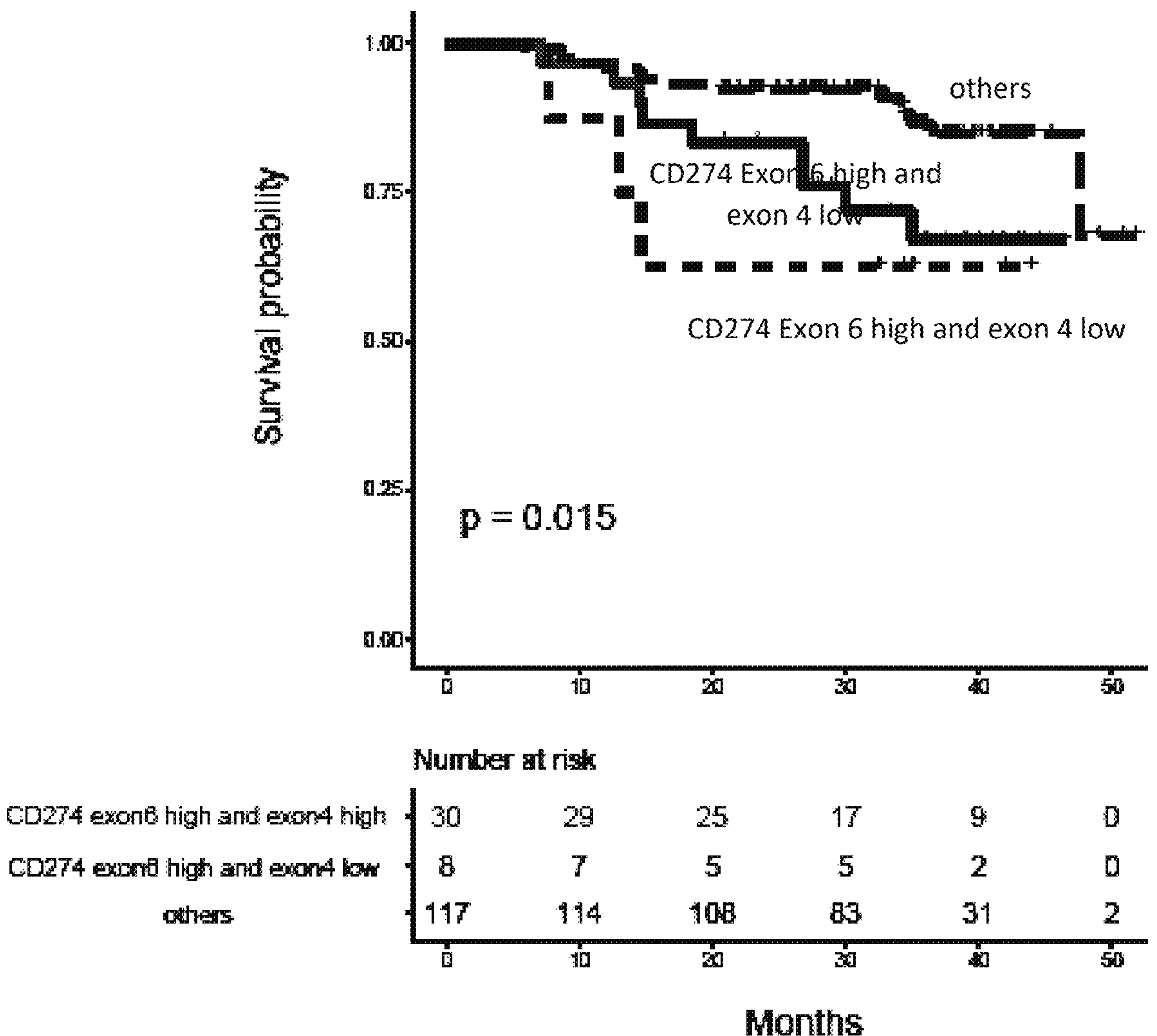
FIG. 3*h* shows Kaplan-Meier curves for survival of NSCLC patients with RNA expression by the Alpha-RNA method showing CD274 exon6 high and exon4 low (n=8), CD274 exon6 high and exon4 high (n=30) and CD274 exon6 low ("others"; n=117)

High Expression of CD274 Exon3 and Low Expression of CD274 Exon5 as a Negative Prognostic Marker in NSCLC Patients Next, the inventors assess the association between PD-L1 expression (both protein and RNA expression) and patient overall survival. Using different PD-L1 IHC positive tumor cellularity percentage cutoffs, patients with high expression of PD-L1 have shorter OS than patients with low PD-L1 expression consistently across the different cutoffs (FIG. 3*a* and FIGS. 3*b*-3*f*). Then, the inventors investigate whether RNA expression of CD274, at the exon-level/isoform level, could be used to predict NSCLC patients' survival. FIG. 3*g* shows that patients with high expression of CD274 exon6 have better OS. It is also found that patients with high expression of CD274 exon 6 and low expression of exon 4, likely reflecting the isoform with missing transmembrane domain, have the worst OS than patients with other expressions (P=0.00028, FIG. 3*h*). Univariate Cox regression analysis is performed and reveals that not only PD-L1 protein level but also the new PD-L1 RNA group (CD274 exon4− and exon6+) is significantly associated with survival (Table 1 below).

TABLE 1

Hazard ratios and 95% confidence intervals of PD-L1 protein expression (at different cut-off percentiles, IHC assay) and PDL1 RNA expression (continuous mean or dichotomous groups, ALPHA RNA assay) in studied non-small cell lung cancer patients, with adjustment for gender, age, and smoking status, using COX regression model.

| | HR (95% CI for HR) | p. value |
|---|---|---|
| Gender | 0.49 (0.2153-1.1363) | 0.097 |
| Age | 1 (0.97309-1.0641) | 0.44 |
| Smoking | 1.6 (0.7305-3.2984) | 0.25 |
| PD_L1.50 | 2.9 (1.3143-6.2719) | 0.0082 |
| PD_L1.25 | 2.5 (1.1851-5.4062) | 0.016 |
| PD_L1.10 | 3.6 (1.6821-7.726) | 0.00098 |
| PD_L1.1 | 3.8 (1.6002-8.8874) | 0.0024 |
| PDL1 RNA mean value | 2.2 (1.023-4.761) | 0.044 |
| PDL1.RNA Group | 2.1 (1.2495-3.6089) | 0.0054 |

Validate the Prognostic Role of CD274 Using the Cancer Genome Atlas (TCGA) Data

Figures 4A, 4B:
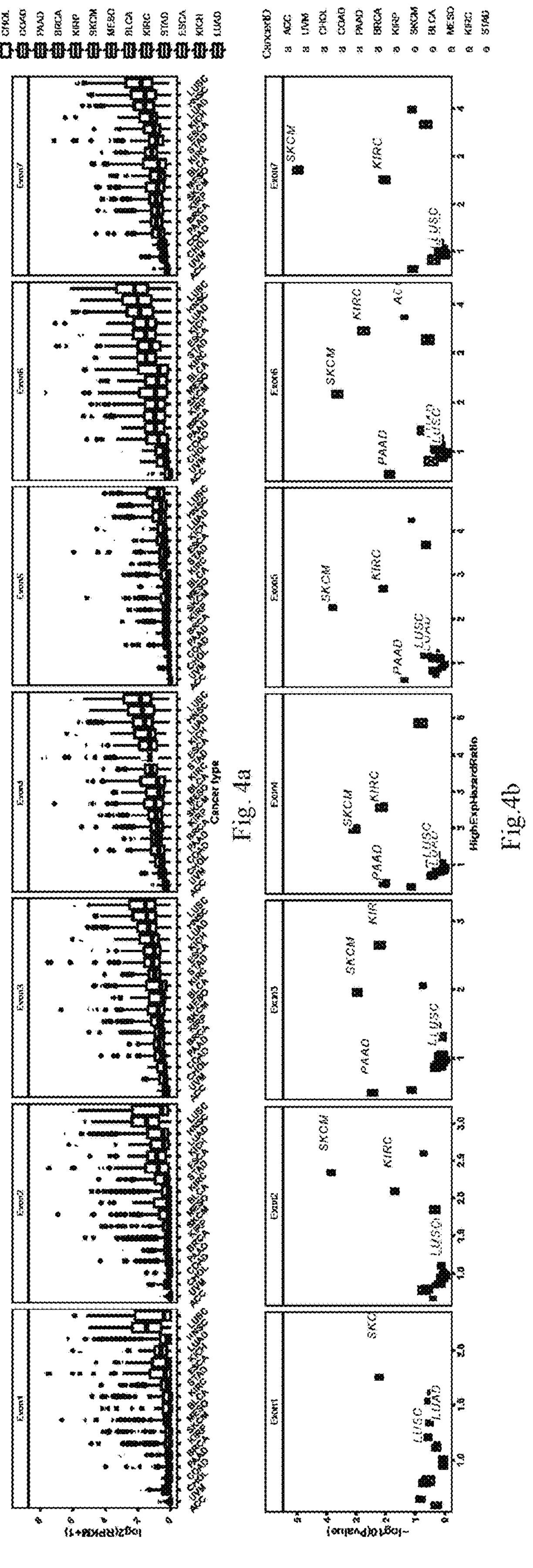
FIG. 4*a* shows the expression of CD274 (different exons) in TCGA cancer types.
FIG. 4*b* shows the Cox regression-computed Hazard Ratio (x-axis) for death in CD274 exon high expression patients versus CD274 low expression patients by the statistical significance difference (y-axis; −log 10 transformed P value)
Figure 4C:
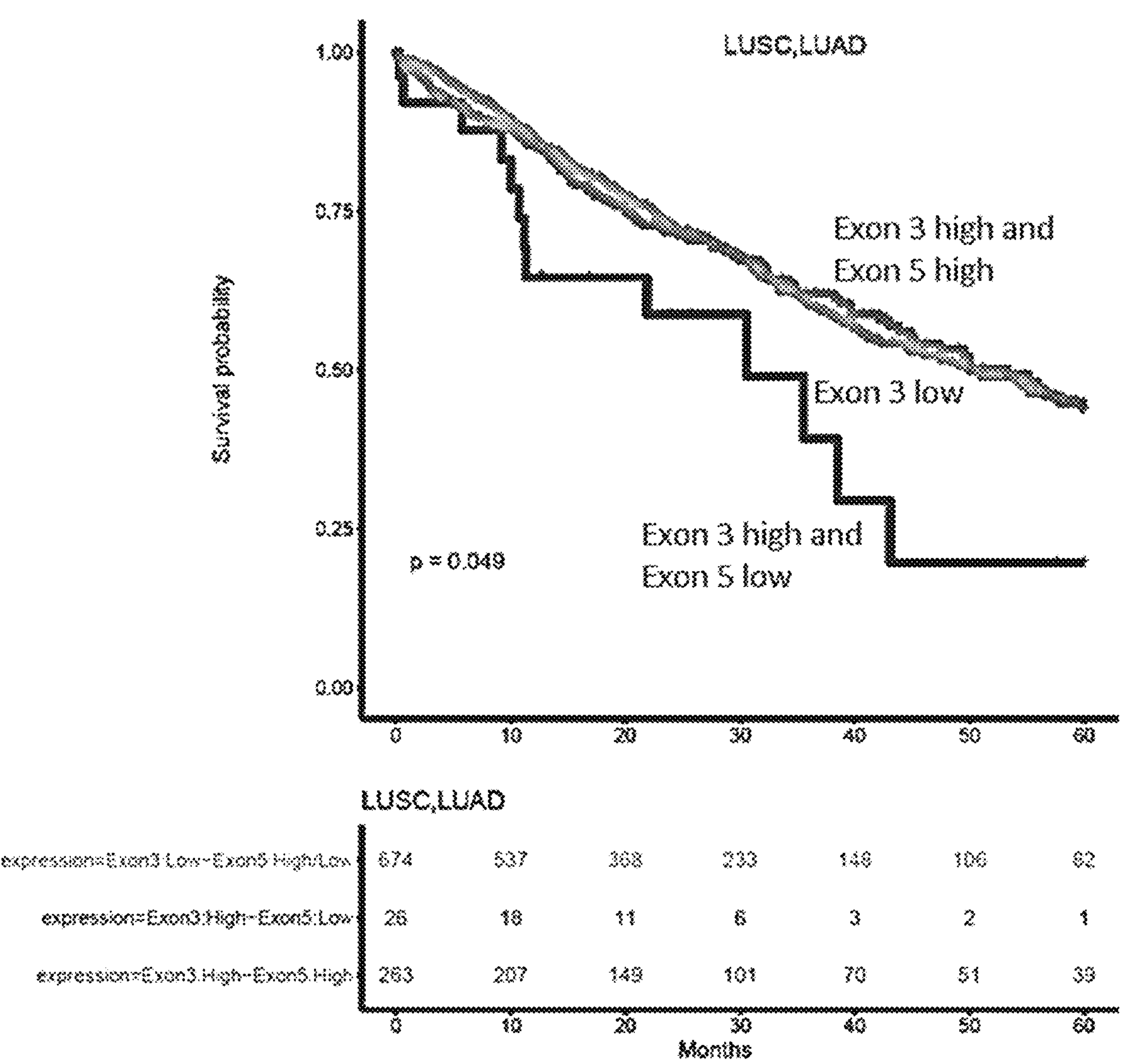
FIG. 4*c* shows Kaplan-Meier curves for survival of TCGANSCLC patients with CD274 exon3 high expression and exon5 low expression (n=26), CD274 with CD274 exon3 high expression and exon5 high expression (n=263) and CD274 exon3 low expression (n=674)

There is little data on the mRNA level of PD-L1 and NSCLC clinical outcomes. Thus, the inventors analyze the TCGA data across different tumor types and found that high expression of CD274 at the single exon level does not increase the hazard ratio (FIGS. 4*a* and 4*b*). However, in combined exon analysis, high expression of CD274 exon3 and low expression of CD274 exon5—the group likely resembling the secreted and 3'-UTR truncated forms of PD-L1—have the worst OS when compared with other splicing forms among all NSCLC patients (FIG. 4*c*).

Figure 5A:
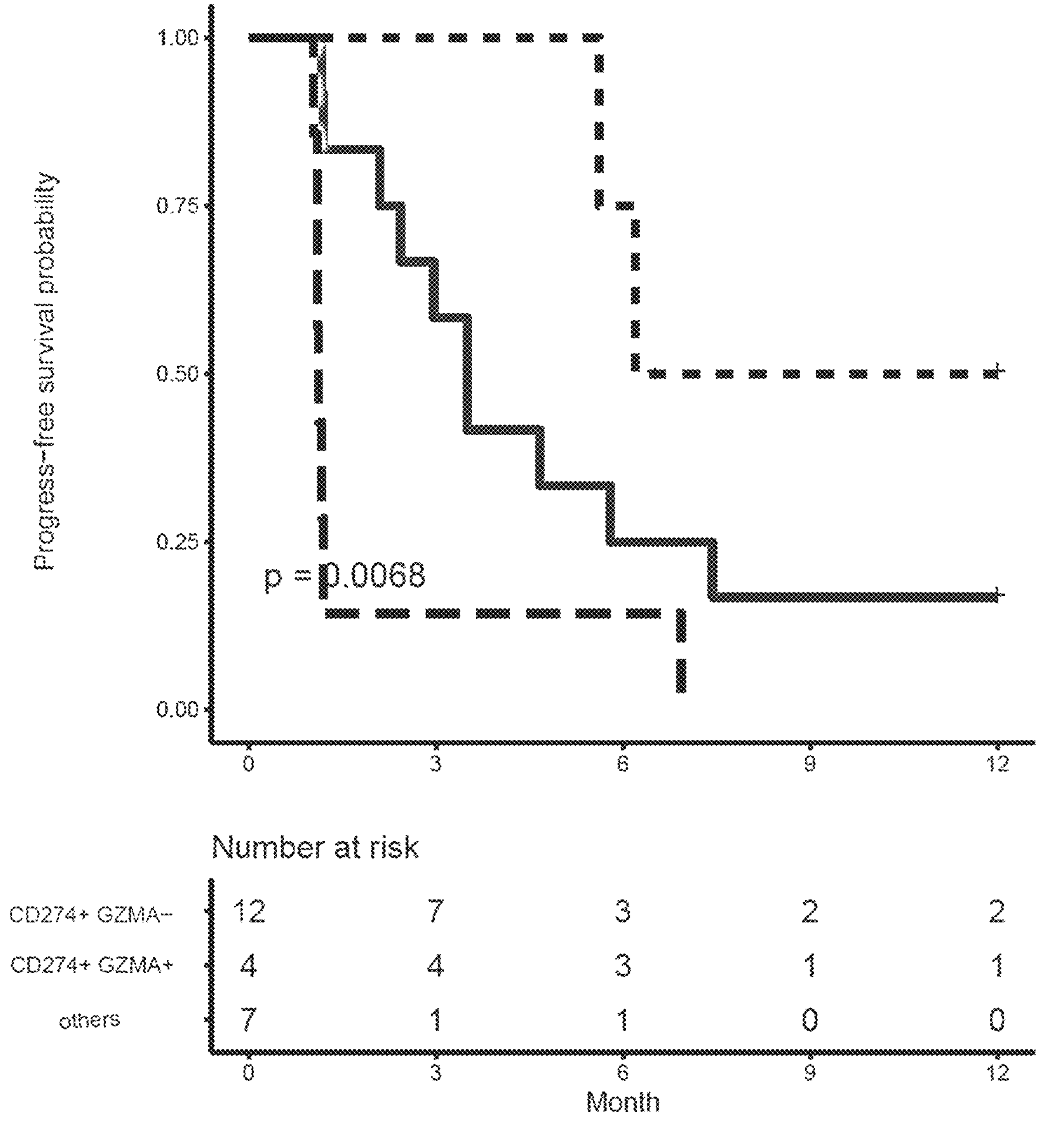
FIG. 5*a* shows Kaplan-Meier curves for progression-free survival of NSCLC patients, after receiving immune-checkpoint inhibitor therapy, with RNA expression by the Alpha-RNA method showing CD274 high expression and GZMA low expression (n=12), CD274 high expression and GZMA high expression (n=4) and CD274 low expression (n=7)
Figure 5B:
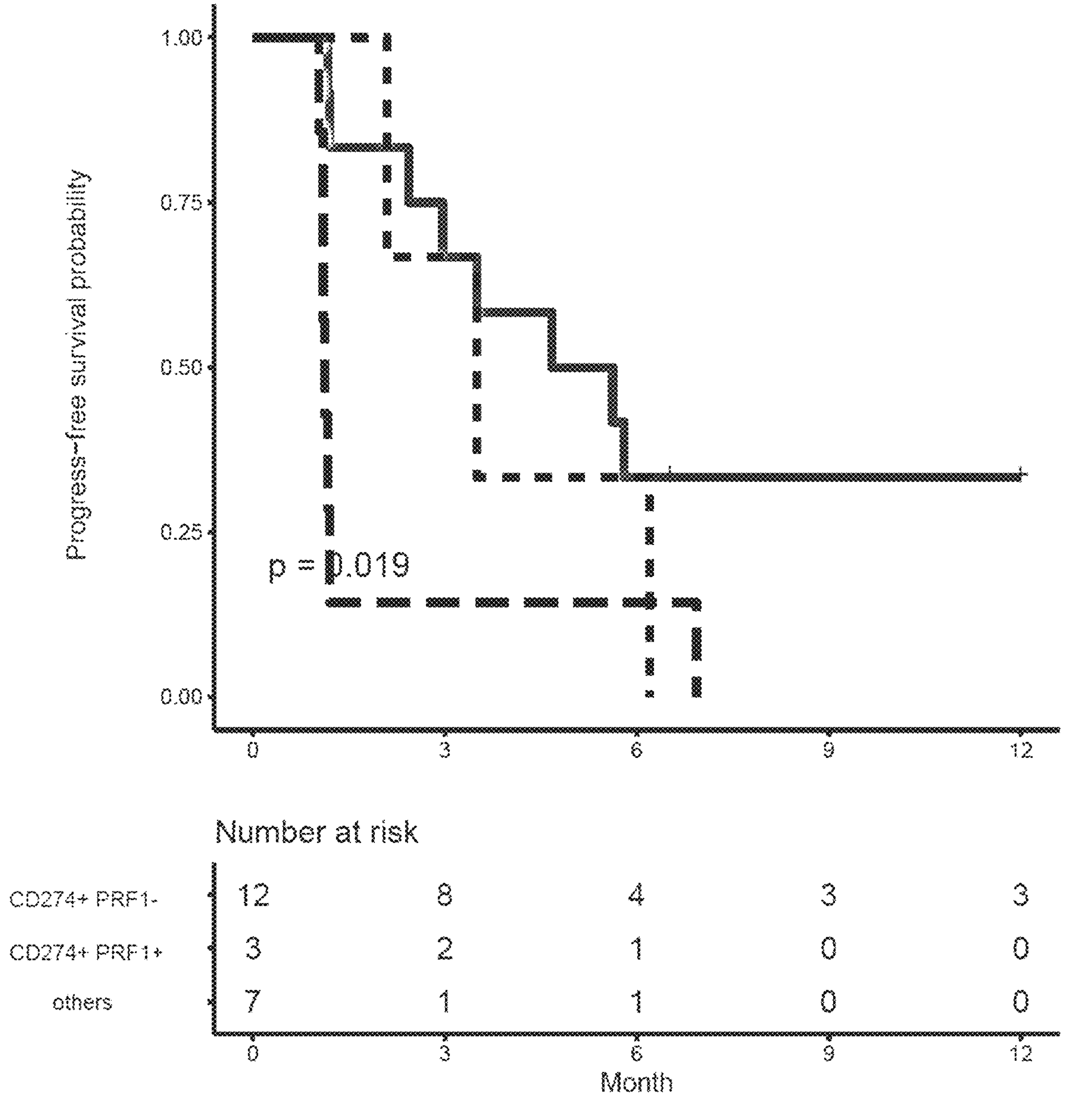
FIG. 5*b* shows Kaplan-Meier curves for survival of NSCLC patients, after receiving immune-checkpoint inhibitor therapy, with RNA expression by the Alpha-RNA method showing CD274 high expression and PRF1 low expression (n=12), CD274 high expression and PRF1 high expression (n=3) and CD274 low expression (n=7).

Investigate the Predictive Role of GZMA, PRF1, and CD274 in Immune Checkpoint Blockade Therapy in NSCLC Patients The success of anti-PD1/anti-PD-L1 therapy depends largely on the immune state of an individual. Thus, the inventors wonder whether the status of $CD8^+$ T cells and the expression of its suppression ligand PD-L1 could predict the NSCLC patient response to anti-PD-1/PD-L1 therapies. This example have included 38 patients who have received the therapies and have available biopsies taken prior to the treatments, and with follow-up on treatment outcomes (stable disease [SD], partial response [PR] and complete response [PD]). We will use the method described before to quantify the expression of granzyme A, perforin, PD1 and PD-L1 (with isoforms). The expression of these genes is normalized by housekeeping genes (CHAMP and B2M). Progression Free Survival (PFS) is analyzed by CD8 signature genes and CD274 to investigate the predictive role of GZMA, PRF1, and CD274 isoforms in anti-PD-1/PD-L1 treatment outcomes in NSCLC patients. Survival analysis shows that GZA and CD274 double positive patients have the best PFS when they are treated with ICIs (FIG. 5*a*), but another CD8 signature gene PRF1 combined with CD274 does not improve PFS (FIG. 5*b*).

Discussion

Without intending to be bound by theory, it is believed that PD-L1 is broadly expressed in NSCLC patients, both in adenocarcinoma and squamous cell carcinoma. The expression of inhibitory molecule PD-L1 and high infiltration of T cells in tumor microenvironment indicate that those exhausted T cells may be the reason for tumor escaping. Immune checkpoint inhibitors against PD-1/PD-L1 axis has produced huge clinical benefit, but the method to discriminate ICIs-responders and non-responders is poorly developed.

The present invention identifies one novel transcript of PD-L1, which has high expression of exon6 and low expression of exon4. One publication has reported highly secreted PD-L1 in Adult T-cell leukemia (ATL) patient, about 27% ATL has this sPD-L1 variant. In the examples herein, eight of 155 NSCLC patients have ex6+ ex4− transcript, which is consistent with previous publication. Patients with ex6+ ex4− transcript have poor survival than others, but univariate and multivariate. Cox regression shows that the novel transcript of this invention does not increase hazard (HR>1, but p value >0.05), more samples are needed to elucidate the function of ex6+ ex4− transcript.

To validate the predictive function of PD-L1 and other immune factors, the inventors use cohort II which contains 33 patients who fails first-line therapies and further receives anti-PD-1 therapies, prior to which needle biopsies are obtained. The result proves that patients with high expression of CD274 and low expression of GZMA have the best response to ICIs, which suggests that combination of CD274 and GZMA has the potential to be predictive marker for ICIs therapy.

Although, responders could be identified with this method, it is believed that some patients could still develop resistance to ICIs. Many genetic and epigenetic mechanisms enable the acquired resistance to ICIs therapy[21]. Downregulation of HLA class I molecules and loss of (B2M) expression have been described in melanoma patients treated with PD-1 blockade[22]. The loss of B2M results in impaired cell surface expression of MHC class I and defective antigen presentation, which mediates the resistance to ICI therapy. With the method according to the invention, one could adjust the primer panel and monitor the immune status of patients and combine ICI and chemotherapy, which could release more tumor antigens and generate adequate anti-tumor T cells. Despite this, it is believed that expression of alternative co-inhibitory immune checkpoints (e.g., CTLA-4, TIM-3, LAG-3, and VISTA) has been associated with resistance to ICIs[23], thus to improve the method, primer panels need to be enlarged.

1. Gandhi L, Rodriguez-Abreu D, Gadgeel S, et al. Pembrolizumab plus Chemotherapy in Metastatic Non-Small-Cell Lung Cancer. *N Engl J Med.* 2018; 378(22):2078-2092. doi:10.1056/NEJMoa1801005
2. Chiang A C, Herbst R S. Frontline immunotherapy for NSCLC—the tale of the tail. *Nat Rev Clin Oncol.* 2020; 17(2):73-74. doi:10.1038/s41571-019-0317-y
3. Garon E B, Rizvi N A, Hui R, et al. Pembrolizumab for the Treatment of Non-Small-Cell Lung Cancer. *N Engl J Med.* 2015; 372(21):2018-2028. doi:10.1056/nejmoa1501824
4. Gettinger S N, Shepherd F A, Antonia S J, et al. First-line nivolumab (anti-PD-1; BMS-936558, ONO-4538) monotherapy in advanced NSCLC: Safety, efficacy, and correlation of outcomes with PD-L1 status. *J Clin Oncol.* 2014; 32(15_suppl):8024-8024. doi:10.1200/jco.2014.32.15_suppl.8024
5. Bodor J N, Boumber Y, Borghaei H. Biomarkers for immune checkpoint inhibition in non-small cell lung cancer (NSCLC). *Cancer.* 2020; 126(2):260-270. doi:10.1002/cncr.32468
6. Mok TSK, Wu Y-L, Kudaba I, et al. Pembrolizumab versus chemotherapy for previously untreated, PD-L1-expressing, locally advanced or metastatic non-small-cell lung cancer (KEYNOTE-042): a randomised, open-label, controlled, phase 3 trial. *Lancet.* 2019; 393(10183):1819-1830. doi:10.1016/S0140-6736(18)32409-7

7. Kintsler S, Cassataro M A, Drosch M, Holenya P, Knuechel R, Braunschweig T. Expression of programmed death ligand (PD-L1) in different tumors. Comparison of several current available antibody clones and antibody profiling. *Ann Diagn Pathol.* 2019; 41:24-37. doi: 10.1016/J.ANNDIAGPATH.2019.05.005
8. Hirsch F R, McElhinny A, Stanforth D, et al. PD-L1 Immunohistochemistry Assays for Lung Cancer: Results from Phase 1 of the Blueprint PD-L1 IHC Assay Comparison Project. *J Thorac Oncol.* 2017; 12(2):208-222. doi:10.1016/J.JTHO.2016.11.2228
9. Lawson N L, Dix C I, Scorer P W, et al. Mapping the binding sites of antibodies utilized in programmed cell death ligand-1 predictive immunohistochemical assays for use with immuno-oncology therapies. *Mod Pathol.* 2020; 33(4):518-530. doi:10.1038/s41379-019-0372-z
10. Jiang Y, Li Y, Zhu B. T-cell exhaustion in the tumor microenvironment. *Cell Death Dis.* 2015; 6(6):e1792-e1792. doi:10.1038/cddis.2015.162
11. Zhang D, He W, Wu C, et al. Scoring system for tumor-infiltrating lymphocytes and its prognostic value for gastric cancer. *Front Immunol.* 2019; 10(JAN):71. doi:10.3389/fimmu.2019.00071
12. Tokito T, Azuma K, Kawahara A, et al. Predictive relevance of PD-L1 expression combined with CD8+ TIL density in stage III non-small cell lung cancer patients receiving concurrent chemoradiotherapy. *Eur J Cancer.* 2016; 55:7-14. doi:10.1016/j.ejca.2015.11.020
13. Fumet J-D, Richard C, Ledys F, et al. Prognostic and predictive role of CD8 and PD-L1 determination in lung tumor tissue of patients under anti-PD-1 therapy. *Br J Cancer.* 2018; 119(8):950-960. doi:10.1038/s41416-018-0220-9
14. Blank C U, Haining W N, Held W, et al. Defining 'T cell exhaustion.' *Nat Rev Immunol.* 2019; 19(11):665-674. doi:10.1038/s41577-019-0221-9
15. Wucherpfennig K W, Shirley Liu X, Jiang P, et al. Signatures of T cell dysfunction and exclusion predict cancer immunotherapy response. *Nat Med.* doi:10.1038/s41591-018-0136-1
16. Kataoka K, Shiraishi Y, Takeda Y, et al. Aberrant PD-L1 expression through 3'-UTR disruption in multiple cancers. *Nature.* 2016; 534(7607):402-406. doi:10.1038/nature18294
17. Gong B, Kiyotani K, Sakata S, et al. Secreted PD-L1 variants mediate resistance to PD-L1 blockade therapy in non-small cell lung cancer. *J Exp Med.* 2019; 216(4):982-1000. doi:10.1084/jem.20180870
18. Castello A, Rossi S, Toschi L, Mansi L, Lopci E. Soluble PD-L1 in NSCLC patients treated with checkpoint inhibitors and its correlation with metabolic parameters. *Cancers (Basel).* 2020; 12(6):1373. doi:10.3390/cancers12061373
19. Meyo M T, Jouinot A, Giroux-Leprieur E, et al. Predictive value of soluble PD-1, PD-L1, VEGFA, CD40 ligand and CD44 for nivolumab therapy in advanced non-small cell lung cancer: A case-control study. *Cancers (Basel).* 2020; 12(2):473. doi:10.3390/cancers12020473
20. Zheng Z, Liebers M, Zhelyazkova B, et al. Anchored multiplex PCR for targeted next-generation sequencing. *Nat Med.* 2014; 20(12):1479-1484. doi:10.1038/nm.3729
21. Jenkins R W, Barbie D A, Flaherty K T. Mechanisms of resistance to immune checkpoint inhibitors. *Br J Cancer.* 2018; 118(1):9-16. doi:10.1038/bjc.2017.434
22. Zaretsky J M, Garcia-Diaz A, Shin D S, et al. Mutations Associated with Acquired Resistance to PD-1 Blockade in Melanoma. *N Engl J Med.* 2016; 375(9):819-829. doi: 10.1056/nejmoa1604958
23. Thommen D S, Schreiner J, Müller P, et al. Progression of lung cancer is associated with increased dysfunction of T cells defined by coexpression of multiple inhibitory receptors. *Cancer Immunol Res.* 2015; 3(12):1344-1354. doi:10.1158/2326-6066.CIR-15-0097

It should be understood that the above only illustrates and describes examples whereby the present invention may be carried out, and that modifications and/or alterations may be made thereto without departing from the spirit of the invention.

It should also be understood that certain features of the invention, which are, for clarity, described in the context of separate embodiments, may also be provided in combination in a single embodiment. Conversely, various features of the invention which are, for brevity, described in the context of a single embodiment, may also be provided separately, or in any suitable subcombination.

All references specifically cited herein are hereby incorporated by reference in their entireties. However, the citation or incorporation of such a reference is not necessarily an admission as to its appropriateness, citability, and/or availability as prior art to/against the present invention.

What is claimed is:

1. A method of measuring RNA expression level of a target sequence in a sample by simultaneously enriching the target sequence and corresponding RNA and calculating a RNA-to-DNA ratio of the same target sequence, comprising the steps of:

(a) reverse transcribing RNA into complementary DNA (cDNA) resulting in a mixture of cDNA and genomic DNA (gDNA);

(b) ligating a universal sequencing adaptor to a terminal of the gDNA and cDNA from step (a);

(c) conducting a first polymerase chain reaction process to produce a single-stranded primer extension product comprising a complementary sequence, wherein the complementary sequence is complementary to the target sequence on the gDNA, the cDNA, or a combination thereof, and is complementary to the universal sequencing adaptor;

(d) conducting a second polymerase chain reaction process to amplify the single-stranded primer extension product; and (e) performing a next-generation sequencing process and calculating the relative ratio of cDNA sequencing reads to gDNA sequencing reads, namely the RNA-to-DNA ratio, of the same target sequence, wherein the target sequence is selected from a group consisting of a gene sequence, an exon of a gene, and a combination thereof;

wherein the first polymerase chain reaction process comprises the steps of:

(i) contacting a first primer that binds to the cDNA and gDNA sequence at a position that is 3' in relation to the target sequence on the cDNA or gDNA;

(ii) extending by polymerization the first primer till the terminal comprising the ligated universal sequencing adaptor to produce the single-stranded primer extension product;

(iii) dissociating the single-stranded primer extension product comprising the complementary sequence to the target sequence from the template strand cDNA or gDNA; and (iv) optionally, repeating steps (i) through (iii) one or more times;

wherein the first primer has a sequence selected from the group consisting of SEQ ID NOs. 1-379, and analogues thereof with an identity of at least 80% of any one of SEQ ID NOs. 1-379.

2. The method of claim 1, wherein the second polymerase chain reaction process comprises binding a second primer to the target sequence at a position that is between the first primer and the target sequence on the cDNA or gDNA.

3. The method of claim 2, wherein the second primer is used to prime and enrich both gDNA and cDNA.

4. The method of claim 2, wherein the second primer has a sequence selected from the group consisting of SEQ ID NOs. 380-758, and analogues thereof with an identity of at least 80% of any one of SEQ ID NOs. 380-758.

5. The method of claim 1, wherein steps (i) through (iii) are repeated for from about 1 cycles to about 100 cycles.

6. The method of claim 1, wherein the sample is selected from the group consisting of a formalin-fix paraffin-embedded tissue, fresh tissue collected by surgical biopsy or needle aspiration, blood, urine, ascites, pleural effusion, cerebrospinal fluid, pancreas cyst fluid, and a combination thereof.

7. The method of claim 1, wherein the method is for quantifying the expression of the target sequence selected from the group consisting of genes related to immune microenvironment, oncogenes, tumor suppressor genes, housekeeping genes, and other disease relevant genes.

8. The method of claim 1, wherein total nucleic acid is used to perform the reverse transcription in step (a) without removing genomic DNA.

9. A method of treating cancer in a subject comprising the steps of:

a. testing the subject for RNA expression level of a target sequence according to the method of claim 1; and b. applying an immune checkpoint inhibitor to the subject.

10. The method of claim 9, wherein the subject has high expression of CD274 and low expression of GZMA, wherein a high expression level is defined as an RNA expression level above the $20^{th}$ percentile cutoff value, and a low expression level is defined as an RNA expression level equal to or below the $20^{th}$ percentile cutoff value, wherein the cutoff value is determined using RNA expression levels among all the subject group.

11. The method of claim 10, wherein the subject has high expression of CD274 at single exon level.

12. The method of claim 9, wherein the cancer is non-small cell lung cancer.

13. The method of claim 12, wherein the non-small cell lung cancer is selected from the group consisting of adenocarcinoma, squamous cell carcinoma, large-cell lung carcinoma and a combination thereof.

14. The method of claim 9, wherein the immune checkpoint inhibitor is selected from the group consisting of a PD-1 inhibitor, a PD-L1 inhibitor, and a combination thereof.

15. The method of claim 9, wherein the immune checkpoint inhibitor is selected from the group consisting of pembrolizumab, nivolumab, atezolizumab, durvalumab, and a combination thereof.

16. A kit for performing the method of measuring RNA expression level of a target sequence in a sample by simultaneously enriching a target DNA and corresponding RNA and calculating a RNA-to-DNA ratio of the same target sequence according to claim 1, the kit comprising:

(a) a reverse transcriptase for transcribing RNA into complementary DNA (cDNA);

(b) a universal sequencing adaptor to be ligated to a terminal of gDNA and cDNA in the sample;

(c) a first primer that binds to the cDNA and gDNA sequence at a position that is 3' in relation to the target sequence on the cDNA or gDNA; and (d) a second primer that binds to the target sequence at a position that is between the first primer and the target sequence on the cDNA or gDNA;

wherein the the first primer has a sequence selected from the group consisting of SEQ ID NOs. 1-379, and analogues thereof with an identity of at least 80% of any one of SEQ ID NOs. 1-379.

17. The kit of claim 16, wherein the second primer has a sequence selected from the group consisting of SEQ ID NOs. 380-758, and analogues thereof with an identity of at least 80% of any one of SEQ ID NOs. 380-758.

* * * * *

SEQUENCE LISTING

```
Sequence total quantity: 758
SEQ ID NO: 1            moltype = DNA  length = 44
FEATURE                 Location/Qualifiers
source                  1..44
                        mol_type = other DNA
                        organism = synthetic construct
SEQUENCE: 1
ttagggataa cagggtaatc agatatcgat ctgttagaaa cctc                   44

SEQ ID NO: 2            moltype = DNA  length = 46
FEATURE                 Location/Qualifiers
source                  1..46
                        mol_type = other DNA
                        organism = synthetic construct
SEQUENCE: 2
ttagggataa cagggtaatc agctgctgaa aatgtaactt tgtatc                 46

SEQ ID NO: 3            moltype = DNA  length = 42
FEATURE                 Location/Qualifiers
source                  1..42
                        mol_type = other DNA
```

-continued

```
                        organism = synthetic construct
SEQUENCE: 3
ttagggataa cagggtaatc ggccgttgta cactcatctt cc                      42

SEQ ID NO: 4            moltype = DNA  length = 41
FEATURE                 Location/Qualifiers
source                  1..41
                        mol_type = other DNA
                        organism = synthetic construct
SEQUENCE: 4
ttagggataa cagggtaatc cacaaaatgg atccagacaa c                       41

SEQ ID NO: 5            moltype = DNA  length = 42
FEATURE                 Location/Qualifiers
source                  1..42
                        mol_type = other DNA
                        organism = synthetic construct
SEQUENCE: 5
ttagggataa cagggtaatc taatgcttgc tctgatagga aa                      42

SEQ ID NO: 6            moltype = DNA  length = 41
FEATURE                 Location/Qualifiers
source                  1..41
                        mol_type = other DNA
                        organism = synthetic construct
SEQUENCE: 6
ttagggataa cagggtaatc ttacacccag tggagaagct c                       41

SEQ ID NO: 7            moltype = DNA  length = 40
FEATURE                 Location/Qualifiers
source                  1..40
                        mol_type = other DNA
                        organism = synthetic construct
SEQUENCE: 7
ttagggataa cagggtaatc cccaccagac catgagaggc                         40

SEQ ID NO: 8            moltype = DNA  length = 42
FEATURE                 Location/Qualifiers
source                  1..42
                        mol_type = other DNA
                        organism = synthetic construct
SEQUENCE: 8
ttagggataa cagggtaatc cagttaacgt cttccttctc tc                      42

SEQ ID NO: 9            moltype = DNA  length = 40
FEATURE                 Location/Qualifiers
source                  1..40
                        mol_type = other DNA
                        organism = synthetic construct
SEQUENCE: 9
ttagggataa cagggtaatc ggacccccac acagcaaagc                         40

SEQ ID NO: 10           moltype = DNA  length = 40
FEATURE                 Location/Qualifiers
source                  1..40
                        mol_type = other DNA
                        organism = synthetic construct
SEQUENCE: 10
ttagggataa cagggtaatc ccctccttct ggccaccatg                         40

SEQ ID NO: 11           moltype = DNA  length = 41
FEATURE                 Location/Qualifiers
source                  1..41
                        mol_type = other DNA
                        organism = synthetic construct
SEQUENCE: 11
ttagggataa cagggtaatc ctgggagcca atattgtctt t                       41

SEQ ID NO: 12           moltype = DNA  length = 41
FEATURE                 Location/Qualifiers
source                  1..41
                        mol_type = other DNA
                        organism = synthetic construct
SEQUENCE: 12
ttagggataa cagggtaatc gaacgtactg gtgaaaacac c                       41

SEQ ID NO: 13           moltype = DNA  length = 40
FEATURE                 Location/Qualifiers
source                  1..40
```

```
                        mol_type = other DNA
                        organism = synthetic construct
SEQUENCE: 13
ttagggataa cagggtaatc tcaggaaaat gctggctgac                        40

SEQ ID NO: 14           moltype = DNA  length = 40
FEATURE                 Location/Qualifiers
source                  1..40
                        mol_type = other DNA
                        organism = synthetic construct
SEQUENCE: 14
ttagggataa cagggtaatc ggtatgtggc tacatgttcc                        40

SEQ ID NO: 15           moltype = DNA  length = 41
FEATURE                 Location/Qualifiers
source                  1..41
                        mol_type = other DNA
                        organism = synthetic construct
SEQUENCE: 15
ttagggataa cagggtaatc ctgaggaagg ataggacagg g                      41

SEQ ID NO: 16           moltype = DNA  length = 42
FEATURE                 Location/Qualifiers
source                  1..42
                        mol_type = other DNA
                        organism = synthetic construct
SEQUENCE: 16
ttagggataa cagggtaatc cccataccct ctcagcgtac cc                     42

SEQ ID NO: 17           moltype = DNA  length = 41
FEATURE                 Location/Qualifiers
source                  1..41
                        mol_type = other DNA
                        organism = synthetic construct
SEQUENCE: 17
ttagggataa cagggtaatc ataggggttt gctccggaga g                      41

SEQ ID NO: 18           moltype = DNA  length = 41
FEATURE                 Location/Qualifiers
source                  1..41
                        mol_type = other DNA
                        organism = synthetic construct
SEQUENCE: 18
ttagggataa cagggtaatc tgttggatca tattcgtcca c                      41

SEQ ID NO: 19           moltype = DNA  length = 45
FEATURE                 Location/Qualifiers
source                  1..45
                        mol_type = other DNA
                        organism = synthetic construct
SEQUENCE: 19
ttagggataa cagggtaatc tttattataa ggcctgctga aaatg                  45

SEQ ID NO: 20           moltype = DNA  length = 40
FEATURE                 Location/Qualifiers
source                  1..40
                        mol_type = other DNA
                        organism = synthetic construct
SEQUENCE: 20
ttagggataa cagggtaatc aaagaaagcc ctccccagtc                        40

SEQ ID NO: 21           moltype = DNA  length = 44
FEATURE                 Location/Qualifiers
source                  1..44
                        mol_type = other DNA
                        organism = synthetic construct
SEQUENCE: 21
ttagggataa cagggtaatc cctacaggaa gcaagtagta attg                   44

SEQ ID NO: 22           moltype = DNA  length = 40
FEATURE                 Location/Qualifiers
source                  1..40
                        mol_type = other DNA
                        organism = synthetic construct
SEQUENCE: 22
ttagggataa cagggtaatc tgagttctgg gcactgggtc                        40

SEQ ID NO: 23           moltype = DNA  length = 41
FEATURE                 Location/Qualifiers
```

-continued

```
source                1..41
                      mol_type = other DNA
                      organism = synthetic construct
SEQUENCE: 23
ttagggataa cagggtaatc cacaacccac tgaggtatat g                     41

SEQ ID NO: 24         moltype = DNA  length = 42
FEATURE               Location/Qualifiers
source                1..42
                      mol_type = other DNA
                      organism = synthetic construct
SEQUENCE: 24
ttagggataa cagggtaatc taaatgttac gcagtgctaa cc                    42

SEQ ID NO: 25         moltype = DNA  length = 44
FEATURE               Location/Qualifiers
source                1..44
                      mol_type = other DNA
                      organism = synthetic construct
SEQUENCE: 25
ttagggataa cagggtaatc gttgcaaacc acaaaagtat actc                  44

SEQ ID NO: 26         moltype = DNA  length = 41
FEATURE               Location/Qualifiers
source                1..41
                      mol_type = other DNA
                      organism = synthetic construct
SEQUENCE: 26
ttagggataa cagggtaatc gtcctttctg taggctggat g                     41

SEQ ID NO: 27         moltype = DNA  length = 42
FEATURE               Location/Qualifiers
source                1..42
                      mol_type = other DNA
                      organism = synthetic construct
SEQUENCE: 27
ttagggataa cagggtaatc catctgactt ggtggtaaac tt                    42

SEQ ID NO: 28         moltype = DNA  length = 42
FEATURE               Location/Qualifiers
source                1..42
                      mol_type = other DNA
                      organism = synthetic construct
SEQUENCE: 28
ttagggataa cagggtaatc ggaaaatgac aaagaacagc tc                    42

SEQ ID NO: 29         moltype = DNA  length = 41
FEATURE               Location/Qualifiers
source                1..41
                      mol_type = other DNA
                      organism = synthetic construct
SEQUENCE: 29
ttagggataa cagggtaatc ccattttagc acttacctgt g                     41

SEQ ID NO: 30         moltype = DNA  length = 42
FEATURE               Location/Qualifiers
source                1..42
                      mol_type = other DNA
                      organism = synthetic construct
SEQUENCE: 30
ttagggataa cagggtaatc tgacattgca tacattcgaa ag                    42

SEQ ID NO: 31         moltype = DNA  length = 46
FEATURE               Location/Qualifiers
source                1..46
                      mol_type = other DNA
                      organism = synthetic construct
SEQUENCE: 31
ttagggataa cagggtaatc attatgaaac caatattatg gatccc                46

SEQ ID NO: 32         moltype = DNA  length = 41
FEATURE               Location/Qualifiers
source                1..41
                      mol_type = other DNA
                      organism = synthetic construct
SEQUENCE: 32
ttagggataa cagggtaatc gactcctgct tctgtcatat c                     41

SEQ ID NO: 33         moltype = DNA  length = 40
```

-continued

```
FEATURE                Location/Qualifiers
source                 1..40
                       mol_type = other DNA
                       organism = synthetic construct
SEQUENCE: 33
ttagggataa cagggtaatc gagaggatca gcgagagtgg                    40

SEQ ID NO: 34          moltype = DNA  length = 40
FEATURE                Location/Qualifiers
source                 1..40
                       mol_type = other DNA
                       organism = synthetic construct
SEQUENCE: 34
ttagggataa cagggtaatc acctggcctt catacacctc                    40

SEQ ID NO: 35          moltype = DNA  length = 40
FEATURE                Location/Qualifiers
source                 1..40
                       mol_type = other DNA
                       organism = synthetic construct
SEQUENCE: 35
ttagggataa cagggtaatc gtcagtgggg ctgcggcatg                    40

SEQ ID NO: 36          moltype = DNA  length = 43
FEATURE                Location/Qualifiers
source                 1..43
                       mol_type = other DNA
                       organism = synthetic construct
SEQUENCE: 36
ttagggataa cagggtaatc caatttcttg cagaacacac agc                43

SEQ ID NO: 37          moltype = DNA  length = 40
FEATURE                Location/Qualifiers
source                 1..40
                       mol_type = other DNA
                       organism = synthetic construct
SEQUENCE: 37
ttagggataa cagggtaatc ttttccaagg acggttgaag                    40

SEQ ID NO: 38          moltype = DNA  length = 40
FEATURE                Location/Qualifiers
source                 1..40
                       mol_type = other DNA
                       organism = synthetic construct
SEQUENCE: 38
ttagggataa cagggtaatc cgaaggacta gtttggaacc                    40

SEQ ID NO: 39          moltype = DNA  length = 42
FEATURE                Location/Qualifiers
source                 1..42
                       mol_type = other DNA
                       organism = synthetic construct
SEQUENCE: 39
ttagggataa cagggtaatc acatatactc tccagaatca gc                 42

SEQ ID NO: 40          moltype = DNA  length = 41
FEATURE                Location/Qualifiers
source                 1..41
                       mol_type = other DNA
                       organism = synthetic construct
SEQUENCE: 40
ttagggataa cagggtaatc tgaagacaca tatgctcctt c                  41

SEQ ID NO: 41          moltype = DNA  length = 40
FEATURE                Location/Qualifiers
source                 1..40
                       mol_type = other DNA
                       organism = synthetic construct
SEQUENCE: 41
ttagggataa cagggtaatc tccttctccg cacattttac                    40

SEQ ID NO: 42          moltype = DNA  length = 40
FEATURE                Location/Qualifiers
source                 1..40
                       mol_type = other DNA
                       organism = synthetic construct
SEQUENCE: 42
ttagggataa cagggtaatc gcatctccac cgccgtgtgc                    40
```

```
SEQ ID NO: 43          moltype = DNA  length = 41
FEATURE                Location/Qualifiers
source                 1..41
                       mol_type = other DNA
                       organism = synthetic construct
SEQUENCE: 43
ttagggataa cagggtaatc tcttctccac cgggtctcca g                    41

SEQ ID NO: 44          moltype = DNA  length = 42
FEATURE                Location/Qualifiers
source                 1..42
                       mol_type = other DNA
                       organism = synthetic construct
SEQUENCE: 44
ttagggataa cagggtaatc gcacaaggag cagcgtagaa ag                   42

SEQ ID NO: 45          moltype = DNA  length = 40
FEATURE                Location/Qualifiers
source                 1..40
                       mol_type = other DNA
                       organism = synthetic construct
SEQUENCE: 45
ttagggataa cagggtaatc gggagctgcc acccaatgtc                      40

SEQ ID NO: 46          moltype = DNA  length = 40
FEATURE                Location/Qualifiers
source                 1..40
                       mol_type = other DNA
                       organism = synthetic construct
SEQUENCE: 46
ttagggataa cagggtaatc tctgaggttg gagattcgag                      40

SEQ ID NO: 47          moltype = DNA  length = 41
FEATURE                Location/Qualifiers
source                 1..41
                       mol_type = other DNA
                       organism = synthetic construct
SEQUENCE: 47
ttagggataa cagggtaatc ggtgtccccg atgtcattcg c                    41

SEQ ID NO: 48          moltype = DNA  length = 41
FEATURE                Location/Qualifiers
source                 1..41
                       mol_type = other DNA
                       organism = synthetic construct
SEQUENCE: 48
ttagggataa cagggtaatc tcccaccaca gacgcaatca c                    41

SEQ ID NO: 49          moltype = DNA  length = 43
FEATURE                Location/Qualifiers
source                 1..43
                       mol_type = other DNA
                       organism = synthetic construct
SEQUENCE: 49
ttagggataa cagggtaatc ttgtcttgat tttactttcc caa                  43

SEQ ID NO: 50          moltype = DNA  length = 40
FEATURE                Location/Qualifiers
source                 1..40
                       mol_type = other DNA
                       organism = synthetic construct
SEQUENCE: 50
ttagggataa cagggtaatc tggcagagtc atcatcattg                      40

SEQ ID NO: 51          moltype = DNA  length = 40
FEATURE                Location/Qualifiers
source                 1..40
                       mol_type = other DNA
                       organism = synthetic construct
SEQUENCE: 51
ttagggataa cagggtaatc acaggcaaaa gcagcaagtc                      40

SEQ ID NO: 52          moltype = DNA  length = 43
FEATURE                Location/Qualifiers
source                 1..43
                       mol_type = other DNA
                       organism = synthetic construct
SEQUENCE: 52
ttagggataa cagggtaatc gctggctgag tcctcctcac cac                  43
```

```
SEQ ID NO: 53           moltype = DNA  length = 40
FEATURE                 Location/Qualifiers
source                  1..40
                        mol_type = other DNA
                        organism = synthetic construct
SEQUENCE: 53
ttagggataa cagggtaatc tcagcacgat gtctctcctc                        40

SEQ ID NO: 54           moltype = DNA  length = 40
FEATURE                 Location/Qualifiers
source                  1..40
                        mol_type = other DNA
                        organism = synthetic construct
SEQUENCE: 54
ttagggataa cagggtaatc ggctccccag gctcgtgtcc                        40

SEQ ID NO: 55           moltype = DNA  length = 44
FEATURE                 Location/Qualifiers
source                  1..44
                        mol_type = other DNA
                        organism = synthetic construct
SEQUENCE: 55
ttagggataa cagggtaatc cttcaggacg ttgaactctg acag                   44

SEQ ID NO: 56           moltype = DNA  length = 40
FEATURE                 Location/Qualifiers
source                  1..40
                        mol_type = other DNA
                        organism = synthetic construct
SEQUENCE: 56
ttagggataa cagggtaatc aggaccttgg ctgcatgaag                        40

SEQ ID NO: 57           moltype = DNA  length = 41
FEATURE                 Location/Qualifiers
source                  1..41
                        mol_type = other DNA
                        organism = synthetic construct
SEQUENCE: 57
ttagggataa cagggtaatc tagtaatttg ggaatgcctg g                      41

SEQ ID NO: 58           moltype = DNA  length = 44
FEATURE                 Location/Qualifiers
source                  1..44
                        mol_type = other DNA
                        organism = synthetic construct
SEQUENCE: 58
ttagggataa cagggtaatc ctgcaggatc cattaaatgt catc                   44

SEQ ID NO: 59           moltype = DNA  length = 41
FEATURE                 Location/Qualifiers
source                  1..41
                        mol_type = other DNA
                        organism = synthetic construct
SEQUENCE: 59
ttagggataa cagggtaatc ggcaggaaga ttttcaatct c                      41

SEQ ID NO: 60           moltype = DNA  length = 45
FEATURE                 Location/Qualifiers
source                  1..45
                        mol_type = other DNA
                        organism = synthetic construct
SEQUENCE: 60
ttagggataa cagggtaatc tcaagtttaa tatcccatga ttgtc                  45

SEQ ID NO: 61           moltype = DNA  length = 42
FEATURE                 Location/Qualifiers
source                  1..42
                        mol_type = other DNA
                        organism = synthetic construct
SEQUENCE: 61
ttagggataa cagggtaatc atgtgacatt cgtctacctc ac                     42

SEQ ID NO: 62           moltype = DNA  length = 40
FEATURE                 Location/Qualifiers
source                  1..40
                        mol_type = other DNA
                        organism = synthetic construct
SEQUENCE: 62
```

```
ttagggataa cagggtaatc cgacgaggtg gcctgtcgtc                        40

SEQ ID NO: 63           moltype = DNA  length = 41
FEATURE                 Location/Qualifiers
source                  1..41
                        mol_type = other DNA
                        organism = synthetic construct
SEQUENCE: 63
ttagggataa cagggtaatc tcctccatct catagctgtc g                      41

SEQ ID NO: 64           moltype = DNA  length = 46
FEATURE                 Location/Qualifiers
source                  1..46
                        mol_type = other DNA
                        organism = synthetic construct
SEQUENCE: 64
ttagggataa cagggtaatc gagtgagtct ttaaattcac caatac                 46

SEQ ID NO: 65           moltype = DNA  length = 41
FEATURE                 Location/Qualifiers
source                  1..41
                        mol_type = other DNA
                        organism = synthetic construct
SEQUENCE: 65
ttagggataa cagggtaatc gcggggagaa ctggggtgct g                      41

SEQ ID NO: 66           moltype = DNA  length = 41
FEATURE                 Location/Qualifiers
source                  1..41
                        mol_type = other DNA
                        organism = synthetic construct
SEQUENCE: 66
ttagggataa cagggtaatc atccaaatga ggagtgtgta c                      41

SEQ ID NO: 67           moltype = DNA  length = 45
FEATURE                 Location/Qualifiers
source                  1..45
                        mol_type = other DNA
                        organism = synthetic construct
SEQUENCE: 67
ttagggataa cagggtaatc gtaatggact ggatatatca gagtc                  45

SEQ ID NO: 68           moltype = DNA  length = 46
FEATURE                 Location/Qualifiers
source                  1..46
                        mol_type = other DNA
                        organism = synthetic construct
SEQUENCE: 68
ttagggataa cagggtaatc actcctcgcc ggctcttttt caattg                 46

SEQ ID NO: 69           moltype = DNA  length = 40
FEATURE                 Location/Qualifiers
source                  1..40
                        mol_type = other DNA
                        organism = synthetic construct
SEQUENCE: 69
ttagggataa cagggtaatc cagcatggtg agcagctcag                        40

SEQ ID NO: 70           moltype = DNA  length = 40
FEATURE                 Location/Qualifiers
source                  1..40
                        mol_type = other DNA
                        organism = synthetic construct
SEQUENCE: 70
ttagggataa cagggtaatc cctggagcca catcctcccc                        40

SEQ ID NO: 71           moltype = DNA  length = 44
FEATURE                 Location/Qualifiers
source                  1..44
                        mol_type = other DNA
                        organism = synthetic construct
SEQUENCE: 71
ttagggataa cagggtaatc ccttttcaga acaatgttat gtcg                   44

SEQ ID NO: 72           moltype = DNA  length = 40
FEATURE                 Location/Qualifiers
source                  1..40
                        mol_type = other DNA
                        organism = synthetic construct
```

```
SEQUENCE: 72
ttagggataa cagggtaatc tccttgcctc cactcacacc                    40

SEQ ID NO: 73           moltype = DNA  length = 41
FEATURE                 Location/Qualifiers
source                  1..41
                        mol_type = other DNA
                        organism = synthetic construct
SEQUENCE: 73
ttagggataa cagggtaatc tcctgagggc aaatgttgat g                  41

SEQ ID NO: 74           moltype = DNA  length = 41
FEATURE                 Location/Qualifiers
source                  1..41
                        mol_type = other DNA
                        organism = synthetic construct
SEQUENCE: 74
ttagggataa cagggtaatc tgggcaaact tgtggtagca g                  41

SEQ ID NO: 75           moltype = DNA  length = 41
FEATURE                 Location/Qualifiers
source                  1..41
                        mol_type = other DNA
                        organism = synthetic construct
SEQUENCE: 75
ttagggataa cagggtaatc tcttctcctg gtctgtggaa c                  41

SEQ ID NO: 76           moltype = DNA  length = 40
FEATURE                 Location/Qualifiers
source                  1..40
                        mol_type = other DNA
                        organism = synthetic construct
SEQUENCE: 76
ttagggataa cagggtaatc gactctgtag gctgcagttc                    40

SEQ ID NO: 77           moltype = DNA  length = 41
FEATURE                 Location/Qualifiers
source                  1..41
                        mol_type = other DNA
                        organism = synthetic construct
SEQUENCE: 77
ttagggataa cagggtaatc ttgctccttc catccttgct c                  41

SEQ ID NO: 78           moltype = DNA  length = 40
FEATURE                 Location/Qualifiers
source                  1..40
                        mol_type = other DNA
                        organism = synthetic construct
SEQUENCE: 78
ttagggataa cagggtaatc aagggacaag cagccacacc                    40

SEQ ID NO: 79           moltype = DNA  length = 44
FEATURE                 Location/Qualifiers
source                  1..44
                        mol_type = other DNA
                        organism = synthetic construct
SEQUENCE: 79
ttagggataa cagggtaatc caaaagagaa atcacgcatt tatg               44

SEQ ID NO: 80           moltype = DNA  length = 41
FEATURE                 Location/Qualifiers
source                  1..41
                        mol_type = other DNA
                        organism = synthetic construct
SEQUENCE: 80
ttagggataa cagggtaatc gctgtctgca tttatgaacc c                  41

SEQ ID NO: 81           moltype = DNA  length = 41
FEATURE                 Location/Qualifiers
source                  1..41
                        mol_type = other DNA
                        organism = synthetic construct
SEQUENCE: 81
ttagggataa cagggtaatc acttgcccag cgtgtcctct c                  41

SEQ ID NO: 82           moltype = DNA  length = 41
FEATURE                 Location/Qualifiers
source                  1..41
                        mol_type = other DNA
```

```
                        organism = synthetic construct
SEQUENCE: 82
ttagggataa cagggtaatc cagttagagg gcccacagag g                    41

SEQ ID NO: 83           moltype = DNA  length = 45
FEATURE                 Location/Qualifiers
source                  1..45
                        mol_type = other DNA
                        organism = synthetic construct
SEQUENCE: 83
ttagggataa cagggtaatc gagacatgca tgaacatttt tctcc                45

SEQ ID NO: 84           moltype = DNA  length = 44
FEATURE                 Location/Qualifiers
source                  1..44
                        mol_type = other DNA
                        organism = synthetic construct
SEQUENCE: 84
ttagggataa cagggtaatc ttttgatctc tgaatttgca agag                 44

SEQ ID NO: 85           moltype = DNA  length = 40
FEATURE                 Location/Qualifiers
source                  1..40
                        mol_type = other DNA
                        organism = synthetic construct
SEQUENCE: 85
ttagggataa cagggtaatc ctggaaggca ggtaggatcc                      40

SEQ ID NO: 86           moltype = DNA  length = 40
FEATURE                 Location/Qualifiers
source                  1..40
                        mol_type = other DNA
                        organism = synthetic construct
SEQUENCE: 86
ttagggataa cagggtaatc ccccaaaccc caatgaagag                      40

SEQ ID NO: 87           moltype = DNA  length = 40
FEATURE                 Location/Qualifiers
source                  1..40
                        mol_type = other DNA
                        organism = synthetic construct
SEQUENCE: 87
ttagggataa cagggtaatc tttgcagaaa acagatctgt                      40

SEQ ID NO: 88           moltype = DNA  length = 40
FEATURE                 Location/Qualifiers
source                  1..40
                        mol_type = other DNA
                        organism = synthetic construct
SEQUENCE: 88
ttagggataa cagggtaatc aagttgtgga caggttttga                      40

SEQ ID NO: 89           moltype = DNA  length = 40
FEATURE                 Location/Qualifiers
source                  1..40
                        mol_type = other DNA
                        organism = synthetic construct
SEQUENCE: 89
ttagggataa cagggtaatc tttcagttca atgcatgctg                      40

SEQ ID NO: 90           moltype = DNA  length = 40
FEATURE                 Location/Qualifiers
source                  1..40
                        mol_type = other DNA
                        organism = synthetic construct
SEQUENCE: 90
ttagggataa cagggtaatc cggggccgcg gaaaggaagg                      40

SEQ ID NO: 91           moltype = DNA  length = 40
FEATURE                 Location/Qualifiers
source                  1..40
                        mol_type = other DNA
                        organism = synthetic construct
SEQUENCE: 91
ttagggataa cagggtaatc cccacgtggc ggagggactg                      40

SEQ ID NO: 92           moltype = DNA  length = 40
FEATURE                 Location/Qualifiers
source                  1..40
```

```
                        mol_type = other DNA
                        organism = synthetic construct
SEQUENCE: 92
ttagggataa cagggtaatc ctggccctcc cactcctgac                          40

SEQ ID NO: 93           moltype = DNA  length = 40
FEATURE                 Location/Qualifiers
source                  1..40
                        mol_type = other DNA
                        organism = synthetic construct
SEQUENCE: 93
ttagggataa cagggtaatc atcctggtcc cctttcatgc                          40

SEQ ID NO: 94           moltype = DNA  length = 39
FEATURE                 Location/Qualifiers
source                  1..39
                        mol_type = other DNA
                        organism = synthetic construct
SEQUENCE: 94
ttagggataa cagggtaatc tgtactcagg gctctgcag                           39

SEQ ID NO: 95           moltype = DNA  length = 40
FEATURE                 Location/Qualifiers
source                  1..40
                        mol_type = other DNA
                        organism = synthetic construct
SEQUENCE: 95
ttagggataa cagggtaatc gccacccata tgtaccatcg                          40

SEQ ID NO: 96           moltype = DNA  length = 42
FEATURE                 Location/Qualifiers
source                  1..42
                        mol_type = other DNA
                        organism = synthetic construct
SEQUENCE: 96
ttagggataa cagggtaatc attctccaaa atggcccgag ac                       42

SEQ ID NO: 97           moltype = DNA  length = 40
FEATURE                 Location/Qualifiers
source                  1..40
                        mol_type = other DNA
                        organism = synthetic construct
SEQUENCE: 97
ttagggataa cagggtaatc acgagtacct catcccacag                          40

SEQ ID NO: 98           moltype = DNA  length = 40
FEATURE                 Location/Qualifiers
source                  1..40
                        mol_type = other DNA
                        organism = synthetic construct
SEQUENCE: 98
ttagggataa cagggtaatc attttgaagg agacggactg                          40

SEQ ID NO: 99           moltype = DNA  length = 40
FEATURE                 Location/Qualifiers
source                  1..40
                        mol_type = other DNA
                        organism = synthetic construct
SEQUENCE: 99
ttagggataa cagggtaatc ccatcaccac gaaatccttg                          40

SEQ ID NO: 100          moltype = DNA  length = 41
FEATURE                 Location/Qualifiers
source                  1..41
                        mol_type = other DNA
                        organism = synthetic construct
SEQUENCE: 100
ttagggataa cagggtaatc aggctttcac gttagttagt g                        41

SEQ ID NO: 101          moltype = DNA  length = 43
FEATURE                 Location/Qualifiers
source                  1..43
                        mol_type = other DNA
                        organism = synthetic construct
SEQUENCE: 101
ttagggataa cagggtaatc tctcccaatc atcactcgag tcc                      43

SEQ ID NO: 102          moltype = DNA  length = 40
FEATURE                 Location/Qualifiers
```

```
source                  1..40
                        mol_type = other DNA
                        organism = synthetic construct
SEQUENCE: 102
ttagggataa cagggtaatc tgaggtgtag gtgctgtcac                        40

SEQ ID NO: 103          moltype = DNA  length = 41
FEATURE                 Location/Qualifiers
source                  1..41
                        mol_type = other DNA
                        organism = synthetic construct
SEQUENCE: 103
ttagggataa cagggtaatc aaaggtcagt gggattgtaa c                      41

SEQ ID NO: 104          moltype = DNA  length = 40
FEATURE                 Location/Qualifiers
source                  1..40
                        mol_type = other DNA
                        organism = synthetic construct
SEQUENCE: 104
ttagggataa cagggtaatc taagcactgt caccccttcc                        40

SEQ ID NO: 105          moltype = DNA  length = 41
FEATURE                 Location/Qualifiers
source                  1..41
                        mol_type = other DNA
                        organism = synthetic construct
SEQUENCE: 105
ttagggataa cagggtaatc gtcctcatgt attggtctct c                      41

SEQ ID NO: 106          moltype = DNA  length = 44
FEATURE                 Location/Qualifiers
source                  1..44
                        mol_type = other DNA
                        organism = synthetic construct
SEQUENCE: 106
ttagggataa cagggtaatc cagaaaacaa gtggttatag atgg                   44

SEQ ID NO: 107          moltype = DNA  length = 40
FEATURE                 Location/Qualifiers
source                  1..40
                        mol_type = other DNA
                        organism = synthetic construct
SEQUENCE: 107
ttagggataa cagggtaatc aagtggttct ggattagctg                        40

SEQ ID NO: 108          moltype = DNA  length = 41
FEATURE                 Location/Qualifiers
source                  1..41
                        mol_type = other DNA
                        organism = synthetic construct
SEQUENCE: 108
ttagggataa cagggtaatc tggtgtgaaa tgactgagta c                      41

SEQ ID NO: 109          moltype = DNA  length = 42
FEATURE                 Location/Qualifiers
source                  1..42
                        mol_type = other DNA
                        organism = synthetic construct
SEQUENCE: 109
ttagggataa cagggtaatc gacaggatga caggaagagc ac                     42

SEQ ID NO: 110          moltype = DNA  length = 40
FEATURE                 Location/Qualifiers
source                  1..40
                        mol_type = other DNA
                        organism = synthetic construct
SEQUENCE: 110
ttagggataa cagggtaatc tcgtcagtgg cccgcttctg                        40

SEQ ID NO: 111          moltype = DNA  length = 40
FEATURE                 Location/Qualifiers
source                  1..40
                        mol_type = other DNA
                        organism = synthetic construct
SEQUENCE: 111
ttagggataa cagggtaatc gtcagcatta ctctgtgtcc                        40

SEQ ID NO: 112          moltype = DNA  length = 40
```

```
FEATURE                Location/Qualifiers
source                 1..40
                       mol_type = other DNA
                       organism = synthetic construct
SEQUENCE: 112
ttagggataa cagggtaatc caggccttcc cctctctttc                        40

SEQ ID NO: 113         moltype = DNA  length = 43
FEATURE                Location/Qualifiers
source                 1..43
                       mol_type = other DNA
                       organism = synthetic construct
SEQUENCE: 113
ttagggataa cagggtaatc cttgtttccg tgaaagacta tac                    43

SEQ ID NO: 114         moltype = DNA  length = 43
FEATURE                Location/Qualifiers
source                 1..43
                       mol_type = other DNA
                       organism = synthetic construct
SEQUENCE: 114
ttagggataa cagggtaatc actagggcta cttctttgat ttc                    43

SEQ ID NO: 115         moltype = DNA  length = 44
FEATURE                Location/Qualifiers
source                 1..44
                       mol_type = other DNA
                       organism = synthetic construct
SEQUENCE: 115
ttagggataa cagggtaatc cctattatga cttgtcacaa tgtc                   44

SEQ ID NO: 116         moltype = DNA  length = 41
FEATURE                Location/Qualifiers
source                 1..41
                       mol_type = other DNA
                       organism = synthetic construct
SEQUENCE: 116
ttagggataa cagggtaatc tctttttctg tttggcttga c                      41

SEQ ID NO: 117         moltype = DNA  length = 40
FEATURE                Location/Qualifiers
source                 1..40
                       mol_type = other DNA
                       organism = synthetic construct
SEQUENCE: 117
ttagggataa cagggtaatc tttacccctc cttcctagag                        40

SEQ ID NO: 118         moltype = DNA  length = 40
FEATURE                Location/Qualifiers
source                 1..40
                       mol_type = other DNA
                       organism = synthetic construct
SEQUENCE: 118
ttagggataa cagggtaatc ccaccccaag agagcaacac                        40

SEQ ID NO: 119         moltype = DNA  length = 41
FEATURE                Location/Qualifiers
source                 1..41
                       mol_type = other DNA
                       organism = synthetic construct
SEQUENCE: 119
ttagggataa cagggtaatc gtgatgtcca ccctgttcct g                      41

SEQ ID NO: 120         moltype = DNA  length = 40
FEATURE                Location/Qualifiers
source                 1..40
                       mol_type = other DNA
                       organism = synthetic construct
SEQUENCE: 120
ttagggataa cagggtaatc gcagaacagg atgcagagac                        40

SEQ ID NO: 121         moltype = DNA  length = 41
FEATURE                Location/Qualifiers
source                 1..41
                       mol_type = other DNA
                       organism = synthetic construct
SEQUENCE: 121
ttagggataa cagggtaatc tggtggaaag aacctctcaa c                      41
```

```
SEQ ID NO: 122          moltype = DNA  length = 41
FEATURE                 Location/Qualifiers
source                  1..41
                        mol_type = other DNA
                        organism = synthetic construct
SEQUENCE: 122
ttagggataa cagggtaatc ctctgagtag aaccattgct c                        41

SEQ ID NO: 123          moltype = DNA  length = 40
FEATURE                 Location/Qualifiers
source                  1..40
                        mol_type = other DNA
                        organism = synthetic construct
SEQUENCE: 123
ttagggataa cagggtaatc gggtgggccg aagtctgacc                          40

SEQ ID NO: 124          moltype = DNA  length = 40
FEATURE                 Location/Qualifiers
source                  1..40
                        mol_type = other DNA
                        organism = synthetic construct
SEQUENCE: 124
ttagggataa cagggtaatc gccttcggct ccacctggtc                          40

SEQ ID NO: 125          moltype = DNA  length = 43
FEATURE                 Location/Qualifiers
source                  1..43
                        mol_type = other DNA
                        organism = synthetic construct
SEQUENCE: 125
ttagggataa cagggtaatc gtatgtttgg tagttgcata tgg                      43

SEQ ID NO: 126          moltype = DNA  length = 43
FEATURE                 Location/Qualifiers
source                  1..43
                        mol_type = other DNA
                        organism = synthetic construct
SEQUENCE: 126
ttagggataa cagggtaatc aatatttcgt atggtgccat ttg                      43

SEQ ID NO: 127          moltype = DNA  length = 41
FEATURE                 Location/Qualifiers
source                  1..41
                        mol_type = other DNA
                        organism = synthetic construct
SEQUENCE: 127
ttagggataa cagggtaatc ctcctgatga gaagagggtt g                        41

SEQ ID NO: 128          moltype = DNA  length = 43
FEATURE                 Location/Qualifiers
source                  1..43
                        mol_type = other DNA
                        organism = synthetic construct
SEQUENCE: 128
ttagggataa cagggtaatc tcactgcagt tgtaggttat aac                      43

SEQ ID NO: 129          moltype = DNA  length = 46
FEATURE                 Location/Qualifiers
source                  1..46
                        mol_type = other DNA
                        organism = synthetic construct
SEQUENCE: 129
ttagggataa cagggtaatc aaaatatttc aatgggtcat atcaca                   46

SEQ ID NO: 130          moltype = DNA  length = 41
FEATURE                 Location/Qualifiers
source                  1..41
                        mol_type = other DNA
                        organism = synthetic construct
SEQUENCE: 130
ttagggataa cagggtaatc tagtcactgg cagcaacagt c                        41

SEQ ID NO: 131          moltype = DNA  length = 41
FEATURE                 Location/Qualifiers
source                  1..41
                        mol_type = other DNA
                        organism = synthetic construct
SEQUENCE: 131
ttagggataa cagggtaatc ttcctcagga ttgcctttac c                        41
```

```
SEQ ID NO: 132          moltype = DNA  length = 40
FEATURE                 Location/Qualifiers
source                  1..40
                        mol_type = other DNA
                        organism = synthetic construct
SEQUENCE: 132
ttagggataa cagggtaatc actgcattct gactttcagt                         40

SEQ ID NO: 133          moltype = DNA  length = 44
FEATURE                 Location/Qualifiers
source                  1..44
                        mol_type = other DNA
                        organism = synthetic construct
SEQUENCE: 133
ttagggataa cagggtaatc aaaaagctct aattctctac atgc                    44

SEQ ID NO: 134          moltype = DNA  length = 42
FEATURE                 Location/Qualifiers
source                  1..42
                        mol_type = other DNA
                        organism = synthetic construct
SEQUENCE: 134
ttagggataa cagggtaatc atgtgtcatc ctgtaagcta cc                      42

SEQ ID NO: 135          moltype = DNA  length = 40
FEATURE                 Location/Qualifiers
source                  1..40
                        mol_type = other DNA
                        organism = synthetic construct
SEQUENCE: 135
ttagggataa cagggtaatc gtggccccctg agcgtcatct                        40

SEQ ID NO: 136          moltype = DNA  length = 40
FEATURE                 Location/Qualifiers
source                  1..40
                        mol_type = other DNA
                        organism = synthetic construct
SEQUENCE: 136
ttagggataa cagggtaatc acccctagac ccaaatcctc                         40

SEQ ID NO: 137          moltype = DNA  length = 40
FEATURE                 Location/Qualifiers
source                  1..40
                        mol_type = other DNA
                        organism = synthetic construct
SEQUENCE: 137
ttagggataa cagggtaatc cgctcccagt ggtgcctgcg                         40

SEQ ID NO: 138          moltype = DNA  length = 40
FEATURE                 Location/Qualifiers
source                  1..40
                        mol_type = other DNA
                        organism = synthetic construct
SEQUENCE: 138
ttagggataa cagggtaatc gctcagaacc tggtatctac                         40

SEQ ID NO: 139          moltype = DNA  length = 40
FEATURE                 Location/Qualifiers
source                  1..40
                        mol_type = other DNA
                        organism = synthetic construct
SEQUENCE: 139
ttagggataa cagggtaatc gctgggagca gcggggagag                         40

SEQ ID NO: 140          moltype = DNA  length = 41
FEATURE                 Location/Qualifiers
source                  1..41
                        mol_type = other DNA
                        organism = synthetic construct
SEQUENCE: 140
ttagggataa cagggtaatc ggcgtcctac tggcatgacc c                       41

SEQ ID NO: 141          moltype = DNA  length = 40
FEATURE                 Location/Qualifiers
source                  1..40
                        mol_type = other DNA
                        organism = synthetic construct
SEQUENCE: 141
```

```
ttagggataa cagggtaatc tggaggacct ggaccgtgtc                    40

SEQ ID NO: 142          moltype = DNA  length = 40
FEATURE                 Location/Qualifiers
source                  1..40
                        mol_type = other DNA
                        organism = synthetic construct
SEQUENCE: 142
ttagggataa cagggtaatc ggtgatcatc gaccaagtcc                    40

SEQ ID NO: 143          moltype = DNA  length = 43
FEATURE                 Location/Qualifiers
source                  1..43
                        mol_type = other DNA
                        organism = synthetic construct
SEQUENCE: 143
ttagggataa cagggtaatc tgagacattg ttggccaaaa tag                43

SEQ ID NO: 144          moltype = DNA  length = 40
FEATURE                 Location/Qualifiers
source                  1..40
                        mol_type = other DNA
                        organism = synthetic construct
SEQUENCE: 144
ttagggataa cagggtaatc actgcagcag ccaccgtgag                    40

SEQ ID NO: 145          moltype = DNA  length = 41
FEATURE                 Location/Qualifiers
source                  1..41
                        mol_type = other DNA
                        organism = synthetic construct
SEQUENCE: 145
ttagggataa cagggtaatc attgattcaa tgaccctcca g                  41

SEQ ID NO: 146          moltype = DNA  length = 44
FEATURE                 Location/Qualifiers
source                  1..44
                        mol_type = other DNA
                        organism = synthetic construct
SEQUENCE: 146
ttagggataa cagggtaatc tccataggct gttccttcaa ccac               44

SEQ ID NO: 147          moltype = DNA  length = 40
FEATURE                 Location/Qualifiers
source                  1..40
                        mol_type = other DNA
                        organism = synthetic construct
SEQUENCE: 147
ttagggataa cagggtaatc ttcagttcag acatgagagc                    40

SEQ ID NO: 148          moltype = DNA  length = 40
FEATURE                 Location/Qualifiers
source                  1..40
                        mol_type = other DNA
                        organism = synthetic construct
SEQUENCE: 148
ttagggataa cagggtaatc agatggcttg atcctgagtc                    40

SEQ ID NO: 149          moltype = DNA  length = 40
FEATURE                 Location/Qualifiers
source                  1..40
                        mol_type = other DNA
                        organism = synthetic construct
SEQUENCE: 149
ttagggataa cagggtaatc ggatgagcct gaccagtgag                    40

SEQ ID NO: 150          moltype = DNA  length = 40
FEATURE                 Location/Qualifiers
source                  1..40
                        mol_type = other DNA
                        organism = synthetic construct
SEQUENCE: 150
ttagggataa cagggtaatc tccagcactc tgacatatgg                    40

SEQ ID NO: 151          moltype = DNA  length = 41
FEATURE                 Location/Qualifiers
source                  1..41
                        mol_type = other DNA
                        organism = synthetic construct
```

```
SEQUENCE: 151
ttagggataa cagggtaatc caagtgaatt gcagtccttc c                    41

SEQ ID NO: 152          moltype = DNA  length = 44
FEATURE                 Location/Qualifiers
source                  1..44
                        mol_type = other DNA
                        organism = synthetic construct
SEQUENCE: 152
ttagggataa cagggtaatc ttctctctcc agagtgctct aatg                 44

SEQ ID NO: 153          moltype = DNA  length = 40
FEATURE                 Location/Qualifiers
source                  1..40
                        mol_type = other DNA
                        organism = synthetic construct
SEQUENCE: 153
ttagggataa cagggtaatc aaaaggtgac atggaaagcc                      40

SEQ ID NO: 154          moltype = DNA  length = 44
FEATURE                 Location/Qualifiers
source                  1..44
                        mol_type = other DNA
                        organism = synthetic construct
SEQUENCE: 154
ttagggataa cagggtaatc atggtactgc atgcgcttga catc                 44

SEQ ID NO: 155          moltype = DNA  length = 41
FEATURE                 Location/Qualifiers
source                  1..41
                        mol_type = other DNA
                        organism = synthetic construct
SEQUENCE: 155
ttagggataa cagggtaatc agacaataaa aggcagcttg g                    41

SEQ ID NO: 156          moltype = DNA  length = 45
FEATURE                 Location/Qualifiers
source                  1..45
                        mol_type = other DNA
                        organism = synthetic construct
SEQUENCE: 156
ttagggataa cagggtaatc tgaatttaaa tggttttctt ttctc                45

SEQ ID NO: 157          moltype = DNA  length = 42
FEATURE                 Location/Qualifiers
source                  1..42
                        mol_type = other DNA
                        organism = synthetic construct
SEQUENCE: 157
ttagggataa cagggtaatc tcctttgcag gactgtcaag ca                   42

SEQ ID NO: 158          moltype = DNA  length = 41
FEATURE                 Location/Qualifiers
source                  1..41
                        mol_type = other DNA
                        organism = synthetic construct
SEQUENCE: 158
ttagggataa cagggtaatc tcatcaggag agcatttaag g                    41

SEQ ID NO: 159          moltype = DNA  length = 46
FEATURE                 Location/Qualifiers
source                  1..46
                        mol_type = other DNA
                        organism = synthetic construct
SEQUENCE: 159
ttagggataa cagggtaatc accataaaat catatgctcc actaac               46

SEQ ID NO: 160          moltype = DNA  length = 43
FEATURE                 Location/Qualifiers
source                  1..43
                        mol_type = other DNA
                        organism = synthetic construct
SEQUENCE: 160
ttagggataa cagggtaatc catgttttga tgggtcatgt tgc                  43

SEQ ID NO: 161          moltype = DNA  length = 40
FEATURE                 Location/Qualifiers
source                  1..40
                        mol_type = other DNA
```

```
                        organism = synthetic construct
SEQUENCE: 161
ttagggataa cagggtaatc gaagtcccaa ccatgacaag                        40

SEQ ID NO: 162          moltype = DNA  length = 44
FEATURE                 Location/Qualifiers
source                  1..44
                        mol_type = other DNA
                        organism = synthetic construct
SEQUENCE: 162
ttagggataa cagggtaatc tcctttctac ccaaaagtaa tcat                   44

SEQ ID NO: 163          moltype = DNA  length = 44
FEATURE                 Location/Qualifiers
source                  1..44
                        mol_type = other DNA
                        organism = synthetic construct
SEQUENCE: 163
ttagggataa cagggtaatc aagaggaagc ttagatagtt ctcg                   44

SEQ ID NO: 164          moltype = DNA  length = 45
FEATURE                 Location/Qualifiers
source                  1..45
                        mol_type = other DNA
                        organism = synthetic construct
SEQUENCE: 164
ttagggataa cagggtaatc gaatgtgttt ctccatacag gtcac                  45

SEQ ID NO: 165          moltype = DNA  length = 41
FEATURE                 Location/Qualifiers
source                  1..41
                        mol_type = other DNA
                        organism = synthetic construct
SEQUENCE: 165
ttagggataa cagggtaatc atctttgtca tcagctgaag a                      41

SEQ ID NO: 166          moltype = DNA  length = 40
FEATURE                 Location/Qualifiers
source                  1..40
                        mol_type = other DNA
                        organism = synthetic construct
SEQUENCE: 166
ttagggataa cagggtaatc atctccctcc aaaagtggtg                        40

SEQ ID NO: 167          moltype = DNA  length = 40
FEATURE                 Location/Qualifiers
source                  1..40
                        mol_type = other DNA
                        organism = synthetic construct
SEQUENCE: 167
ttagggataa cagggtaatc cagatagccc tggacaaacc                        40

SEQ ID NO: 168          moltype = DNA  length = 40
FEATURE                 Location/Qualifiers
source                  1..40
                        mol_type = other DNA
                        organism = synthetic construct
SEQUENCE: 168
ttagggataa cagggtaatc aggtgcccta ctacctggag                        40

SEQ ID NO: 169          moltype = DNA  length = 41
FEATURE                 Location/Qualifiers
source                  1..41
                        mol_type = other DNA
                        organism = synthetic construct
SEQUENCE: 169
ttagggataa cagggtaatc tggtcctgtg agggctgcaa g                      41

SEQ ID NO: 170          moltype = DNA  length = 42
FEATURE                 Location/Qualifiers
source                  1..42
                        mol_type = other DNA
                        organism = synthetic construct
SEQUENCE: 170
ttagggataa cagggtaatc ggaagagctg ccaggcctgc cg                     42

SEQ ID NO: 171          moltype = DNA  length = 42
FEATURE                 Location/Qualifiers
source                  1..42
```

```
                         mol_type = other DNA
                         organism = synthetic construct
SEQUENCE: 171
ttagggataa cagggtaatc tttgtataaa agtttacacg gg                    42

SEQ ID NO: 172           moltype = DNA  length = 40
FEATURE                  Location/Qualifiers
source                   1..40
                         mol_type = other DNA
                         organism = synthetic construct
SEQUENCE: 172
ttagggataa cagggtaatc gggtgaagtg gggtctgctg                       40

SEQ ID NO: 173           moltype = DNA  length = 41
FEATURE                  Location/Qualifiers
source                   1..41
                         mol_type = other DNA
                         organism = synthetic construct
SEQUENCE: 173
ttagggataa cagggtaatc ttagagcgtt tgatcatgag c                     41

SEQ ID NO: 174           moltype = DNA  length = 40
FEATURE                  Location/Qualifiers
source                   1..40
                         mol_type = other DNA
                         organism = synthetic construct
SEQUENCE: 174
ttagggataa cagggtaatc gatggtcagt gccttgttgg                       40

SEQ ID NO: 175           moltype = DNA  length = 40
FEATURE                  Location/Qualifiers
source                   1..40
                         mol_type = other DNA
                         organism = synthetic construct
SEQUENCE: 175
ttagggataa cagggtaatc tcactgaagg gtctggtagg                       40

SEQ ID NO: 176           moltype = DNA  length = 41
FEATURE                  Location/Qualifiers
source                   1..41
                         mol_type = other DNA
                         organism = synthetic construct
SEQUENCE: 176
ttagggataa cagggtaatc agggagctgg ttcacatgat c                     41

SEQ ID NO: 177           moltype = DNA  length = 42
FEATURE                  Location/Qualifiers
source                   1..42
                         mol_type = other DNA
                         organism = synthetic construct
SEQUENCE: 177
ttagggataa cagggtaatc tcacaacaag ttcttgaaaa gc                    42

SEQ ID NO: 178           moltype = DNA  length = 40
FEATURE                  Location/Qualifiers
source                   1..40
                         mol_type = other DNA
                         organism = synthetic construct
SEQUENCE: 178
ttagggataa cagggtaatc tctagggatt tcagcactcc                       40

SEQ ID NO: 179           moltype = DNA  length = 40
FEATURE                  Location/Qualifiers
source                   1..40
                         mol_type = other DNA
                         organism = synthetic construct
SEQUENCE: 179
ttagggataa cagggtaatc cagcagggat tatctgaacc                       40

SEQ ID NO: 180           moltype = DNA  length = 44
FEATURE                  Location/Qualifiers
source                   1..44
                         mol_type = other DNA
                         organism = synthetic construct
SEQUENCE: 180
ttagggataa cagggtaatc agttagtata tacaatgcca cctg                  44

SEQ ID NO: 181           moltype = DNA  length = 41
FEATURE                  Location/Qualifiers
```

```
source                  1..41
                        mol_type = other DNA
                        organism = synthetic construct
SEQUENCE: 181
ttagggataa cagggtaatc tagtctactt tgtccccagt c                       41

SEQ ID NO: 182          moltype = DNA  length = 40
FEATURE                 Location/Qualifiers
source                  1..40
                        mol_type = other DNA
                        organism = synthetic construct
SEQUENCE: 182
ttagggataa cagggtaatc caagcagctg gtggaagacc                         40

SEQ ID NO: 183          moltype = DNA  length = 41
FEATURE                 Location/Qualifiers
source                  1..41
                        mol_type = other DNA
                        organism = synthetic construct
SEQUENCE: 183
ttagggataa cagggtaatc ccttgcttct cagatgaaac c                       41

SEQ ID NO: 184          moltype = DNA  length = 40
FEATURE                 Location/Qualifiers
source                  1..40
                        mol_type = other DNA
                        organism = synthetic construct
SEQUENCE: 184
ttagggataa cagggtaatc cctccccgcc tcccgctctc                         40

SEQ ID NO: 185          moltype = DNA  length = 40
FEATURE                 Location/Qualifiers
source                  1..40
                        mol_type = other DNA
                        organism = synthetic construct
SEQUENCE: 185
ttagggataa cagggtaatc cattacccag gggagccttc                         40

SEQ ID NO: 186          moltype = DNA  length = 40
FEATURE                 Location/Qualifiers
source                  1..40
                        mol_type = other DNA
                        organism = synthetic construct
SEQUENCE: 186
ttagggataa cagggtaatc aggtgaagcc aaacctgctc                         40

SEQ ID NO: 187          moltype = DNA  length = 40
FEATURE                 Location/Qualifiers
source                  1..40
                        mol_type = other DNA
                        organism = synthetic construct
SEQUENCE: 187
ttagggataa cagggtaatc ggactgatac cccagctcag                         40

SEQ ID NO: 188          moltype = DNA  length = 42
FEATURE                 Location/Qualifiers
source                  1..42
                        mol_type = other DNA
                        organism = synthetic construct
SEQUENCE: 188
ttagggataa cagggtaatc cccaagtaaa tgagtctcaa cg                      42

SEQ ID NO: 189          moltype = DNA  length = 41
FEATURE                 Location/Qualifiers
source                  1..41
                        mol_type = other DNA
                        organism = synthetic construct
SEQUENCE: 189
ttagggataa cagggtaatc ccagagttca tggatgcact g                       41

SEQ ID NO: 190          moltype = DNA  length = 40
FEATURE                 Location/Qualifiers
source                  1..40
                        mol_type = other DNA
                        organism = synthetic construct
SEQUENCE: 190
ttagggataa cagggtaatc ccaggtacag gggcgaggtc                         40

SEQ ID NO: 191          moltype = DNA  length = 41
```

```
FEATURE                Location/Qualifiers
source                 1..41
                       mol_type = other DNA
                       organism = synthetic construct
SEQUENCE: 191
ttagggataa cagggtaatc aagcacctcc atctctttgt c                        41

SEQ ID NO: 192         moltype = DNA  length = 41
FEATURE                Location/Qualifiers
source                 1..41
                       mol_type = other DNA
                       organism = synthetic construct
SEQUENCE: 192
ttagggataa cagggtaatc tccacagtga gctcgatcct c                        41

SEQ ID NO: 193         moltype = DNA  length = 45
FEATURE                Location/Qualifiers
source                 1..45
                       mol_type = other DNA
                       organism = synthetic construct
SEQUENCE: 193
ttagggataa cagggtaatc tctgaactat ttatggacaa cagtc                    45

SEQ ID NO: 194         moltype = DNA  length = 40
FEATURE                Location/Qualifiers
source                 1..40
                       mol_type = other DNA
                       organism = synthetic construct
SEQUENCE: 194
ttagggataa cagggtaatc tgctctgaga aaggcattag                          40

SEQ ID NO: 195         moltype = DNA  length = 40
FEATURE                Location/Qualifiers
source                 1..40
                       mol_type = other DNA
                       organism = synthetic construct
SEQUENCE: 195
ttagggataa cagggtaatc ttacggtagt gggggaaggc                          40

SEQ ID NO: 196         moltype = DNA  length = 41
FEATURE                Location/Qualifiers
source                 1..41
                       mol_type = other DNA
                       organism = synthetic construct
SEQUENCE: 196
ttagggataa cagggtaatc tttgacctca ggtttctaac g                        41

SEQ ID NO: 197         moltype = DNA  length = 41
FEATURE                Location/Qualifiers
source                 1..41
                       mol_type = other DNA
                       organism = synthetic construct
SEQUENCE: 197
ttagggataa cagggtaatc tctcagggta caaattctca g                        41

SEQ ID NO: 198         moltype = DNA  length = 42
FEATURE                Location/Qualifiers
source                 1..42
                       mol_type = other DNA
                       organism = synthetic construct
SEQUENCE: 198
ttagggataa cagggtaatc cgacatcgcg atggcccagc tc                       42

SEQ ID NO: 199         moltype = DNA  length = 41
FEATURE                Location/Qualifiers
source                 1..41
                       mol_type = other DNA
                       organism = synthetic construct
SEQUENCE: 199
ttagggataa cagggtaatc gtgcacgacg ctgcccggga g                        41

SEQ ID NO: 200         moltype = DNA  length = 41
FEATURE                Location/Qualifiers
source                 1..41
                       mol_type = other DNA
                       organism = synthetic construct
SEQUENCE: 200
ttagggataa cagggtaatc tctacacaag cttcctttcc g                        41
```

```
SEQ ID NO: 201          moltype = DNA  length = 40
FEATURE                 Location/Qualifiers
source                  1..40
                        mol_type = other DNA
                        organism = synthetic construct
SEQUENCE: 201
ttagggataa cagggtaatc cccctgcaaa cttcgtcctc                         40

SEQ ID NO: 202          moltype = DNA  length = 40
FEATURE                 Location/Qualifiers
source                  1..40
                        mol_type = other DNA
                        organism = synthetic construct
SEQUENCE: 202
ttagggataa cagggtaatc ggctgcggag agggggagag                         40

SEQ ID NO: 203          moltype = DNA  length = 43
FEATURE                 Location/Qualifiers
source                  1..43
                        mol_type = other DNA
                        organism = synthetic construct
SEQUENCE: 203
ttagggataa cagggtaatc gataatccat tgcctgtcta aag                     43

SEQ ID NO: 204          moltype = DNA  length = 43
FEATURE                 Location/Qualifiers
source                  1..43
                        mol_type = other DNA
                        organism = synthetic construct
SEQUENCE: 204
ttagggataa cagggtaatc tgttgacttt ttagttttac ttt                     43

SEQ ID NO: 205          moltype = DNA  length = 40
FEATURE                 Location/Qualifiers
source                  1..40
                        mol_type = other DNA
                        organism = synthetic construct
SEQUENCE: 205
ttagggataa cagggtaatc ctgtgggctg aaggctgttc                         40

SEQ ID NO: 206          moltype = DNA  length = 40
FEATURE                 Location/Qualifiers
source                  1..40
                        mol_type = other DNA
                        organism = synthetic construct
SEQUENCE: 206
ttagggataa cagggtaatc agcgcaacaa gcccactgtc                         40

SEQ ID NO: 207          moltype = DNA  length = 40
FEATURE                 Location/Qualifiers
source                  1..40
                        mol_type = other DNA
                        organism = synthetic construct
SEQUENCE: 207
ttagggataa cagggtaatc gttccatctc ccacttgtcg                         40

SEQ ID NO: 208          moltype = DNA  length = 40
FEATURE                 Location/Qualifiers
source                  1..40
                        mol_type = other DNA
                        organism = synthetic construct
SEQUENCE: 208
ttagggataa cagggtaatc taatgccagc agacgccttg                         40

SEQ ID NO: 209          moltype = DNA  length = 40
FEATURE                 Location/Qualifiers
source                  1..40
                        mol_type = other DNA
                        organism = synthetic construct
SEQUENCE: 209
ttagggataa cagggtaatc acccactgaa aagcacttcc                         40

SEQ ID NO: 210          moltype = DNA  length = 40
FEATURE                 Location/Qualifiers
source                  1..40
                        mol_type = other DNA
                        organism = synthetic construct
SEQUENCE: 210
ttagggataa cagggtaatc cggcgcgaga ccctctcttc                         40
```

```
SEQ ID NO: 211          moltype = DNA  length = 40
FEATURE                 Location/Qualifiers
source                  1..40
                        mol_type = other DNA
                        organism = synthetic construct
SEQUENCE: 211
ttagggataa cagggtaatc gtgttgaagt cctcgttgtc                    40

SEQ ID NO: 212          moltype = DNA  length = 40
FEATURE                 Location/Qualifiers
source                  1..40
                        mol_type = other DNA
                        organism = synthetic construct
SEQUENCE: 212
ttagggataa cagggtaatc cgccctgaga cctcctaggc                    40

SEQ ID NO: 213          moltype = DNA  length = 42
FEATURE                 Location/Qualifiers
source                  1..42
                        mol_type = other DNA
                        organism = synthetic construct
SEQUENCE: 213
ttagggataa cagggtaatc acctgttaag tttgtatgca ac                 42

SEQ ID NO: 214          moltype = DNA  length = 42
FEATURE                 Location/Qualifiers
source                  1..42
                        mol_type = other DNA
                        organism = synthetic construct
SEQUENCE: 214
ttagggataa cagggtaatc gtgaagatga caatcatgtt gc                 42

SEQ ID NO: 215          moltype = DNA  length = 45
FEATURE                 Location/Qualifiers
source                  1..45
                        mol_type = other DNA
                        organism = synthetic construct
SEQUENCE: 215
ttagggataa cagggtaatc aatttgcccc gatgtaataa atatg              45

SEQ ID NO: 216          moltype = DNA  length = 43
FEATURE                 Location/Qualifiers
source                  1..43
                        mol_type = other DNA
                        organism = synthetic construct
SEQUENCE: 216
ttagggataa cagggtaatc tccaataaat tctcagatcc agg                43

SEQ ID NO: 217          moltype = DNA  length = 42
FEATURE                 Location/Qualifiers
source                  1..42
                        mol_type = other DNA
                        organism = synthetic construct
SEQUENCE: 217
ttagggataa cagggtaatc taaatggcta cgacccagtt ac                 42

SEQ ID NO: 218          moltype = DNA  length = 46
FEATURE                 Location/Qualifiers
source                  1..46
                        mol_type = other DNA
                        organism = synthetic construct
SEQUENCE: 218
ttagggataa cagggtaatc ggttaagaaa actgttccaa tacatg             46

SEQ ID NO: 219          moltype = DNA  length = 41
FEATURE                 Location/Qualifiers
source                  1..41
                        mol_type = other DNA
                        organism = synthetic construct
SEQUENCE: 219
ttagggataa cagggtaatc acagtttgac agttaaaggc a                  41

SEQ ID NO: 220          moltype = DNA  length = 44
FEATURE                 Location/Qualifiers
source                  1..44
                        mol_type = other DNA
                        organism = synthetic construct
SEQUENCE: 220
```

-continued

```
ttagggataa cagggtaatc atacattctt cataccagga ccag                44

SEQ ID NO: 221          moltype = DNA  length = 40
FEATURE                 Location/Qualifiers
source                  1..40
                        mol_type = other DNA
                        organism = synthetic construct
SEQUENCE: 221
ttagggataa cagggtaatc tcggttggct ttgtctttat                     40

SEQ ID NO: 222          moltype = DNA  length = 41
FEATURE                 Location/Qualifiers
source                  1..41
                        mol_type = other DNA
                        organism = synthetic construct
SEQUENCE: 222
ttagggataa cagggtaatc gttcttcatc agctgtactc c                   41

SEQ ID NO: 223          moltype = DNA  length = 41
FEATURE                 Location/Qualifiers
source                  1..41
                        mol_type = other DNA
                        organism = synthetic construct
SEQUENCE: 223
ttagggataa cagggtaatc gttggtagaa gacttggatc g                   41

SEQ ID NO: 224          moltype = DNA  length = 46
FEATURE                 Location/Qualifiers
source                  1..46
                        mol_type = other DNA
                        organism = synthetic construct
SEQUENCE: 224
ttagggataa cagggtaatc tctaaaatga ttcaatcaaa ctgcag              46

SEQ ID NO: 225          moltype = DNA  length = 45
FEATURE                 Location/Qualifiers
source                  1..45
                        mol_type = other DNA
                        organism = synthetic construct
SEQUENCE: 225
ttagggataa cagggtaatc gaaatgaact gatttgtgaa tatgc               45

SEQ ID NO: 226          moltype = DNA  length = 40
FEATURE                 Location/Qualifiers
source                  1..40
                        mol_type = other DNA
                        organism = synthetic construct
SEQUENCE: 226
ttagggataa cagggtaatc cggggtgttg gagttcatgg                     40

SEQ ID NO: 227          moltype = DNA  length = 43
FEATURE                 Location/Qualifiers
source                  1..43
                        mol_type = other DNA
                        organism = synthetic construct
SEQUENCE: 227
ttagggataa cagggtaatc atgcagtaaa tggctatctc cag                 43

SEQ ID NO: 228          moltype = DNA  length = 40
FEATURE                 Location/Qualifiers
source                  1..40
                        mol_type = other DNA
                        organism = synthetic construct
SEQUENCE: 228
ttagggataa cagggtaatc caatctcttt gtccgtggtg                     40

SEQ ID NO: 229          moltype = DNA  length = 40
FEATURE                 Location/Qualifiers
source                  1..40
                        mol_type = other DNA
                        organism = synthetic construct
SEQUENCE: 229
ttagggataa cagggtaatc tgtggccaaa cccatgaagg                     40

SEQ ID NO: 230          moltype = DNA  length = 40
FEATURE                 Location/Qualifiers
source                  1..40
                        mol_type = other DNA
                        organism = synthetic construct
```

```
SEQUENCE: 230
ttagggataa cagggtaatc ggtcactgac agccctctgg                        40

SEQ ID NO: 231          moltype = DNA  length = 41
FEATURE                 Location/Qualifiers
source                  1..41
                        mol_type = other DNA
                        organism = synthetic construct
SEQUENCE: 231
ttagggataa cagggtaatc ggcatggact acgcgcaatg c                      41

SEQ ID NO: 232          moltype = DNA  length = 40
FEATURE                 Location/Qualifiers
source                  1..40
                        mol_type = other DNA
                        organism = synthetic construct
SEQUENCE: 232
ttagggataa cagggtaatc ctgtgcggcg tgggctcccg                        40

SEQ ID NO: 233          moltype = DNA  length = 40
FEATURE                 Location/Qualifiers
source                  1..40
                        mol_type = other DNA
                        organism = synthetic construct
SEQUENCE: 233
ttagggataa cagggtaatc cccccacgga aggtcctgag                        40

SEQ ID NO: 234          moltype = DNA  length = 40
FEATURE                 Location/Qualifiers
source                  1..40
                        mol_type = other DNA
                        organism = synthetic construct
SEQUENCE: 234
ttagggataa cagggtaatc tggctgtgtc ctgggctcgc                        40

SEQ ID NO: 235          moltype = DNA  length = 40
FEATURE                 Location/Qualifiers
source                  1..40
                        mol_type = other DNA
                        organism = synthetic construct
SEQUENCE: 235
ttagggataa cagggtaatc ggcaggtggg gcaggagacc                        40

SEQ ID NO: 236          moltype = DNA  length = 44
FEATURE                 Location/Qualifiers
source                  1..44
                        mol_type = other DNA
                        organism = synthetic construct
SEQUENCE: 236
ttagggataa cagggtaatc attcaggagc ttccaaatag tatg                   44

SEQ ID NO: 237          moltype = DNA  length = 45
FEATURE                 Location/Qualifiers
source                  1..45
                        mol_type = other DNA
                        organism = synthetic construct
SEQUENCE: 237
ttagggataa cagggtaatc cagtttaaaa atcacatggc atctg                  45

SEQ ID NO: 238          moltype = DNA  length = 40
FEATURE                 Location/Qualifiers
source                  1..40
                        mol_type = other DNA
                        organism = synthetic construct
SEQUENCE: 238
ttagggataa cagggtaatc cgctgtgaga catgtctgag                        40

SEQ ID NO: 239          moltype = DNA  length = 40
FEATURE                 Location/Qualifiers
source                  1..40
                        mol_type = other DNA
                        organism = synthetic construct
SEQUENCE: 239
ttagggataa cagggtaatc actcggcact gggctctctg                        40

SEQ ID NO: 240          moltype = DNA  length = 40
FEATURE                 Location/Qualifiers
source                  1..40
                        mol_type = other DNA
```

```
                        organism = synthetic construct
SEQUENCE: 240
ttagggataa cagggtaatc tcgacgccac ttcatgttcc                        40

SEQ ID NO: 241          moltype = DNA  length = 40
FEATURE                 Location/Qualifiers
source                  1..40
                        mol_type = other DNA
                        organism = synthetic construct
SEQUENCE: 241
ttagggataa cagggtaatc ccactgggct acgtcatccc                        40

SEQ ID NO: 242          moltype = DNA  length = 42
FEATURE                 Location/Qualifiers
source                  1..42
                        mol_type = other DNA
                        organism = synthetic construct
SEQUENCE: 242
ttagggataa cagggtaatc ccaaagagga ctttcgctat cg                     42

SEQ ID NO: 243          moltype = DNA  length = 40
FEATURE                 Location/Qualifiers
source                  1..40
                        mol_type = other DNA
                        organism = synthetic construct
SEQUENCE: 243
ttagggataa cagggtaatc ccaccctgga aactctatac                        40

SEQ ID NO: 244          moltype = DNA  length = 42
FEATURE                 Location/Qualifiers
source                  1..42
                        mol_type = other DNA
                        organism = synthetic construct
SEQUENCE: 244
ttagggataa cagggtaatc agggttatgg tgcacattat cc                     42

SEQ ID NO: 245          moltype = DNA  length = 41
FEATURE                 Location/Qualifiers
source                  1..41
                        mol_type = other DNA
                        organism = synthetic construct
SEQUENCE: 245
ttagggataa cagggtaatc gtctccccgc ctgaagagca c                      41

SEQ ID NO: 246          moltype = DNA  length = 41
FEATURE                 Location/Qualifiers
source                  1..41
                        mol_type = other DNA
                        organism = synthetic construct
SEQUENCE: 246
ttagggataa cagggtaatc gcaactgata gacgtaatcc c                      41

SEQ ID NO: 247          moltype = DNA  length = 42
FEATURE                 Location/Qualifiers
source                  1..42
                        mol_type = other DNA
                        organism = synthetic construct
SEQUENCE: 247
ttagggataa cagggtaatc atagtggatc ccaacggact gg                     42

SEQ ID NO: 248          moltype = DNA  length = 42
FEATURE                 Location/Qualifiers
source                  1..42
                        mol_type = other DNA
                        organism = synthetic construct
SEQUENCE: 248
ttagggataa cagggtaatc gctctggaca ttttctcata gg                     42

SEQ ID NO: 249          moltype = DNA  length = 42
FEATURE                 Location/Qualifiers
source                  1..42
                        mol_type = other DNA
                        organism = synthetic construct
SEQUENCE: 249
ttagggataa cagggtaatc gattattttg ccctgttgtc tc                     42

SEQ ID NO: 250          moltype = DNA  length = 42
FEATURE                 Location/Qualifiers
source                  1..42
```

```
                        mol_type = other DNA
                        organism = synthetic construct
SEQUENCE: 250
ttagggataa cagggtaatc gtgaggccag aaggaaccat cg                    42

SEQ ID NO: 251          moltype = DNA  length = 40
FEATURE                 Location/Qualifiers
source                  1..40
                        mol_type = other DNA
                        organism = synthetic construct
SEQUENCE: 251
ttagggataa cagggtaatc gggttcagca gaaagaggac                       40

SEQ ID NO: 252          moltype = DNA  length = 42
FEATURE                 Location/Qualifiers
source                  1..42
                        mol_type = other DNA
                        organism = synthetic construct
SEQUENCE: 252
ttagggataa cagggtaatc gactgctacc ttatatccct tc                    42

SEQ ID NO: 253          moltype = DNA  length = 40
FEATURE                 Location/Qualifiers
source                  1..40
                        mol_type = other DNA
                        organism = synthetic construct
SEQUENCE: 253
ttagggataa cagggtaatc gggaattcaa ggtagtccag                       40

SEQ ID NO: 254          moltype = DNA  length = 40
FEATURE                 Location/Qualifiers
source                  1..40
                        mol_type = other DNA
                        organism = synthetic construct
SEQUENCE: 254
ttagggataa cagggtaatc ggggtcccca tccattcttc                       40

SEQ ID NO: 255          moltype = DNA  length = 40
FEATURE                 Location/Qualifiers
source                  1..40
                        mol_type = other DNA
                        organism = synthetic construct
SEQUENCE: 255
ttagggataa cagggtaatc ccccacgccc aaccctccac                       40

SEQ ID NO: 256          moltype = DNA  length = 40
FEATURE                 Location/Qualifiers
source                  1..40
                        mol_type = other DNA
                        organism = synthetic construct
SEQUENCE: 256
ttagggataa cagggtaatc agtaaagcca cctcacgaac                       40

SEQ ID NO: 257          moltype = DNA  length = 40
FEATURE                 Location/Qualifiers
source                  1..40
                        mol_type = other DNA
                        organism = synthetic construct
SEQUENCE: 257
ttagggataa cagggtaatc gccagtggct gaaattggtg                       40

SEQ ID NO: 258          moltype = DNA  length = 42
FEATURE                 Location/Qualifiers
source                  1..42
                        mol_type = other DNA
                        organism = synthetic construct
SEQUENCE: 258
ttagggataa cagggtaatc gacttttggt gataggagtc tg                    42

SEQ ID NO: 259          moltype = DNA  length = 42
FEATURE                 Location/Qualifiers
source                  1..42
                        mol_type = other DNA
                        organism = synthetic construct
SEQUENCE: 259
ttagggataa cagggtaatc actctttatt tgtccccttg cc                    42

SEQ ID NO: 260          moltype = DNA  length = 40
FEATURE                 Location/Qualifiers
```

```
source                  1..40
                        mol_type = other DNA
                        organism = synthetic construct
SEQUENCE: 260
ttagggataa cagggtaatc ctcagggcac aagggagcag                        40

SEQ ID NO: 261          moltype = DNA  length = 42
FEATURE                 Location/Qualifiers
source                  1..42
                        mol_type = other DNA
                        organism = synthetic construct
SEQUENCE: 261
ttagggataa cagggtaatc ttgtctctga gtccactaaa ag                     42

SEQ ID NO: 262          moltype = DNA  length = 42
FEATURE                 Location/Qualifiers
source                  1..42
                        mol_type = other DNA
                        organism = synthetic construct
SEQUENCE: 262
ttagggataa cagggtaatc aaaaggagag cgtatccaag ag                     42

SEQ ID NO: 263          moltype = DNA  length = 40
FEATURE                 Location/Qualifiers
source                  1..40
                        mol_type = other DNA
                        organism = synthetic construct
SEQUENCE: 263
ttagggataa cagggtaatc tccgtggcca tctggatgcg                        40

SEQ ID NO: 264          moltype = DNA  length = 42
FEATURE                 Location/Qualifiers
source                  1..42
                        mol_type = other DNA
                        organism = synthetic construct
SEQUENCE: 264
ttagggataa cagggtaatc gggctgcatg ttagaatcat cc                     42

SEQ ID NO: 265          moltype = DNA  length = 40
FEATURE                 Location/Qualifiers
source                  1..40
                        mol_type = other DNA
                        organism = synthetic construct
SEQUENCE: 265
ttagggataa cagggtaatc tccccatccc aggagcttac                        40

SEQ ID NO: 266          moltype = DNA  length = 42
FEATURE                 Location/Qualifiers
source                  1..42
                        mol_type = other DNA
                        organism = synthetic construct
SEQUENCE: 266
ttagggataa cagggtaatc gagtttagag cttggcttta tg                     42

SEQ ID NO: 267          moltype = DNA  length = 40
FEATURE                 Location/Qualifiers
source                  1..40
                        mol_type = other DNA
                        organism = synthetic construct
SEQUENCE: 267
ttagggataa cagggtaatc gacacaacac aaaatagccg                        40

SEQ ID NO: 268          moltype = DNA  length = 42
FEATURE                 Location/Qualifiers
source                  1..42
                        mol_type = other DNA
                        organism = synthetic construct
SEQUENCE: 268
ttagggataa cagggtaatc actccaggat aatacacatc ac                     42

SEQ ID NO: 269          moltype = DNA  length = 40
FEATURE                 Location/Qualifiers
source                  1..40
                        mol_type = other DNA
                        organism = synthetic construct
SEQUENCE: 269
ttagggataa cagggtaatc tgggcaaaga gggctccagc                        40

SEQ ID NO: 270          moltype = DNA  length = 41
```

```
FEATURE                Location/Qualifiers
source                 1..41
                       mol_type = other DNA
                       organism = synthetic construct
SEQUENCE: 270
ttagggataa cagggtaatc ggtctgacgg gtagagtgtg c                         41

SEQ ID NO: 271         moltype = DNA  length = 40
FEATURE                Location/Qualifiers
source                 1..40
                       mol_type = other DNA
                       organism = synthetic construct
SEQUENCE: 271
ttagggataa cagggtaatc ggtgcccagg tcagtggatc                           40

SEQ ID NO: 272         moltype = DNA  length = 43
FEATURE                Location/Qualifiers
source                 1..43
                       mol_type = other DNA
                       organism = synthetic construct
SEQUENCE: 272
ttagggataa cagggtaatc ttcaaattct ggttgaaaga tgg                       43

SEQ ID NO: 273         moltype = DNA  length = 40
FEATURE                Location/Qualifiers
source                 1..40
                       mol_type = other DNA
                       organism = synthetic construct
SEQUENCE: 273
ttagggataa cagggtaatc gtgcaggcca acttgttcag                           40

SEQ ID NO: 274         moltype = DNA  length = 41
FEATURE                Location/Qualifiers
source                 1..41
                       mol_type = other DNA
                       organism = synthetic construct
SEQUENCE: 274
ttagggataa cagggtaatc catgtgatgt catctctcct c                         41

SEQ ID NO: 275         moltype = DNA  length = 40
FEATURE                Location/Qualifiers
source                 1..40
                       mol_type = other DNA
                       organism = synthetic construct
SEQUENCE: 275
ttagggataa cagggtaatc gctgcctttg accatgaagg                           40

SEQ ID NO: 276         moltype = DNA  length = 43
FEATURE                Location/Qualifiers
source                 1..43
                       mol_type = other DNA
                       organism = synthetic construct
SEQUENCE: 276
ttagggataa cagggtaatc gaaccatctt ttaactcagg tac                       43

SEQ ID NO: 277         moltype = DNA  length = 41
FEATURE                Location/Qualifiers
source                 1..41
                       mol_type = other DNA
                       organism = synthetic construct
SEQUENCE: 277
ttagggataa cagggtaatc acggcatttt gagtgttaga c                         41

SEQ ID NO: 278         moltype = DNA  length = 43
FEATURE                Location/Qualifiers
source                 1..43
                       mol_type = other DNA
                       organism = synthetic construct
SEQUENCE: 278
ttagggataa cagggtaatc gcctcagatt cacttttatc acc                       43

SEQ ID NO: 279         moltype = DNA  length = 40
FEATURE                Location/Qualifiers
source                 1..40
                       mol_type = other DNA
                       organism = synthetic construct
SEQUENCE: 279
ttagggataa cagggtaatc ctccaccgct tcttgtcctg                           40
```

```
SEQ ID NO: 280          moltype = DNA  length = 43
FEATURE                 Location/Qualifiers
source                  1..43
                        mol_type = other DNA
                        organism = synthetic construct
SEQUENCE: 280
ttagggataa cagggtaatc tactgcctct tgcttctctt ttc                     43

SEQ ID NO: 281          moltype = DNA  length = 41
FEATURE                 Location/Qualifiers
source                  1..41
                        mol_type = other DNA
                        organism = synthetic construct
SEQUENCE: 281
ttagggataa cagggtaatc agaggtgggc ccaggggtca g                       41

SEQ ID NO: 282          moltype = DNA  length = 42
FEATURE                 Location/Qualifiers
source                  1..42
                        mol_type = other DNA
                        organism = synthetic construct
SEQUENCE: 282
ttagggataa cagggtaatc ttgccacagg tctccccaag gc                      42

SEQ ID NO: 283          moltype = DNA  length = 41
FEATURE                 Location/Qualifiers
source                  1..41
                        mol_type = other DNA
                        organism = synthetic construct
SEQUENCE: 283
ttagggataa cagggtaatc ccttaacccc tcctcccaga g                       41

SEQ ID NO: 284          moltype = DNA  length = 40
FEATURE                 Location/Qualifiers
source                  1..40
                        mol_type = other DNA
                        organism = synthetic construct
SEQUENCE: 284
ttagggataa cagggtaatc ggtccccagg cctctgattc                         40

SEQ ID NO: 285          moltype = DNA  length = 40
FEATURE                 Location/Qualifiers
source                  1..40
                        mol_type = other DNA
                        organism = synthetic construct
SEQUENCE: 285
ttagggataa cagggtaatc gccctgtcgt ctctccagcc                         40

SEQ ID NO: 286          moltype = DNA  length = 40
FEATURE                 Location/Qualifiers
source                  1..40
                        mol_type = other DNA
                        organism = synthetic construct
SEQUENCE: 286
ttagggataa cagggtaatc ctgttcactt gtgccctgac                         40

SEQ ID NO: 287          moltype = DNA  length = 41
FEATURE                 Location/Qualifiers
source                  1..41
                        mol_type = other DNA
                        organism = synthetic construct
SEQUENCE: 287
ttagggataa cagggtaatc atacggccag gcattgaagt c                       41

SEQ ID NO: 288          moltype = DNA  length = 40
FEATURE                 Location/Qualifiers
source                  1..40
                        mol_type = other DNA
                        organism = synthetic construct
SEQUENCE: 288
ttagggataa cagggtaatc tgccctggta ggttttctgg                         40

SEQ ID NO: 289          moltype = DNA  length = 41
FEATURE                 Location/Qualifiers
source                  1..41
                        mol_type = other DNA
                        organism = synthetic construct
SEQUENCE: 289
ttagggataa cagggtaatc ccagatgaag ctcccagaat g                       41
```

```
SEQ ID NO: 290          moltype = DNA  length = 40
FEATURE                 Location/Qualifiers
source                  1..40
                        mol_type = other DNA
                        organism = synthetic construct
SEQUENCE: 290
ttagggataa cagggtaatc cctctgactg ctcttttcac                        40

SEQ ID NO: 291          moltype = DNA  length = 40
FEATURE                 Location/Qualifiers
source                  1..40
                        mol_type = other DNA
                        organism = synthetic construct
SEQUENCE: 291
ttagggataa cagggtaatc tccaggtccc cagcccaacc                        40

SEQ ID NO: 292          moltype = DNA  length = 40
FEATURE                 Location/Qualifiers
source                  1..40
                        mol_type = other DNA
                        organism = synthetic construct
SEQUENCE: 292
ttagggataa cagggtaatc ggaagcgaaa attccatggg                        40

SEQ ID NO: 293          moltype = DNA  length = 43
FEATURE                 Location/Qualifiers
source                  1..43
                        mol_type = other DNA
                        organism = synthetic construct
SEQUENCE: 293
ttagggataa cagggtaatc cgcttcccac aggtctctgc tag                    43

SEQ ID NO: 294          moltype = DNA  length = 40
FEATURE                 Location/Qualifiers
source                  1..40
                        mol_type = other DNA
                        organism = synthetic construct
SEQUENCE: 294
ttagggataa cagggtaatc aagtgtctca tgctggatcc                        40

SEQ ID NO: 295          moltype = DNA  length = 40
FEATURE                 Location/Qualifiers
source                  1..40
                        mol_type = other DNA
                        organism = synthetic construct
SEQUENCE: 295
ttagggataa cagggtaatc ttgtggagtg caagtgaaag                        40

SEQ ID NO: 296          moltype = DNA  length = 42
FEATURE                 Location/Qualifiers
source                  1..42
                        mol_type = other DNA
                        organism = synthetic construct
SEQUENCE: 296
ttagggataa cagggtaatc tgtacatggg aaaacataac ct                     42

SEQ ID NO: 297          moltype = DNA  length = 42
FEATURE                 Location/Qualifiers
source                  1..42
                        mol_type = other DNA
                        organism = synthetic construct
SEQUENCE: 297
ttagggataa cagggtaatc ggattgcaga ttgggccttg gg                     42

SEQ ID NO: 298          moltype = DNA  length = 40
FEATURE                 Location/Qualifiers
source                  1..40
                        mol_type = other DNA
                        organism = synthetic construct
SEQUENCE: 298
ttagggataa cagggtaatc cggcccccaa cgctgcccct                        40

SEQ ID NO: 299          moltype = DNA  length = 40
FEATURE                 Location/Qualifiers
source                  1..40
                        mol_type = other DNA
                        organism = synthetic construct
SEQUENCE: 299
```

```
ttagggataa cagggtaatc ggctttggtg agatccattg                    40

SEQ ID NO: 300          moltype = DNA  length = 40
FEATURE                 Location/Qualifiers
source                  1..40
                        mol_type = other DNA
                        organism = synthetic construct
SEQUENCE: 300
ttagggataa cagggtaatc tggttattcc agagggactg                    40

SEQ ID NO: 301          moltype = DNA  length = 40
FEATURE                 Location/Qualifiers
source                  1..40
                        mol_type = other DNA
                        organism = synthetic construct
SEQUENCE: 301
ttagggataa cagggtaatc tggaataacc agctgtcctc                    40

SEQ ID NO: 302          moltype = DNA  length = 40
FEATURE                 Location/Qualifiers
source                  1..40
                        mol_type = other DNA
                        organism = synthetic construct
SEQUENCE: 302
ttagggataa cagggtaatc atccctaaca acacagaagc                    40

SEQ ID NO: 303          moltype = DNA  length = 46
FEATURE                 Location/Qualifiers
source                  1..46
                        mol_type = other DNA
                        organism = synthetic construct
SEQUENCE: 303
ttagggataa cagggtaatc ctagagtttt tccaagaacc aagttc             46

SEQ ID NO: 304          moltype = DNA  length = 40
FEATURE                 Location/Qualifiers
source                  1..40
                        mol_type = other DNA
                        organism = synthetic construct
SEQUENCE: 304
ttagggataa cagggtaatc cggcctccct ctggaaatcc                    40

SEQ ID NO: 305          moltype = DNA  length = 40
FEATURE                 Location/Qualifiers
source                  1..40
                        mol_type = other DNA
                        organism = synthetic construct
SEQUENCE: 305
ttagggataa cagggtaatc caaatatggt cgacggtcca                    40

SEQ ID NO: 306          moltype = DNA  length = 40
FEATURE                 Location/Qualifiers
source                  1..40
                        mol_type = other DNA
                        organism = synthetic construct
SEQUENCE: 306
ttagggataa cagggtaatc cgtcagggac acaactgcca                    40

SEQ ID NO: 307          moltype = DNA  length = 40
FEATURE                 Location/Qualifiers
source                  1..40
                        mol_type = other DNA
                        organism = synthetic construct
SEQUENCE: 307
ttagggataa cagggtaatc aacctcagcc cgaccaagga                    40

SEQ ID NO: 308          moltype = DNA  length = 40
FEATURE                 Location/Qualifiers
source                  1..40
                        mol_type = other DNA
                        organism = synthetic construct
SEQUENCE: 308
ttagggataa cagggtaatc tttctttctg cctcatgctc                    40

SEQ ID NO: 309          moltype = DNA  length = 40
FEATURE                 Location/Qualifiers
source                  1..40
                        mol_type = other DNA
                        organism = synthetic construct
```

```
SEQUENCE: 309
ttagggataa cagggtaatc gtggctcaag tgggctgaaa                    40

SEQ ID NO: 310          moltype = DNA  length = 43
FEATURE                 Location/Qualifiers
source                  1..43
                        mol_type = other DNA
                        organism = synthetic construct
SEQUENCE: 310
ttagggataa cagggtaatc tttggtcagc agcaggagag ctt                43

SEQ ID NO: 311          moltype = DNA  length = 40
FEATURE                 Location/Qualifiers
source                  1..40
                        mol_type = other DNA
                        organism = synthetic construct
SEQUENCE: 311
ttagggataa cagggtaatc actttccaag ttgggcatat                    40

SEQ ID NO: 312          moltype = DNA  length = 40
FEATURE                 Location/Qualifiers
source                  1..40
                        mol_type = other DNA
                        organism = synthetic construct
SEQUENCE: 312
ttagggataa cagggtaatc ggacatgagg gcctccttct                    40

SEQ ID NO: 313          moltype = DNA  length = 41
FEATURE                 Location/Qualifiers
source                  1..41
                        mol_type = other DNA
                        organism = synthetic construct
SEQUENCE: 313
ttagggataa cagggtaatc atcctccttg cccagaccaa a                  41

SEQ ID NO: 314          moltype = DNA  length = 46
FEATURE                 Location/Qualifiers
source                  1..46
                        mol_type = other DNA
                        organism = synthetic construct
SEQUENCE: 314
ttagggataa cagggtaatc cctcatagct ctcgatgatc ttccag             46

SEQ ID NO: 315          moltype = DNA  length = 40
FEATURE                 Location/Qualifiers
source                  1..40
                        mol_type = other DNA
                        organism = synthetic construct
SEQUENCE: 315
ttagggataa cagggtaatc gatggacatg caggcgacca                    40

SEQ ID NO: 316          moltype = DNA  length = 40
FEATURE                 Location/Qualifiers
source                  1..40
                        mol_type = other DNA
                        organism = synthetic construct
SEQUENCE: 316
ttagggataa cagggtaatc gcaccgtcac cttgtggaag                    40

SEQ ID NO: 317          moltype = DNA  length = 40
FEATURE                 Location/Qualifiers
source                  1..40
                        mol_type = other DNA
                        organism = synthetic construct
SEQUENCE: 317
ttagggataa cagggtaatc cagagccgtt gatgaatgtc                    40

SEQ ID NO: 318          moltype = DNA  length = 40
FEATURE                 Location/Qualifiers
source                  1..40
                        mol_type = other DNA
                        organism = synthetic construct
SEQUENCE: 318
ttagggataa cagggtaatc gcaaggatcc agaggaggaa                    40

SEQ ID NO: 319          moltype = DNA  length = 40
FEATURE                 Location/Qualifiers
source                  1..40
                        mol_type = other DNA
```

```
                        organism = synthetic construct
SEQUENCE: 319
ttagggataa cagggtaatc tgccaacacc acctgcccaa                          40

SEQ ID NO: 320          moltype = DNA  length = 40
FEATURE                 Location/Qualifiers
source                  1..40
                        mol_type = other DNA
                        organism = synthetic construct
SEQUENCE: 320
ttagggataa cagggtaatc gcaaccctgc ttgcaggatg                          40

SEQ ID NO: 321          moltype = DNA  length = 41
FEATURE                 Location/Qualifiers
source                  1..41
                        mol_type = other DNA
                        organism = synthetic construct
SEQUENCE: 321
ttagggataa cagggtaatc caccacagag tccattatga t                        41

SEQ ID NO: 322          moltype = DNA  length = 41
FEATURE                 Location/Qualifiers
source                  1..41
                        mol_type = other DNA
                        organism = synthetic construct
SEQUENCE: 322
ttagggataa cagggtaatc ccatcttttc tggggatgtc c                        41

SEQ ID NO: 323          moltype = DNA  length = 45
FEATURE                 Location/Qualifiers
source                  1..45
                        mol_type = other DNA
                        organism = synthetic construct
SEQUENCE: 323
ttagggataa cagggtaatc gttatctgtt tctttctcct ctgaa                    45

SEQ ID NO: 324          moltype = DNA  length = 40
FEATURE                 Location/Qualifiers
source                  1..40
                        mol_type = other DNA
                        organism = synthetic construct
SEQUENCE: 324
ttagggataa cagggtaatc gaaggactcc acttccacag                          40

SEQ ID NO: 325          moltype = DNA  length = 40
FEATURE                 Location/Qualifiers
source                  1..40
                        mol_type = other DNA
                        organism = synthetic construct
SEQUENCE: 325
ttagggataa cagggtaatc tcagcctcaa cgagtgcttc                          40

SEQ ID NO: 326          moltype = DNA  length = 40
FEATURE                 Location/Qualifiers
source                  1..40
                        mol_type = other DNA
                        organism = synthetic construct
SEQUENCE: 326
ttagggataa cagggtaatc gccacgagtt gttgaggaag                          40

SEQ ID NO: 327          moltype = DNA  length = 40
FEATURE                 Location/Qualifiers
source                  1..40
                        mol_type = other DNA
                        organism = synthetic construct
SEQUENCE: 327
ttagggataa cagggtaatc ccctgcccac tgtgttactg                          40

SEQ ID NO: 328          moltype = DNA  length = 42
FEATURE                 Location/Qualifiers
source                  1..42
                        mol_type = other DNA
                        organism = synthetic construct
SEQUENCE: 328
ttagggataa cagggtaatc tttgttctgg cggtgttttg aa                       42

SEQ ID NO: 329          moltype = DNA  length = 40
FEATURE                 Location/Qualifiers
source                  1..40
```

```
                      mol_type = other DNA
                      organism = synthetic construct
SEQUENCE: 329
ttagggataa cagggtaatc atggcatcaa agcagaggac                        40

SEQ ID NO: 330        moltype = DNA  length = 41
FEATURE               Location/Qualifiers
source                1..41
                      mol_type = other DNA
                      organism = synthetic construct
SEQUENCE: 330
ttagggataa cagggtaatc aagtctggct tcttggtcgt g                      41

SEQ ID NO: 331        moltype = DNA  length = 43
FEATURE               Location/Qualifiers
source                1..43
                      mol_type = other DNA
                      organism = synthetic construct
SEQUENCE: 331
ttagggataa cagggtaatc actgcatagg ggtcttctta atc                    43

SEQ ID NO: 332        moltype = DNA  length = 40
FEATURE               Location/Qualifiers
source                1..40
                      mol_type = other DNA
                      organism = synthetic construct
SEQUENCE: 332
ttagggataa cagggtaatc ggcctgctta tctgttcctc                        40

SEQ ID NO: 333        moltype = DNA  length = 41
FEATURE               Location/Qualifiers
source                1..41
                      mol_type = other DNA
                      organism = synthetic construct
SEQUENCE: 333
ttagggataa cagggtaatc gatgtgctgg gtccttttca g                      41

SEQ ID NO: 334        moltype = DNA  length = 40
FEATURE               Location/Qualifiers
source                1..40
                      mol_type = other DNA
                      organism = synthetic construct
SEQUENCE: 334
ttagggataa cagggtaatc aaacgagaag cacatcaacc                        40

SEQ ID NO: 335        moltype = DNA  length = 41
FEATURE               Location/Qualifiers
source                1..41
                      mol_type = other DNA
                      organism = synthetic construct
SEQUENCE: 335
ttagggataa cagggtaatc aaaccaaaca acttccacct c                      41

SEQ ID NO: 336        moltype = DNA  length = 41
FEATURE               Location/Qualifiers
source                1..41
                      mol_type = other DNA
                      organism = synthetic construct
SEQUENCE: 336
ttagggataa cagggtaatc cctttcggaa gagatgtcta a                      41

SEQ ID NO: 337        moltype = DNA  length = 42
FEATURE               Location/Qualifiers
source                1..42
                      mol_type = other DNA
                      organism = synthetic construct
SEQUENCE: 337
ttagggataa cagggtaatc aggacaggta taaaggaaac ac                     42

SEQ ID NO: 338        moltype = DNA  length = 42
FEATURE               Location/Qualifiers
source                1..42
                      mol_type = other DNA
                      organism = synthetic construct
SEQUENCE: 338
ttagggataa cagggtaatc cttctgtgag ctccaaacca ag                     42

SEQ ID NO: 339        moltype = DNA  length = 40
FEATURE               Location/Qualifiers
```

```
source                  1..40
                        mol_type = other DNA
                        organism = synthetic construct
SEQUENCE: 339
ttagggataa cagggtaatc ggaggggtgc agcattggtg                      40

SEQ ID NO: 340          moltype = DNA  length = 44
FEATURE                 Location/Qualifiers
source                  1..44
                        mol_type = other DNA
                        organism = synthetic construct
SEQUENCE: 340
ttagggataa cagggtaatc aagctttgtt ttcttcacat tcta                 44

SEQ ID NO: 341          moltype = DNA  length = 40
FEATURE                 Location/Qualifiers
source                  1..40
                        mol_type = other DNA
                        organism = synthetic construct
SEQUENCE: 341
ttagggataa cagggtaatc caagaccaac ctccatgtgg                      40

SEQ ID NO: 342          moltype = DNA  length = 41
FEATURE                 Location/Qualifiers
source                  1..41
                        mol_type = other DNA
                        organism = synthetic construct
SEQUENCE: 342
ttagggataa cagggtaatc ttgattgggg aactgtaacg c                    41

SEQ ID NO: 343          moltype = DNA  length = 41
FEATURE                 Location/Qualifiers
source                  1..41
                        mol_type = other DNA
                        organism = synthetic construct
SEQUENCE: 343
ttagggataa cagggtaatc ttggagggca gcctcttcac c                    41

SEQ ID NO: 344          moltype = DNA  length = 41
FEATURE                 Location/Qualifiers
source                  1..41
                        mol_type = other DNA
                        organism = synthetic construct
SEQUENCE: 344
ttagggataa cagggtaatc tttggctctg caccctaacg g                    41

SEQ ID NO: 345          moltype = DNA  length = 38
FEATURE                 Location/Qualifiers
source                  1..38
                        mol_type = other DNA
                        organism = synthetic construct
SEQUENCE: 345
ttagggataa cagggtaatc agcctctcca cgctccct                        38

SEQ ID NO: 346          moltype = DNA  length = 40
FEATURE                 Location/Qualifiers
source                  1..40
                        mol_type = other DNA
                        organism = synthetic construct
SEQUENCE: 346
ttagggataa cagggtaatc acaggcctga gagtggagct                      40

SEQ ID NO: 347          moltype = DNA  length = 40
FEATURE                 Location/Qualifiers
source                  1..40
                        mol_type = other DNA
                        organism = synthetic construct
SEQUENCE: 347
ttagggataa cagggtaatc ctcaactcca ggccaggtgt                      40

SEQ ID NO: 348          moltype = DNA  length = 38
FEATURE                 Location/Qualifiers
source                  1..38
                        mol_type = other DNA
                        organism = synthetic construct
SEQUENCE: 348
ttagggataa cagggtaatc aggtcctcgt gcctgcca                        38

SEQ ID NO: 349          moltype = DNA  length = 39
```

```
FEATURE                Location/Qualifiers
source                 1..39
                       mol_type = other DNA
                       organism = synthetic construct
SEQUENCE: 349
ttagggataa cagggtaatc ggcacgagga cctgtggga                      39

SEQ ID NO: 350         moltype = DNA  length = 43
FEATURE                Location/Qualifiers
source                 1..43
                       mol_type = other DNA
                       organism = synthetic construct
SEQUENCE: 350
ttagggataa cagggtaatc gcccttttg tggggtagga cag                  43

SEQ ID NO: 351         moltype = DNA  length = 42
FEATURE                Location/Qualifiers
source                 1..42
                       mol_type = other DNA
                       organism = synthetic construct
SEQUENCE: 351
ttagggataa cagggtaatc ctctagctcc ttgtcggtgg tg                  42

SEQ ID NO: 352         moltype = DNA  length = 38
FEATURE                Location/Qualifiers
source                 1..38
                       mol_type = other DNA
                       organism = synthetic construct
SEQUENCE: 352
ttagggataa cagggtaatc tgcccgcctc gtcagcct                       38

SEQ ID NO: 353         moltype = DNA  length = 42
FEATURE                Location/Qualifiers
source                 1..42
                       mol_type = other DNA
                       organism = synthetic construct
SEQUENCE: 353
ttagggataa cagggtaatc gttggagctc atggacgcgt tg                  42

SEQ ID NO: 354         moltype = DNA  length = 41
FEATURE                Location/Qualifiers
source                 1..41
                       mol_type = other DNA
                       organism = synthetic construct
SEQUENCE: 354
ttagggataa cagggtaatc tcacagctct cagggaccca a                   41

SEQ ID NO: 355         moltype = DNA  length = 40
FEATURE                Location/Qualifiers
source                 1..40
                       mol_type = other DNA
                       organism = synthetic construct
SEQUENCE: 355
ttagggataa cagggtaatc caggacctcc acctctgagc                     40

SEQ ID NO: 356         moltype = DNA  length = 39
FEATURE                Location/Qualifiers
source                 1..39
                       mol_type = other DNA
                       organism = synthetic construct
SEQUENCE: 356
ttagggataa cagggtaatc agggagcccg acgcgtaca                      39

SEQ ID NO: 357         moltype = DNA  length = 41
FEATURE                Location/Qualifiers
source                 1..41
                       mol_type = other DNA
                       organism = synthetic construct
SEQUENCE: 357
ttagggataa cagggtaatc cttgacttgc cggaagagcc t                   41

SEQ ID NO: 358         moltype = DNA  length = 38
FEATURE                Location/Qualifiers
source                 1..38
                       mol_type = other DNA
                       organism = synthetic construct
SEQUENCE: 358
ttagggataa cagggtaatc ctggtggagg cgctggac                       38
```

```
SEQ ID NO: 359          moltype = DNA  length = 44
FEATURE                 Location/Qualifiers
source                  1..44
                        mol_type = other DNA
                        organism = synthetic construct
SEQUENCE: 359
ttagggataa cagggtaatc tgactttcca ttctctgctg gatg                     44

SEQ ID NO: 360          moltype = DNA  length = 43
FEATURE                 Location/Qualifiers
source                  1..43
                        mol_type = other DNA
                        organism = synthetic construct
SEQUENCE: 360
ttagggataa cagggtaatc agatgagtat gcctgccgtg tga                      43

SEQ ID NO: 361          moltype = DNA  length = 41
FEATURE                 Location/Qualifiers
source                  1..41
                        mol_type = other DNA
                        organism = synthetic construct
SEQUENCE: 361
ttagggataa cagggtaatc gttcagcaaa tgccagtagg t                        41

SEQ ID NO: 362          moltype = DNA  length = 45
FEATURE                 Location/Qualifiers
source                  1..45
                        mol_type = other DNA
                        organism = synthetic construct
SEQUENCE: 362
ttagggataa cagggtaatc accatactct accacatata ggtcc                    45

SEQ ID NO: 363          moltype = DNA  length = 40
FEATURE                 Location/Qualifiers
source                  1..40
                        mol_type = other DNA
                        organism = synthetic construct
SEQUENCE: 363
ttagggataa cagggtaatc aggtgactgg atccacaacc                          40

SEQ ID NO: 364          moltype = DNA  length = 45
FEATURE                 Location/Qualifiers
source                  1..45
                        mol_type = other DNA
                        organism = synthetic construct
SEQUENCE: 364
ttagggataa cagggtaatc gagattagat cctgaggaaa accat                    45

SEQ ID NO: 365          moltype = DNA  length = 45
FEATURE                 Location/Qualifiers
source                  1..45
                        mol_type = other DNA
                        organism = synthetic construct
SEQUENCE: 365
ttagggataa cagggtaatc tgggagccat cttattatgc cttgg                    45

SEQ ID NO: 366          moltype = DNA  length = 44
FEATURE                 Location/Qualifiers
source                  1..44
                        mol_type = other DNA
                        organism = synthetic construct
SEQUENCE: 366
ttagggataa cagggtaatc ctttgagttt gtatcttgga tgcc                     44

SEQ ID NO: 367          moltype = DNA  length = 45
FEATURE                 Location/Qualifiers
source                  1..45
                        mol_type = other DNA
                        organism = synthetic construct
SEQUENCE: 367
ttagggataa cagggtaatc cgcatcaata caaacttgcg cacat                    45

SEQ ID NO: 368          moltype = DNA  length = 42
FEATURE                 Location/Qualifiers
source                  1..42
                        mol_type = other DNA
                        organism = synthetic construct
SEQUENCE: 368
ttagggataa cagggtaatc ccatgaaggg tgtcaccaag gc                       42
```

```
SEQ ID NO: 369          moltype = DNA  length = 44
FEATURE                 Location/Qualifiers
source                  1..44
                        mol_type = other DNA
                        organism = synthetic construct
SEQUENCE: 369
ttagggataa cagggtaatc caagactaag taggaccatg tagg                    44

SEQ ID NO: 370          moltype = DNA  length = 43
FEATURE                 Location/Qualifiers
source                  1..43
                        mol_type = other DNA
                        organism = synthetic construct
SEQUENCE: 370
ttagggataa cagggtaatc cctggttatt gagtgagccc caa                     43

SEQ ID NO: 371          moltype = DNA  length = 44
FEATURE                 Location/Qualifiers
source                  1..44
                        mol_type = other DNA
                        organism = synthetic construct
SEQUENCE: 371
ttagggataa cagggtaatc tggtttcaca tcgtccccct tttt                    44

SEQ ID NO: 372          moltype = DNA  length = 41
FEATURE                 Location/Qualifiers
source                  1..41
                        mol_type = other DNA
                        organism = synthetic construct
SEQUENCE: 372
ttagggataa cagggtaatc tgacccctcg gaaaacaccc t                       41

SEQ ID NO: 373          moltype = DNA  length = 40
FEATURE                 Location/Qualifiers
source                  1..40
                        mol_type = other DNA
                        organism = synthetic construct
SEQUENCE: 373
ttagggataa cagggtaatc gcgttgtccc cttcggtcac                         40

SEQ ID NO: 374          moltype = DNA  length = 38
FEATURE                 Location/Qualifiers
source                  1..38
                        mol_type = other DNA
                        organism = synthetic construct
SEQUENCE: 374
ttagggataa cagggtaatc ctggggtggg ctgtgggc                           38

SEQ ID NO: 375          moltype = DNA  length = 40
FEATURE                 Location/Qualifiers
source                  1..40
                        mol_type = other DNA
                        organism = synthetic construct
SEQUENCE: 375
ttagggataa cagggtaatc agcagcagga gaaggatgcc                         40

SEQ ID NO: 376          moltype = DNA  length = 41
FEATURE                 Location/Qualifiers
source                  1..41
                        mol_type = other DNA
                        organism = synthetic construct
SEQUENCE: 376
ttagggataa cagggtaatc ccccgagggc cctcttgaag t                       41

SEQ ID NO: 377          moltype = DNA  length = 46
FEATURE                 Location/Qualifiers
source                  1..46
                        mol_type = other DNA
                        organism = synthetic construct
SEQUENCE: 377
ttagggataa cagggtaatc actggattta gagtctctca gctggt                  46

SEQ ID NO: 378          moltype = DNA  length = 43
FEATURE                 Location/Qualifiers
source                  1..43
                        mol_type = other DNA
                        organism = synthetic construct
SEQUENCE: 378
```

```
ttagggataa cagggtaatc tgatggctca aacacagcga cct                   43

SEQ ID NO: 379          moltype = DNA  length = 40
FEATURE                 Location/Qualifiers
source                  1..40
                        mol_type = other DNA
                        organism = synthetic construct
SEQUENCE: 379
ttagggataa cagggtaatc gcacgatgtc ccggcgcttg                       40

SEQ ID NO: 380          moltype = DNA  length = 56
FEATURE                 Location/Qualifiers
source                  1..56
                        mol_type = other DNA
                        organism = synthetic construct
SEQUENCE: 380
gtgactggag ttcagacgtg tgctcttccg atctgatctg ttagaaacct ctccag     56

SEQ ID NO: 381          moltype = DNA  length = 58
FEATURE                 Location/Qualifiers
source                  1..58
                        mol_type = other DNA
                        organism = synthetic construct
SEQUENCE: 381
gtgactggag ttcagacgtg tgctcttccg atctatgtaa ctttgtatcc tgttcctc   58

SEQ ID NO: 382          moltype = DNA  length = 60
FEATURE                 Location/Qualifiers
source                  1..60
                        mol_type = other DNA
                        organism = synthetic construct
SEQUENCE: 382
gtgactggag ttcagacgtg tgctcttccg atctgccgtt gtacactcat cttcctaggg 60

SEQ ID NO: 383          moltype = DNA  length = 54
FEATURE                 Location/Qualifiers
source                  1..54
                        mol_type = other DNA
                        organism = synthetic construct
SEQUENCE: 383
gtgactggag ttcagacgtg tgctcttccg atctatggat ccagacaact gttc       54

SEQ ID NO: 384          moltype = DNA  length = 57
FEATURE                 Location/Qualifiers
source                  1..57
                        mol_type = other DNA
                        organism = synthetic construct
SEQUENCE: 384
gtgactggag ttcagacgtg tgctcttccg atctgcttgc tctgatagga aaatgag    57

SEQ ID NO: 385          moltype = DNA  length = 54
FEATURE                 Location/Qualifiers
source                  1..54
                        mol_type = other DNA
                        organism = synthetic construct
SEQUENCE: 385
gtgactggag ttcagacgtg tgctcttccg atctggagaa gctcccaacc aagc       54

SEQ ID NO: 386          moltype = DNA  length = 55
FEATURE                 Location/Qualifiers
source                  1..55
                        mol_type = other DNA
                        organism = synthetic construct
SEQUENCE: 386
gtgactggag ttcagacgtg tgctcttccg atctcagacc atgagaggcc ctgcg      55

SEQ ID NO: 387          moltype = DNA  length = 60
FEATURE                 Location/Qualifiers
source                  1..60
                        mol_type = other DNA
                        organism = synthetic construct
SEQUENCE: 387
gtgactggag ttcagacgtg tgctcttccg atctgttaac gtcttccttc tctctctgtc 60

SEQ ID NO: 388          moltype = DNA  length = 55
FEATURE                 Location/Qualifiers
source                  1..55
                        mol_type = other DNA
                        organism = synthetic construct
```

```
SEQUENCE: 388
gtgactggag ttcagacgtg tgctcttccg atctcccaca cagcaaagca gaaac       55

SEQ ID NO: 389          moltype = DNA  length = 56
FEATURE                 Location/Qualifiers
source                  1..56
                        mol_type = other DNA
                        organism = synthetic construct
SEQUENCE: 389
gtgactggag ttcagacgtg tgctcttccg atcttccttc tggccaccat gcgaag      56

SEQ ID NO: 390          moltype = DNA  length = 56
FEATURE                 Location/Qualifiers
source                  1..56
                        mol_type = other DNA
                        organism = synthetic construct
SEQUENCE: 390
gtgactggag ttcagacgtg tgctcttccg atctagccaa tattgtcttt gtgttc      56

SEQ ID NO: 391          moltype = DNA  length = 54
FEATURE                 Location/Qualifiers
source                  1..54
                        mol_type = other DNA
                        organism = synthetic construct
SEQUENCE: 391
gtgactggag ttcagacgtg tgctcttccg atcttgaaaa caccgcagca tgtc        54

SEQ ID NO: 392          moltype = DNA  length = 57
FEATURE                 Location/Qualifiers
source                  1..57
                        mol_type = other DNA
                        organism = synthetic construct
SEQUENCE: 392
gtgactggag ttcagacgtg tgctcttccg atctgaaaat gctggctgac ctaaagc     57

SEQ ID NO: 393          moltype = DNA  length = 54
FEATURE                 Location/Qualifiers
source                  1..54
                        mol_type = other DNA
                        organism = synthetic construct
SEQUENCE: 393
gtgactggag ttcagacgtg tgctcttccg atctgtggct acatgttcct gatc        54

SEQ ID NO: 394          moltype = DNA  length = 55
FEATURE                 Location/Qualifiers
source                  1..55
                        mol_type = other DNA
                        organism = synthetic construct
SEQUENCE: 394
gtgactggag ttcagacgtg tgctcttccg atctgaagga taggacaggg tgggc       55

SEQ ID NO: 395          moltype = DNA  length = 60
FEATURE                 Location/Qualifiers
source                  1..60
                        mol_type = other DNA
                        organism = synthetic construct
SEQUENCE: 395
gtgactggag ttcagacgtg tgctcttccg atctcatacc ctctcagcgt acccttgtcc  60

SEQ ID NO: 396          moltype = DNA  length = 56
FEATURE                 Location/Qualifiers
source                  1..56
                        mol_type = other DNA
                        organism = synthetic construct
SEQUENCE: 396
gtgactggag ttcagacgtg tgctcttccg atctgggttt gctccggaga gacctg      56

SEQ ID NO: 397          moltype = DNA  length = 59
FEATURE                 Location/Qualifiers
source                  1..59
                        mol_type = other DNA
                        organism = synthetic construct
SEQUENCE: 397
gtgactggag ttcagacgtg tgctcttccg atctttggat catattcgtc cacaaaatg   59

SEQ ID NO: 398          moltype = DNA  length = 54
FEATURE                 Location/Qualifiers
source                  1..54
                        mol_type = other DNA
```

```
                        organism = synthetic construct
SEQUENCE: 398
gtgactggag ttcagacgtg tgctcttccg atctggcctg ctgaaaatga ctga       54

SEQ ID NO: 399          moltype = DNA  length = 54
FEATURE                 Location/Qualifiers
source                  1..54
                        mol_type = other DNA
                        organism = synthetic construct
SEQUENCE: 399
gtgactggag ttcagacgtg tgctcttccg atcttcccca gtcctcatgt actg       54

SEQ ID NO: 400          moltype = DNA  length = 59
FEATURE                 Location/Qualifiers
source                  1..59
                        mol_type = other DNA
                        organism = synthetic construct
SEQUENCE: 400
gtgactggag ttcagacgtg tgctcttccg atctaggaag caagtagtaa ttgatggag  59

SEQ ID NO: 401          moltype = DNA  length = 54
FEATURE                 Location/Qualifiers
source                  1..54
                        mol_type = other DNA
                        organism = synthetic construct
SEQUENCE: 401
gtgactggag ttcagacgtg tgctcttccg atcttgggca ctgggtcaaa gtct       54

SEQ ID NO: 402          moltype = DNA  length = 58
FEATURE                 Location/Qualifiers
source                  1..58
                        mol_type = other DNA
                        organism = synthetic construct
SEQUENCE: 402
gtgactggag ttcagacgtg tgctcttccg atctcaaccc actgaggtat atgtatag   58

SEQ ID NO: 403          moltype = DNA  length = 54
FEATURE                 Location/Qualifiers
source                  1..54
                        mol_type = other DNA
                        organism = synthetic construct
SEQUENCE: 403
gtgactggag ttcagacgtg tgctcttccg atctacgcag tgctaaccaa gttc       54

SEQ ID NO: 404          moltype = DNA  length = 60
FEATURE                 Location/Qualifiers
source                  1..60
                        mol_type = other DNA
                        organism = synthetic construct
SEQUENCE: 404
gtgactggag ttcagacgtg tgctcttccg atctgcaaac cacaaaagta tactccatgg 60

SEQ ID NO: 405          moltype = DNA  length = 60
FEATURE                 Location/Qualifiers
source                  1..60
                        mol_type = other DNA
                        organism = synthetic construct
SEQUENCE: 405
gtgactggag ttcagacgtg tgctcttccg atctgtaggc tggatgaaaa attcacagtc 60

SEQ ID NO: 406          moltype = DNA  length = 58
FEATURE                 Location/Qualifiers
source                  1..58
                        mol_type = other DNA
                        organism = synthetic construct
SEQUENCE: 406
gtgactggag ttcagacgtg tgctcttccg atctctgact tggtggtaaa cttttgag   58

SEQ ID NO: 407          moltype = DNA  length = 59
FEATURE                 Location/Qualifiers
source                  1..59
                        mol_type = other DNA
                        organism = synthetic construct
SEQUENCE: 407
gtgactggag ttcagacgtg tgctcttccg atctaaaatg acaaagaaca gctcaaagc  59

SEQ ID NO: 408          moltype = DNA  length = 57
FEATURE                 Location/Qualifiers
source                  1..57
```

```
                         mol_type = other DNA
                         organism = synthetic construct
SEQUENCE: 408
gtgactggag ttcagacgtg tgctcttccg atctagcact tacctgtgac tccatag     57

SEQ ID NO: 409           moltype = DNA  length = 57
FEATURE                  Location/Qualifiers
source                   1..57
                         mol_type = other DNA
                         organism = synthetic construct
SEQUENCE: 409
gtgactggag ttcagacgtg tgctcttccg atctagcctt agataaaact gagcaag     57

SEQ ID NO: 410           moltype = DNA  length = 57
FEATURE                  Location/Qualifiers
source                   1..57
                         mol_type = other DNA
                         organism = synthetic construct
SEQUENCE: 410
gtgactggag ttcagacgtg tgctcttccg atctccaata ttatggatcc caactgc     57

SEQ ID NO: 411           moltype = DNA  length = 56
FEATURE                  Location/Qualifiers
source                   1..56
                         mol_type = other DNA
                         organism = synthetic construct
SEQUENCE: 411
gtgactggag ttcagacgtg tgctcttccg atctctgctt ctgtcatatc atccag      56

SEQ ID NO: 412           moltype = DNA  length = 56
FEATURE                  Location/Qualifiers
source                   1..56
                         mol_type = other DNA
                         organism = synthetic construct
SEQUENCE: 412
gtgactggag ttcagacgtg tgctcttccg atctggatca gcgagagtgg caggtg      56

SEQ ID NO: 413           moltype = DNA  length = 55
FEATURE                  Location/Qualifiers
source                   1..55
                         mol_type = other DNA
                         organism = synthetic construct
SEQUENCE: 413
gtgactggag ttcagacgtg tgctcttccg atctccttca tacacctccc caaag       55

SEQ ID NO: 414           moltype = DNA  length = 55
FEATURE                  Location/Qualifiers
source                   1..55
                         mol_type = other DNA
                         organism = synthetic construct
SEQUENCE: 414
gtgactggag ttcagacgtg tgctcttccg atctgggctg cggcatgatc cttgg       55

SEQ ID NO: 415           moltype = DNA  length = 55
FEATURE                  Location/Qualifiers
source                   1..55
                         mol_type = other DNA
                         organism = synthetic construct
SEQUENCE: 415
gtgactggag ttcagacgtg tgctcttccg atcttgcaga acacacagcc cattc       55

SEQ ID NO: 416           moltype = DNA  length = 54
FEATURE                  Location/Qualifiers
source                   1..54
                         mol_type = other DNA
                         organism = synthetic construct
SEQUENCE: 416
gtgactggag ttcagacgtg tgctcttccg atctaggacg gttgaagaaa ttgc        54

SEQ ID NO: 417           moltype = DNA  length = 54
FEATURE                  Location/Qualifiers
source                   1..54
                         mol_type = other DNA
                         organism = synthetic construct
SEQUENCE: 417
gtgactggag ttcagacgtg tgctcttccg atctgactag tttggaacct gcag        54

SEQ ID NO: 418           moltype = DNA  length = 57
FEATURE                  Location/Qualifiers
```

```
source                  1..57
                        mol_type = other DNA
                        organism = synthetic construct
SEQUENCE: 418
gtgactggag ttcagacgtg tgctcttccg atctatactc tccagaatca gccagtg     57

SEQ ID NO: 419          moltype = DNA  length = 60
FEATURE                 Location/Qualifiers
source                  1..60
                        mol_type = other DNA
                        organism = synthetic construct
SEQUENCE: 419
gtgactggag ttcagacgtg tgctcttccg atctagacac atatgctcct tcagttgagg  60

SEQ ID NO: 420          moltype = DNA  length = 59
FEATURE                 Location/Qualifiers
source                  1..59
                        mol_type = other DNA
                        organism = synthetic construct
SEQUENCE: 420
gtgactggag ttcagacgtg tgctcttccg atctccttct ccgcacattt tacaagatg   59

SEQ ID NO: 421          moltype = DNA  length = 54
FEATURE                 Location/Qualifiers
source                  1..54
                        mol_type = other DNA
                        organism = synthetic construct
SEQUENCE: 421
gtgactggag ttcagacgtg tgctcttccg atcttccacc gccgtgtgca gctg        54

SEQ ID NO: 422          moltype = DNA  length = 55
FEATURE                 Location/Qualifiers
source                  1..55
                        mol_type = other DNA
                        organism = synthetic construct
SEQUENCE: 422
gtgactggag ttcagacgtg tgctcttccg atctccaccg ggtctccaga tgtgc       55

SEQ ID NO: 423          moltype = DNA  length = 58
FEATURE                 Location/Qualifiers
source                  1..58
                        mol_type = other DNA
                        organism = synthetic construct
SEQUENCE: 423
gtgactggag ttcagacgtg tgctcttccg atctaggagc agcgtagaaa ggaagagg    58

SEQ ID NO: 424          moltype = DNA  length = 60
FEATURE                 Location/Qualifiers
source                  1..60
                        mol_type = other DNA
                        organism = synthetic construct
SEQUENCE: 424
gtgactggag ttcagacgtg tgctcttccg atctccaatg tcatgaaatg cagggacatg  60

SEQ ID NO: 425          moltype = DNA  length = 56
FEATURE                 Location/Qualifiers
source                  1..56
                        mol_type = other DNA
                        organism = synthetic construct
SEQUENCE: 425
gtgactggag ttcagacgtg tgctcttccg atctgaggtt ggagattcga gaaatg      56

SEQ ID NO: 426          moltype = DNA  length = 57
FEATURE                 Location/Qualifiers
source                  1..57
                        mol_type = other DNA
                        organism = synthetic construct
SEQUENCE: 426
gtgactggag ttcagacgtg tgctcttccg atctgtcccc gatgtcattc gctgcag     57

SEQ ID NO: 427          moltype = DNA  length = 57
FEATURE                 Location/Qualifiers
source                  1..57
                        mol_type = other DNA
                        organism = synthetic construct
SEQUENCE: 427
gtgactggag ttcagacgtg tgctcttccg atctaccaca gacgcaatca ccaccac     57

SEQ ID NO: 428          moltype = DNA  length = 55
```

```
FEATURE                Location/Qualifiers
source                 1..55
                       mol_type = other DNA
                       organism = synthetic construct
SEQUENCE: 428
gtgactggag ttcagacgtg tgctcttccg atctgatttt actttcccaa atcca       55

SEQ ID NO: 429         moltype = DNA  length = 58
FEATURE                Location/Qualifiers
source                 1..58
                       mol_type = other DNA
                       organism = synthetic construct
SEQUENCE: 429
gtgactggag ttcagacgtg tgctcttccg atctgagtca tcatcattgc tgataacg    58

SEQ ID NO: 430         moltype = DNA  length = 55
FEATURE                Location/Qualifiers
source                 1..55
                       mol_type = other DNA
                       organism = synthetic construct
SEQUENCE: 430
gtgactggag ttcagacgtg tgctcttccg atctcaaaag cagcaagtcc aactg       55

SEQ ID NO: 431         moltype = DNA  length = 60
FEATURE                Location/Qualifiers
source                 1..60
                       mol_type = other DNA
                       organism = synthetic construct
SEQUENCE: 431
gtgactggag ttcagacgtg tgctcttccg atcttgagtc ctcctcacca ctgatgacag  60

SEQ ID NO: 432         moltype = DNA  length = 56
FEATURE                Location/Qualifiers
source                 1..56
                       mol_type = other DNA
                       organism = synthetic construct
SEQUENCE: 432
gtgactggag ttcagacgtg tgctcttccg atctcacgat gtctctcctc ttaatg      56

SEQ ID NO: 433         moltype = DNA  length = 54
FEATURE                Location/Qualifiers
source                 1..54
                       mol_type = other DNA
                       organism = synthetic construct
SEQUENCE: 433
gtgactggag ttcagacgtg tgctcttccg atctccaggc tcgtgtcccc caac        54

SEQ ID NO: 434         moltype = DNA  length = 56
FEATURE                Location/Qualifiers
source                 1..56
                       mol_type = other DNA
                       organism = synthetic construct
SEQUENCE: 434
gtgactggag ttcagacgtg tgctcttccg atctgacagc aggtctcgca gctcac      56

SEQ ID NO: 435         moltype = DNA  length = 60
FEATURE                Location/Qualifiers
source                 1..60
                       mol_type = other DNA
                       organism = synthetic construct
SEQUENCE: 435
gtgactggag ttcagacgtg tgctcttccg atctggacct tggctgcatg aagttttaac  60

SEQ ID NO: 436         moltype = DNA  length = 54
FEATURE                Location/Qualifiers
source                 1..54
                       mol_type = other DNA
                       organism = synthetic construct
SEQUENCE: 436
gtgactggag ttcagacgtg tgctcttccg atctggaatg cctggtttat ttgg        54

SEQ ID NO: 437         moltype = DNA  length = 60
FEATURE                Location/Qualifiers
source                 1..60
                       mol_type = other DNA
                       organism = synthetic construct
SEQUENCE: 437
gtgactggag ttcagacgtg tgctcttccg atctatgtca tcttccacct taaattctgg  60
```

```
SEQ ID NO: 438          moltype = DNA  length = 57
FEATURE                 Location/Qualifiers
source                  1..57
                        mol_type = other DNA
                        organism = synthetic construct
SEQUENCE: 438
gtgactggag ttcagacgtg tgctcttccg atctaagatt ttcaatctcc tcttggg     57

SEQ ID NO: 439          moltype = DNA  length = 60
FEATURE                 Location/Qualifiers
source                  1..60
                        mol_type = other DNA
                        organism = synthetic construct
SEQUENCE: 439
gtgactggag ttcagacgtg tgctcttccg atcttaatat cccatgattg tctatgtttg  60

SEQ ID NO: 440          moltype = DNA  length = 59
FEATURE                 Location/Qualifiers
source                  1..59
                        mol_type = other DNA
                        organism = synthetic construct
SEQUENCE: 440
gtgactggag ttcagacgtg tgctcttccg atcttgacat tcgtctacct cacagtgac   59

SEQ ID NO: 441          moltype = DNA  length = 54
FEATURE                 Location/Qualifiers
source                  1..54
                        mol_type = other DNA
                        organism = synthetic construct
SEQUENCE: 441
gtgactggag ttcagacgtg tgctcttccg atctgtggcc tgtcgtccgg tctg        54

SEQ ID NO: 442          moltype = DNA  length = 56
FEATURE                 Location/Qualifiers
source                  1..56
                        mol_type = other DNA
                        organism = synthetic construct
SEQUENCE: 442
gtgactggag ttcagacgtg tgctcttccg atctctcata gctgtcggcc ccacag      56

SEQ ID NO: 443          moltype = DNA  length = 60
FEATURE                 Location/Qualifiers
source                  1..60
                        mol_type = other DNA
                        organism = synthetic construct
SEQUENCE: 443
gtgactggag ttcagacgtg tgctcttccg atcttcttta aattcaccaa tacctattcc  60

SEQ ID NO: 444          moltype = DNA  length = 54
FEATURE                 Location/Qualifiers
source                  1..54
                        mol_type = other DNA
                        organism = synthetic construct
SEQUENCE: 444
gtgactggag ttcagacgtg tgctcttccg atctggtgct gcccgcctct gacc        54

SEQ ID NO: 445          moltype = DNA  length = 56
FEATURE                 Location/Qualifiers
source                  1..56
                        mol_type = other DNA
                        organism = synthetic construct
SEQUENCE: 445
gtgactggag ttcagacgtg tgctcttccg atctagtgtg tactcttgca tcgtag      56

SEQ ID NO: 446          moltype = DNA  length = 57
FEATURE                 Location/Qualifiers
source                  1..57
                        mol_type = other DNA
                        organism = synthetic construct
SEQUENCE: 446
gtgactggag ttcagacgtg tgctcttccg atctctagtt aggatggggg acatgtc     57

SEQ ID NO: 447          moltype = DNA  length = 58
FEATURE                 Location/Qualifiers
source                  1..58
                        mol_type = other DNA
                        organism = synthetic construct
SEQUENCE: 447
gtgactggag ttcagacgtg tgctcttccg atctaattgc cccgcagcca cccacctc    58
```

```
SEQ ID NO: 448          moltype = DNA  length = 54
FEATURE                 Location/Qualifiers
source                  1..54
                        mol_type = other DNA
                        organism = synthetic construct
SEQUENCE: 448
gtgactggag ttcagacgtg tgctcttccg atctgtgagc agctcagcct cacg       54

SEQ ID NO: 449          moltype = DNA  length = 55
FEATURE                 Location/Qualifiers
source                  1..55
                        mol_type = other DNA
                        organism = synthetic construct
SEQUENCE: 449
gtgactggag ttcagacgtg tgctcttccg atctccagca gcttggcatc aggtc      55

SEQ ID NO: 450          moltype = DNA  length = 57
FEATURE                 Location/Qualifiers
source                  1..57
                        mol_type = other DNA
                        organism = synthetic construct
SEQUENCE: 450
gtgactggag ttcagacgtg tgctcttccg atctgaacaa tgttatgtcg cttgatg    57

SEQ ID NO: 451          moltype = DNA  length = 55
FEATURE                 Location/Qualifiers
source                  1..55
                        mol_type = other DNA
                        organism = synthetic construct
SEQUENCE: 451
gtgactggag ttcagacgtg tgctcttccg atcttccact cacacctgcc tgttg      55

SEQ ID NO: 452          moltype = DNA  length = 54
FEATURE                 Location/Qualifiers
source                  1..54
                        mol_type = other DNA
                        organism = synthetic construct
SEQUENCE: 452
gtgactggag ttcagacgtg tgctcttccg atctggcaaa tgttgatgtc ttgg       54

SEQ ID NO: 453          moltype = DNA  length = 60
FEATURE                 Location/Qualifiers
source                  1..60
                        mol_type = other DNA
                        organism = synthetic construct
SEQUENCE: 453
gtgactggag ttcagacgtg tgctcttccg atctgggcaa acttgtggta gcagtggatg 60

SEQ ID NO: 454          moltype = DNA  length = 56
FEATURE                 Location/Qualifiers
source                  1..56
                        mol_type = other DNA
                        organism = synthetic construct
SEQUENCE: 454
gtgactggag ttcagacgtg tgctcttccg atctctcctg gtctgtggaa cccttc     56

SEQ ID NO: 455          moltype = DNA  length = 55
FEATURE                 Location/Qualifiers
source                  1..55
                        mol_type = other DNA
                        organism = synthetic construct
SEQUENCE: 455
gtgactggag ttcagacgtg tgctcttccg atctctgcag ttctcagctc acagc      55

SEQ ID NO: 456          moltype = DNA  length = 55
FEATURE                 Location/Qualifiers
source                  1..55
                        mol_type = other DNA
                        organism = synthetic construct
SEQUENCE: 456
gtgactggag ttcagacgtg tgctcttccg atctatcctt gctcctgtcc ttggc      55

SEQ ID NO: 457          moltype = DNA  length = 54
FEATURE                 Location/Qualifiers
source                  1..54
                        mol_type = other DNA
                        organism = synthetic construct
SEQUENCE: 457
```

```
gtgactggag ttcagacgtg tgctcttccg atctagccac accccattct tgag        54

SEQ ID NO: 458          moltype = DNA  length = 59
FEATURE                 Location/Qualifiers
source                  1..59
                        mol_type = other DNA
                        organism = synthetic construct
SEQUENCE: 458
gtgactggag ttcagacgtg tgctcttccg atctagaaat cacgcattta tgttttctc   59

SEQ ID NO: 459          moltype = DNA  length = 60
FEATURE                 Location/Qualifiers
source                  1..60
                        mol_type = other DNA
                        organism = synthetic construct
SEQUENCE: 459
gtgactggag ttcagacgtg tgctcttccg atcttctgca tttatgaacc cccagccttg  60

SEQ ID NO: 460          moltype = DNA  length = 56
FEATURE                 Location/Qualifiers
source                  1..56
                        mol_type = other DNA
                        organism = synthetic construct
SEQUENCE: 460
gtgactggag ttcagacgtg tgctcttccg atctgcccag cgtgtcctct ctcctc      56

SEQ ID NO: 461          moltype = DNA  length = 54
FEATURE                 Location/Qualifiers
source                  1..54
                        mol_type = other DNA
                        organism = synthetic construct
SEQUENCE: 461
gtgactggag ttcagacgtg tgctcttccg atctgagggc ccacagagga ggac        54

SEQ ID NO: 462          moltype = DNA  length = 60
FEATURE                 Location/Qualifiers
source                  1..60
                        mol_type = other DNA
                        organism = synthetic construct
SEQUENCE: 462
gtgactggag ttcagacgtg tgctcttccg atctatgcat gaacattttt ctccaccttg  60

SEQ ID NO: 463          moltype = DNA  length = 55
FEATURE                 Location/Qualifiers
source                  1..55
                        mol_type = other DNA
                        organism = synthetic construct
SEQUENCE: 463
gtgactggag ttcagacgtg tgctcttccg atctttctgt tctccttcac tttcc       55

SEQ ID NO: 464          moltype = DNA  length = 54
FEATURE                 Location/Qualifiers
source                  1..54
                        mol_type = other DNA
                        organism = synthetic construct
SEQUENCE: 464
gtgactggag ttcagacgtg tgctcttccg atctccagcc cacgctcttc tcac        54

SEQ ID NO: 465          moltype = DNA  length = 59
FEATURE                 Location/Qualifiers
source                  1..59
                        mol_type = other DNA
                        organism = synthetic construct
SEQUENCE: 465
gtgactggag ttcagacgtg tgctcttccg atctccccaa accccaatga agagagacc   59

SEQ ID NO: 466          moltype = DNA  length = 58
FEATURE                 Location/Qualifiers
source                  1..58
                        mol_type = other DNA
                        organism = synthetic construct
SEQUENCE: 466
gtgactggag ttcagacgtg tgctcttccg atctcagaaa acagatctgt atttattt    58

SEQ ID NO: 467          moltype = DNA  length = 56
FEATURE                 Location/Qualifiers
source                  1..56
                        mol_type = other DNA
                        organism = synthetic construct
```

```
SEQUENCE: 467
gtgactggag ttcagacgtg tgctcttccg atctttgtgg acaggttttg aaagat      56

SEQ ID NO: 468          moltype = DNA  length = 57
FEATURE                 Location/Qualifiers
source                  1..57
                        mol_type = other DNA
                        organism = synthetic construct
SEQUENCE: 468
gtgactggag ttcagacgtg tgctcttccg atctcatgct gtttaattgt gtggaag     57

SEQ ID NO: 469          moltype = DNA  length = 54
FEATURE                 Location/Qualifiers
source                  1..54
                        mol_type = other DNA
                        organism = synthetic construct
SEQUENCE: 469
gtgactggag ttcagacgtg tgctcttccg atctccgcgg aaaggaaggg gagg        54

SEQ ID NO: 470          moltype = DNA  length = 54
FEATURE                 Location/Qualifiers
source                  1..54
                        mol_type = other DNA
                        organism = synthetic construct
SEQUENCE: 470
gtgactggag ttcagacgtg tgctcttccg atctgtggcg gagggactgg ggac        54

SEQ ID NO: 471          moltype = DNA  length = 54
FEATURE                 Location/Qualifiers
source                  1..54
                        mol_type = other DNA
                        organism = synthetic construct
SEQUENCE: 471
gtgactggag ttcagacgtg tgctcttccg atctcccact cctgaccctg tctc        54

SEQ ID NO: 472          moltype = DNA  length = 55
FEATURE                 Location/Qualifiers
source                  1..55
                        mol_type = other DNA
                        organism = synthetic construct
SEQUENCE: 472
gtgactggag ttcagacgtg tgctcttccg atctcccctt tcatgcccct tgtgg       55

SEQ ID NO: 473          moltype = DNA  length = 54
FEATURE                 Location/Qualifiers
source                  1..54
                        mol_type = other DNA
                        organism = synthetic construct
SEQUENCE: 473
gtgactggag ttcagacgtg tgctcttccg atctatggct tgcagctcct ggtg        54

SEQ ID NO: 474          moltype = DNA  length = 57
FEATURE                 Location/Qualifiers
source                  1..57
                        mol_type = other DNA
                        organism = synthetic construct
SEQUENCE: 474
gtgactggag ttcagacgtg tgctcttccg atcttatgta ccatcgatgt ctacatg     57

SEQ ID NO: 475          moltype = DNA  length = 54
FEATURE                 Location/Qualifiers
source                  1..54
                        mol_type = other DNA
                        organism = synthetic construct
SEQUENCE: 475
gtgactggag ttcagacgtg tgctcttccg atctcccgag acccccagcg ctac        54

SEQ ID NO: 476          moltype = DNA  length = 54
FEATURE                 Location/Qualifiers
source                  1..54
                        mol_type = other DNA
                        organism = synthetic construct
SEQUENCE: 476
gtgactggag ttcagacgtg tgctcttccg atctccacag cagggcttct tcag        54

SEQ ID NO: 477          moltype = DNA  length = 56
FEATURE                 Location/Qualifiers
source                  1..56
                        mol_type = other DNA
```

```
                        organism = synthetic construct
SEQUENCE: 477
gtgactggag ttcagacgtg tgctcttccg atctttgaag gagacggact ggtgag      56

SEQ ID NO: 478          moltype = DNA  length = 56
FEATURE                 Location/Qualifiers
source                  1..56
                        mol_type = other DNA
                        organism = synthetic construct
SEQUENCE: 478
gtgactggag ttcagacgtg tgctcttccg atcttcacca cgaaatcctt ggtctc      56

SEQ ID NO: 479          moltype = DNA  length = 55
FEATURE                 Location/Qualifiers
source                  1..55
                        mol_type = other DNA
                        organism = synthetic construct
SEQUENCE: 479
gtgactggag ttcagacgtg tgctcttccg atctgttagt gagccaggta atgag       55

SEQ ID NO: 480          moltype = DNA  length = 57
FEATURE                 Location/Qualifiers
source                  1..57
                        mol_type = other DNA
                        organism = synthetic construct
SEQUENCE: 480
gtgactggag ttcagacgtg tgctcttccg atcttcatca ctcgagtccc gtctacc     57

SEQ ID NO: 481          moltype = DNA  length = 54
FEATURE                 Location/Qualifiers
source                  1..54
                        mol_type = other DNA
                        organism = synthetic construct
SEQUENCE: 481
gtgactggag ttcagacgtg tgctcttccg atcttaggtg ctgtcacatt caac        54

SEQ ID NO: 482          moltype = DNA  length = 58
FEATURE                 Location/Qualifiers
source                  1..58
                        mol_type = other DNA
                        organism = synthetic construct
SEQUENCE: 482
gtgactggag ttcagacgtg tgctcttccg atctggtcag tgggattgta acaaccag    58

SEQ ID NO: 483          moltype = DNA  length = 55
FEATURE                 Location/Qualifiers
source                  1..55
                        mol_type = other DNA
                        organism = synthetic construct
SEQUENCE: 483
gtgactggag ttcagacgtg tgctcttccg atctcactgt cacccttcc ttggc        55

SEQ ID NO: 484          moltype = DNA  length = 56
FEATURE                 Location/Qualifiers
source                  1..56
                        mol_type = other DNA
                        organism = synthetic construct
SEQUENCE: 484
gtgactggag ttcagacgtg tgctcttccg atcttcatgt attggtctct catggc      56

SEQ ID NO: 485          moltype = DNA  length = 60
FEATURE                 Location/Qualifiers
source                  1..60
                        mol_type = other DNA
                        organism = synthetic construct
SEQUENCE: 485
gtgactggag ttcagacgtg tgctcttccg atctaaaaca agtggttata gatggtgaaa  60

SEQ ID NO: 486          moltype = DNA  length = 57
FEATURE                 Location/Qualifiers
source                  1..57
                        mol_type = other DNA
                        organism = synthetic construct
SEQUENCE: 486
gtgactggag ttcagacgtg tgctcttccg atctggttct ggattagctg gattgtc     57

SEQ ID NO: 487          moltype = DNA  length = 58
FEATURE                 Location/Qualifiers
source                  1..58
```

```
                        mol_type = other DNA
                        organism = synthetic construct
SEQUENCE: 487
gtgactggag ttcagacgtg tgctcttccg atcttgtgaa atgactgagt acaaactg    58

SEQ ID NO: 488          moltype = DNA  length = 55
FEATURE                 Location/Qualifiers
source                  1..55
                        mol_type = other DNA
                        organism = synthetic construct
SEQUENCE: 488
gtgactggag ttcagacgtg tgctcttccg atctaggaag agcacagtca ctttg       55

SEQ ID NO: 489          moltype = DNA  length = 54
FEATURE                 Location/Qualifiers
source                  1..54
                        mol_type = other DNA
                        organism = synthetic construct
SEQUENCE: 489
gtgactggag ttcagacgtg tgctcttccg atctagtggc ccgcttctgt ctcc        54

SEQ ID NO: 490          moltype = DNA  length = 60
FEATURE                 Location/Qualifiers
source                  1..60
                        mol_type = other DNA
                        organism = synthetic construct
SEQUENCE: 490
gtgactggag ttcagacgtg tgctcttccg atctcagcat tactctgtgt cccgttaaac  60

SEQ ID NO: 491          moltype = DNA  length = 59
FEATURE                 Location/Qualifiers
source                  1..59
                        mol_type = other DNA
                        organism = synthetic construct
SEQUENCE: 491
gtgactggag ttcagacgtg tgctcttccg atctcaggcc ttcccctctc tttctatag   59

SEQ ID NO: 492          moltype = DNA  length = 55
FEATURE                 Location/Qualifiers
source                  1..55
                        mol_type = other DNA
                        organism = synthetic construct
SEQUENCE: 492
gtgactggag ttcagacgtg tgctcttccg atctactata ccagtccacg gatag       55

SEQ ID NO: 493          moltype = DNA  length = 58
FEATURE                 Location/Qualifiers
source                  1..58
                        mol_type = other DNA
                        organism = synthetic construct
SEQUENCE: 493
gtgactggag ttcagacgtg tgctcttccg atctggctac ttctttgatt tctggaac    58

SEQ ID NO: 494          moltype = DNA  length = 60
FEATURE                 Location/Qualifiers
source                  1..60
                        mol_type = other DNA
                        organism = synthetic construct
SEQUENCE: 494
gtgactggag ttcagacgtg tgctcttccg atctattatg acttgtcaca atgtcaccac  60

SEQ ID NO: 495          moltype = DNA  length = 57
FEATURE                 Location/Qualifiers
source                  1..57
                        mol_type = other DNA
                        organism = synthetic construct
SEQUENCE: 495
gtgactggag ttcagacgtg tgctcttccg atctttttct gtttggcttg acttgac     57

SEQ ID NO: 496          moltype = DNA  length = 59
FEATURE                 Location/Qualifiers
source                  1..59
                        mol_type = other DNA
                        organism = synthetic construct
SEQUENCE: 496
gtgactggag ttcagacgtg tgctcttccg atctacccct ccttcctaga gagttagag   59

SEQ ID NO: 497          moltype = DNA  length = 57
FEATURE                 Location/Qualifiers
```

```
source                  1..57
                        mol_type = other DNA
                        organism = synthetic construct
SEQUENCE: 497
gtgactggag ttcagacgtg tgctcttccg atctccccaa gagagcaaca cccacac     57

SEQ ID NO: 498          moltype = DNA  length = 56
FEATURE                 Location/Qualifiers
source                  1..56
                        mol_type = other DNA
                        organism = synthetic construct
SEQUENCE: 498
gtgactggag ttcagacgtg tgctcttccg atctccctgc tgactcctct cctgac      56

SEQ ID NO: 499          moltype = DNA  length = 54
FEATURE                 Location/Qualifiers
source                  1..54
                        mol_type = other DNA
                        organism = synthetic construct
SEQUENCE: 499
gtgactggag ttcagacgtg tgctcttccg atctacagga tgcagagaca gagc        54

SEQ ID NO: 500          moltype = DNA  length = 60
FEATURE                 Location/Qualifiers
source                  1..60
                        mol_type = other DNA
                        organism = synthetic construct
SEQUENCE: 500
gtgactggag ttcagacgtg tgctcttccg atctggtgga aagaacctct caacattgtc  60

SEQ ID NO: 501          moltype = DNA  length = 55
FEATURE                 Location/Qualifiers
source                  1..55
                        mol_type = other DNA
                        organism = synthetic construct
SEQUENCE: 501
gtgactggag ttcagacgtg tgctcttccg atcttagaac cattgctcaa aggac       55

SEQ ID NO: 502          moltype = DNA  length = 55
FEATURE                 Location/Qualifiers
source                  1..55
                        mol_type = other DNA
                        organism = synthetic construct
SEQUENCE: 502
gtgactggag ttcagacgtg tgctcttccg atctgccgaa gtctgaccct ttttg       55

SEQ ID NO: 503          moltype = DNA  length = 55
FEATURE                 Location/Qualifiers
source                  1..55
                        mol_type = other DNA
                        organism = synthetic construct
SEQUENCE: 503
gtgactggag ttcagacgtg tgctcttccg atcttggtcc accgccagtc tcctg       55

SEQ ID NO: 504          moltype = DNA  length = 56
FEATURE                 Location/Qualifiers
source                  1..56
                        mol_type = other DNA
                        organism = synthetic construct
SEQUENCE: 504
gtgactggag ttcagacgtg tgctcttccg atcttggtag ttgcatatgg tgattt      56

SEQ ID NO: 505          moltype = DNA  length = 54
FEATURE                 Location/Qualifiers
source                  1..54
                        mol_type = other DNA
                        organism = synthetic construct
SEQUENCE: 505
gtgactggag ttcagacgtg tgctcttccg atctggtgcc atttggtgat ttcc        54

SEQ ID NO: 506          moltype = DNA  length = 57
FEATURE                 Location/Qualifiers
source                  1..57
                        mol_type = other DNA
                        organism = synthetic construct
SEQUENCE: 506
gtgactggag ttcagacgtg tgctcttccg atctatgaga agagggttga ggagttc     57

SEQ ID NO: 507          moltype = DNA  length = 58
```

```
FEATURE                Location/Qualifiers
source                 1..58
                       mol_type = other DNA
                       organism = synthetic construct
SEQUENCE: 507
gtgactggag ttcagacgtg tgctcttccg atcttgcagt tgtaggttat aactatcc    58

SEQ ID NO: 508         moltype = DNA  length = 58
FEATURE                Location/Qualifiers
source                 1..58
                       mol_type = other DNA
                       organism = synthetic construct
SEQUENCE: 508
gtgactggag ttcagacgtg tgctcttccg atctttcaat gggtcatatc acagattc    58

SEQ ID NO: 509         moltype = DNA  length = 54
FEATURE                Location/Qualifiers
source                 1..54
                       mol_type = other DNA
                       organism = synthetic construct
SEQUENCE: 509
gtgactggag ttcagacgtg tgctcttccg atctggcagc aacagtctta cctg        54

SEQ ID NO: 510         moltype = DNA  length = 54
FEATURE                Location/Qualifiers
source                 1..54
                       mol_type = other DNA
                       organism = synthetic construct
SEQUENCE: 510
gtgactggag ttcagacgtg tgctcttccg atctggattg cctttaccac tcag        54

SEQ ID NO: 511         moltype = DNA  length = 58
FEATURE                Location/Qualifiers
source                 1..58
                       mol_type = other DNA
                       organism = synthetic construct
SEQUENCE: 511
gtgactggag ttcagacgtg tgctcttccg atctctgcat tctgactttc agtaaggc    58

SEQ ID NO: 512         moltype = DNA  length = 60
FEATURE                Location/Qualifiers
source                 1..60
                       mol_type = other DNA
                       organism = synthetic construct
SEQUENCE: 512
gtgactggag ttcagacgtg tgctcttccg atctacatgc tccataaata ttctaacatg  60

SEQ ID NO: 513         moltype = DNA  length = 60
FEATURE                Location/Qualifiers
source                 1..60
                       mol_type = other DNA
                       organism = synthetic construct
SEQUENCE: 513
gtgactggag ttcagacgtg tgctcttccg atctacttct tgtgcattgc aggtaatatc  60

SEQ ID NO: 514         moltype = DNA  length = 54
FEATURE                Location/Qualifiers
source                 1..54
                       mol_type = other DNA
                       organism = synthetic construct
SEQUENCE: 514
gtgactggag ttcagacgtg tgctcttccg atctcctgag cgtcatctgc cccc        54

SEQ ID NO: 515         moltype = DNA  length = 55
FEATURE                Location/Qualifiers
source                 1..55
                       mol_type = other DNA
                       organism = synthetic construct
SEQUENCE: 515
gtgactggag ttcagacgtg tgctcttccg atctacccaa atcctcacgc aaccc       55

SEQ ID NO: 516         moltype = DNA  length = 54
FEATURE                Location/Qualifiers
source                 1..54
                       mol_type = other DNA
                       organism = synthetic construct
SEQUENCE: 516
gtgactggag ttcagacgtg tgctcttccg atctcagggg catccatggg agcc        54
```

```
SEQ ID NO: 517          moltype = DNA  length = 60
FEATURE                 Location/Qualifiers
source                  1..60
                        mol_type = other DNA
                        organism = synthetic construct
SEQUENCE: 517
gtgactggag ttcagacgtg tgctcttccg atctgctcag aacctggtat ctactttctg  60

SEQ ID NO: 518          moltype = DNA  length = 56
FEATURE                 Location/Qualifiers
source                  1..56
                        mol_type = other DNA
                        organism = synthetic construct
SEQUENCE: 518
gtgactggag ttcagacgtg tgctcttccg atctcgggga gaggtggaga ggcttc      56

SEQ ID NO: 519          moltype = DNA  length = 54
FEATURE                 Location/Qualifiers
source                  1..54
                        mol_type = other DNA
                        organism = synthetic construct
SEQUENCE: 519
gtgactggag ttcagacgtg tgctcttccg atctactggc atgacccca cccc        54

SEQ ID NO: 520          moltype = DNA  length = 55
FEATURE                 Location/Qualifiers
source                  1..55
                        mol_type = other DNA
                        organism = synthetic construct
SEQUENCE: 520
gtgactggag ttcagacgtg tgctcttccg atctgaccgt gtccttaccg tgacg       55

SEQ ID NO: 521          moltype = DNA  length = 55
FEATURE                 Location/Qualifiers
source                  1..55
                        mol_type = other DNA
                        organism = synthetic construct
SEQUENCE: 521
gtgactggag ttcagacgtg tgctcttccg atcttcatcg accaagtcca gaatg       55

SEQ ID NO: 522          moltype = DNA  length = 60
FEATURE                 Location/Qualifiers
source                  1..60
                        mol_type = other DNA
                        organism = synthetic construct
SEQUENCE: 522
gtgactggag ttcagacgtg tgctcttccg atctagacat tgttggccaa aatagtccag  60

SEQ ID NO: 523          moltype = DNA  length = 56
FEATURE                 Location/Qualifiers
source                  1..56
                        mol_type = other DNA
                        organism = synthetic construct
SEQUENCE: 523
gtgactggag ttcagacgtg tgctcttccg atctgcagca gccaccgtga gttcag      56

SEQ ID NO: 524          moltype = DNA  length = 55
FEATURE                 Location/Qualifiers
source                  1..55
                        mol_type = other DNA
                        organism = synthetic construct
SEQUENCE: 524
gtgactggag ttcagacgtg tgctcttccg atctaccctc cagcgaattt catac       55

SEQ ID NO: 525          moltype = DNA  length = 57
FEATURE                 Location/Qualifiers
source                  1..57
                        mol_type = other DNA
                        organism = synthetic construct
SEQUENCE: 525
gtgactggag ttcagacgtg tgctcttccg atctggctgt tccttcaacc accttcc     57

SEQ ID NO: 526          moltype = DNA  length = 56
FEATURE                 Location/Qualifiers
source                  1..56
                        mol_type = other DNA
                        organism = synthetic construct
SEQUENCE: 526
gtgactggag ttcagacgtg tgctcttccg atctagagct tgtttttcac tggatc      56
```

```
SEQ ID NO: 527          moltype = DNA  length = 59
FEATURE                 Location/Qualifiers
source                  1..59
                        mol_type = other DNA
                        organism = synthetic construct
SEQUENCE: 527
gtgactggag ttcagacgtg tgctcttccg atctgatcct gagtcatttc ttccttttc   59

SEQ ID NO: 528          moltype = DNA  length = 54
FEATURE                 Location/Qualifiers
source                  1..54
                        mol_type = other DNA
                        organism = synthetic construct
SEQUENCE: 528
gtgactggag ttcagacgtg tgctcttccg atctagcctg accagtgagg gaag        54

SEQ ID NO: 529          moltype = DNA  length = 59
FEATURE                 Location/Qualifiers
source                  1..59
                        mol_type = other DNA
                        organism = synthetic construct
SEQUENCE: 529
gtgactggag ttcagacgtg tgctcttccg atcttgacat atggccattt ctgttttcc   59

SEQ ID NO: 530          moltype = DNA  length = 54
FEATURE                 Location/Qualifiers
source                  1..54
                        mol_type = other DNA
                        organism = synthetic construct
SEQUENCE: 530
gtgactggag ttcagacgtg tgctcttccg atctattgca gtccttcccc tctg        54

SEQ ID NO: 531          moltype = DNA  length = 60
FEATURE                 Location/Qualifiers
source                  1..60
                        mol_type = other DNA
                        organism = synthetic construct
SEQUENCE: 531
gtgactggag ttcagacgtg tgctcttccg atctctctcc agagtgctct aatgactgag  60

SEQ ID NO: 532          moltype = DNA  length = 54
FEATURE                 Location/Qualifiers
source                  1..54
                        mol_type = other DNA
                        organism = synthetic construct
SEQUENCE: 532
gtgactggag ttcagacgtg tgctcttccg atctggaaag cccctgtttc atac        54

SEQ ID NO: 533          moltype = DNA  length = 58
FEATURE                 Location/Qualifiers
source                  1..58
                        mol_type = other DNA
                        organism = synthetic construct
SEQUENCE: 533
gtgactggag ttcagacgtg tgctcttccg atctgcatgc gcttgacatc agtttgcc    58

SEQ ID NO: 534          moltype = DNA  length = 56
FEATURE                 Location/Qualifiers
source                  1..56
                        mol_type = other DNA
                        organism = synthetic construct
SEQUENCE: 534
gtgactggag ttcagacgtg tgctcttccg atctaataaa aggcagcttg gacacg      56

SEQ ID NO: 535          moltype = DNA  length = 57
FEATURE                 Location/Qualifiers
source                  1..57
                        mol_type = other DNA
                        organism = synthetic construct
SEQUENCE: 535
gtgactggag ttcagacgtg tgctcttccg atctaatggt tttcttttct cctccaa     57

SEQ ID NO: 536          moltype = DNA  length = 60
FEATURE                 Location/Qualifiers
source                  1..60
                        mol_type = other DNA
                        organism = synthetic construct
SEQUENCE: 536
```

```
gtgactggag ttcagacgtg tgctcttccg atctcctttg caggactgtc aagcagagaa  60

SEQ ID NO: 537          moltype = DNA  length = 55
FEATURE                 Location/Qualifiers
source                  1..55
                        mol_type = other DNA
                        organism = synthetic construct
SEQUENCE: 537
gtgactggag ttcagacgtg tgctcttccg atctaggaga gcatttaagg gagag       55

SEQ ID NO: 538          moltype = DNA  length = 60
FEATURE                 Location/Qualifiers
source                  1..60
                        mol_type = other DNA
                        organism = synthetic construct
SEQUENCE: 538
gtgactggag ttcagacgtg tgctcttccg atctaaaatc atatgctcca ctaacaaccc  60

SEQ ID NO: 539          moltype = DNA  length = 54
FEATURE                 Location/Qualifiers
source                  1..54
                        mol_type = other DNA
                        organism = synthetic construct
SEQUENCE: 539
gtgactggag ttcagacgtg tgctcttccg atcttgggtc atgttgcagc agtc        54

SEQ ID NO: 540          moltype = DNA  length = 59
FEATURE                 Location/Qualifiers
source                  1..59
                        mol_type = other DNA
                        organism = synthetic construct
SEQUENCE: 540
gtgactggag ttcagacgtg tgctcttccg atctaagtcc caaccatgac aagattttc   59

SEQ ID NO: 541          moltype = DNA  length = 60
FEATURE                 Location/Qualifiers
source                  1..60
                        mol_type = other DNA
                        organism = synthetic construct
SEQUENCE: 541
gtgactggag ttcagacgtg tgctcttccg atctacccaa aagtaatcat cttaagtgtt  60

SEQ ID NO: 542          moltype = DNA  length = 60
FEATURE                 Location/Qualifiers
source                  1..60
                        mol_type = other DNA
                        organism = synthetic construct
SEQUENCE: 542
gtgactggag ttcagacgtg tgctcttccg atctaggaag cttagatagt tctcgttctg  60

SEQ ID NO: 543          moltype = DNA  length = 55
FEATURE                 Location/Qualifiers
source                  1..55
                        mol_type = other DNA
                        organism = synthetic construct
SEQUENCE: 543
gtgactggag ttcagacgtg tgctcttccg atctcaggtc acggggagcc aatgg       55

SEQ ID NO: 544          moltype = DNA  length = 57
FEATURE                 Location/Qualifiers
source                  1..57
                        mol_type = other DNA
                        organism = synthetic construct
SEQUENCE: 544
gtgactggag ttcagacgtg tgctcttccg atctcatcag ctgaagatga aatagga     57

SEQ ID NO: 545          moltype = DNA  length = 57
FEATURE                 Location/Qualifiers
source                  1..57
                        mol_type = other DNA
                        organism = synthetic construct
SEQUENCE: 545
gtgactggag ttcagacgtg tgctcttccg atctccctcc aaaagtggtg ctcagac     57

SEQ ID NO: 546          moltype = DNA  length = 56
FEATURE                 Location/Qualifiers
source                  1..56
                        mol_type = other DNA
                        organism = synthetic construct
```

```
SEQUENCE: 546
gtgactggag ttcagacgtg tgctcttccg atcttggaca aaccatgcca ccaagc      56

SEQ ID NO: 547         moltype = DNA  length = 59
FEATURE                Location/Qualifiers
source                 1..59
                       mol_type = other DNA
                       organism = synthetic construct
SEQUENCE: 547
gtgactggag ttcagacgtg tgctcttccg atctggtgcc ctactacctg gagaacgag   59

SEQ ID NO: 548         moltype = DNA  length = 55
FEATURE                Location/Qualifiers
source                 1..55
                       mol_type = other DNA
                       organism = synthetic construct
SEQUENCE: 548
gtgactggag ttcagacgtg tgctcttccg atctctgcaa ggccttcttc aagag       55

SEQ ID NO: 549         moltype = DNA  length = 57
FEATURE                Location/Qualifiers
source                 1..57
                       mol_type = other DNA
                       organism = synthetic construct
SEQUENCE: 549
gtgactggag ttcagacgtg tgctcttccg atctagctgc caggcctgcc ggctccg     57

SEQ ID NO: 550         moltype = DNA  length = 58
FEATURE                Location/Qualifiers
source                 1..58
                       mol_type = other DNA
                       organism = synthetic construct
SEQUENCE: 550
gtgactggag ttcagacgtg tgctcttccg atctgtataa aagtttacac gggaaaaa    58

SEQ ID NO: 551         moltype = DNA  length = 55
FEATURE                Location/Qualifiers
source                 1..55
                       mol_type = other DNA
                       organism = synthetic construct
SEQUENCE: 551
gtgactggag ttcagacgtg tgctcttccg atctctgctg gagacatgag agctg       55

SEQ ID NO: 552         moltype = DNA  length = 54
FEATURE                Location/Qualifiers
source                 1..54
                       mol_type = other DNA
                       organism = synthetic construct
SEQUENCE: 552
gtgactggag ttcagacgtg tgctcttccg atcttttgat catgagcggg cttg        54

SEQ ID NO: 553         moltype = DNA  length = 54
FEATURE                Location/Qualifiers
source                 1..54
                       mol_type = other DNA
                       organism = synthetic construct
SEQUENCE: 553
gtgactggag ttcagacgtg tgctcttccg atcttgcctt gttggatgct gagc        54

SEQ ID NO: 554         moltype = DNA  length = 60
FEATURE                Location/Qualifiers
source                 1..60
                       mol_type = other DNA
                       organism = synthetic construct
SEQUENCE: 554
gtgactggag ttcagacgtg tgctcttccg atctcactga agggtctggt aggatcatac  60

SEQ ID NO: 555         moltype = DNA  length = 54
FEATURE                Location/Qualifiers
source                 1..54
                       mol_type = other DNA
                       organism = synthetic construct
SEQUENCE: 555
gtgactggag ttcagacgtg tgctcttccg atctatgatc aactgggcga agag        54

SEQ ID NO: 556         moltype = DNA  length = 60
FEATURE                Location/Qualifiers
source                 1..60
                       mol_type = other DNA
```

```
                        organism = synthetic construct
SEQUENCE: 556
gtgactggag ttcagacgtg tgctcttccg atctacaagt tcttgaaaag ctattgactc  60

SEQ ID NO: 557          moltype = DNA  length = 54
FEATURE                 Location/Qualifiers
source                  1..54
                        mol_type = other DNA
                        organism = synthetic construct
SEQUENCE: 557
gtgactggag ttcagacgtg tgctcttccg atctggttgg ctctaaagta gtcc        54

SEQ ID NO: 558          moltype = DNA  length = 54
FEATURE                 Location/Qualifiers
source                  1..54
                        mol_type = other DNA
                        organism = synthetic construct
SEQUENCE: 558
gtgactggag ttcagacgtg tgctcttccg atctggatta tctgaaccgt gtgg        54

SEQ ID NO: 559          moltype = DNA  length = 60
FEATURE                 Location/Qualifiers
source                  1..60
                        mol_type = other DNA
                        organism = synthetic construct
SEQUENCE: 559
gtgactggag ttcagacgtg tgctcttccg atctgtatat acaatgccac ctgaatacag  60

SEQ ID NO: 560          moltype = DNA  length = 54
FEATURE                 Location/Qualifiers
source                  1..54
                        mol_type = other DNA
                        organism = synthetic construct
SEQUENCE: 560
gtgactggag ttcagacgtg tgctcttccg atcttgtccc cagtccattt tcac        54

SEQ ID NO: 561          moltype = DNA  length = 55
FEATURE                 Location/Qualifiers
source                  1..55
                        mol_type = other DNA
                        organism = synthetic construct
SEQUENCE: 561
gtgactggag ttcagacgtg tgctcttccg atctgaccgc atcgtggcct tgacc       55

SEQ ID NO: 562          moltype = DNA  length = 54
FEATURE                 Location/Qualifiers
source                  1..54
                        mol_type = other DNA
                        organism = synthetic construct
SEQUENCE: 562
gtgactggag ttcagacgtg tgctcttccg atcttcagat gaaaccacca gcac        54

SEQ ID NO: 563          moltype = DNA  length = 54
FEATURE                 Location/Qualifiers
source                  1..54
                        mol_type = other DNA
                        organism = synthetic construct
SEQUENCE: 563
gtgactggag ttcagacgtg tgctcttccg atctccgcct cccgctctcc cttc        54

SEQ ID NO: 564          moltype = DNA  length = 55
FEATURE                 Location/Qualifiers
source                  1..55
                        mol_type = other DNA
                        organism = synthetic construct
SEQUENCE: 564
gtgactggag ttcagacgtg tgctcttccg atctcccagg ggagccttca ggttc       55

SEQ ID NO: 565          moltype = DNA  length = 55
FEATURE                 Location/Qualifiers
source                  1..55
                        mol_type = other DNA
                        organism = synthetic construct
SEQUENCE: 565
gtgactggag ttcagacgtg tgctcttccg atctgaagcc aaacctgctc acctg       55

SEQ ID NO: 566          moltype = DNA  length = 55
FEATURE                 Location/Qualifiers
source                  1..55
```

```
                        mol_type = other DNA
                        organism = synthetic construct
SEQUENCE: 566
gtgactggag ttcagacgtg tgctcttccg atctgatacc ccagctcaga tcttc      55

SEQ ID NO: 567          moltype = DNA  length = 57
FEATURE                 Location/Qualifiers
source                  1..57
                        mol_type = other DNA
                        organism = synthetic construct
SEQUENCE: 567
gtgactggag ttcagacgtg tgctcttccg atctagtaaa tgagtctcaa cgtgttc    57

SEQ ID NO: 568          moltype = DNA  length = 55
FEATURE                 Location/Qualifiers
source                  1..55
                        mol_type = other DNA
                        organism = synthetic construct
SEQUENCE: 568
gtgactggag ttcagacgtg tgctcttccg atctgttcat ggatgcactg gagtc      55

SEQ ID NO: 569          moltype = DNA  length = 58
FEATURE                 Location/Qualifiers
source                  1..58
                        mol_type = other DNA
                        organism = synthetic construct
SEQUENCE: 569
gtgactggag ttcagacgtg tgctcttccg atctggtaca ggggcgaggt catcactg   58

SEQ ID NO: 570          moltype = DNA  length = 60
FEATURE                 Location/Qualifiers
source                  1..60
                        mol_type = other DNA
                        organism = synthetic construct
SEQUENCE: 570
gtgactggag ttcagacgtg tgctcttccg atcttccatc tctttgtcgg tggtattaac  60

SEQ ID NO: 571          moltype = DNA  length = 60
FEATURE                 Location/Qualifiers
source                  1..60
                        mol_type = other DNA
                        organism = synthetic construct
SEQUENCE: 571
gtgactggag ttcagacgtg tgctcttccg atctccacag tgagctcgat cctccttttc  60

SEQ ID NO: 572          moltype = DNA  length = 59
FEATURE                 Location/Qualifiers
source                  1..59
                        mol_type = other DNA
                        organism = synthetic construct
SEQUENCE: 572
gtgactggag ttcagacgtg tgctcttccg atctatggac aacagtcaaa caacaattc   59

SEQ ID NO: 573          moltype = DNA  length = 58
FEATURE                 Location/Qualifiers
source                  1..58
                        mol_type = other DNA
                        organism = synthetic construct
SEQUENCE: 573
gtgactggag ttcagacgtg tgctcttccg atctgcatta gaaagcctgt agttttac   58

SEQ ID NO: 574          moltype = DNA  length = 60
FEATURE                 Location/Qualifiers
source                  1..60
                        mol_type = other DNA
                        organism = synthetic construct
SEQUENCE: 574
gtgactggag ttcagacgtg tgctcttccg atcttacggt agtgggggaa ggcatatatc  60

SEQ ID NO: 575          moltype = DNA  length = 56
FEATURE                 Location/Qualifiers
source                  1..56
                        mol_type = other DNA
                        organism = synthetic construct
SEQUENCE: 575
gtgactggag ttcagacgtg tgctcttccg atctcaggtt tctaacgcct gttttc     56

SEQ ID NO: 576          moltype = DNA  length = 57
FEATURE                 Location/Qualifiers
```

```
source                  1..57
                        mol_type = other DNA
                        organism = synthetic construct
SEQUENCE: 576
gtgactggag ttcagacgtg tgctcttccg atctagggta caaattctca gatcatc     57

SEQ ID NO: 577          moltype = DNA  length = 56
FEATURE                 Location/Qualifiers
source                  1..56
                        mol_type = other DNA
                        organism = synthetic construct
SEQUENCE: 577
gtgactggag ttcagacgtg tgctcttccg atctcgcgat ggcccagctc ctcagc      56

SEQ ID NO: 578          moltype = DNA  length = 54
FEATURE                 Location/Qualifiers
source                  1..54
                        mol_type = other DNA
                        organism = synthetic construct
SEQUENCE: 578
gtgactggag ttcagacgtg tgctcttccg atctgggctt cctggacacg ctgg        54

SEQ ID NO: 579          moltype = DNA  length = 59
FEATURE                 Location/Qualifiers
source                  1..59
                        mol_type = other DNA
                        organism = synthetic construct
SEQUENCE: 579
gtgactggag ttcagacgtg tgctcttccg atctctacac aagcttcctt tccgtcatg   59

SEQ ID NO: 580          moltype = DNA  length = 54
FEATURE                 Location/Qualifiers
source                  1..54
                        mol_type = other DNA
                        organism = synthetic construct
SEQUENCE: 580
gtgactggag ttcagacgtg tgctcttccg atctaacttc gtcctccaga gtcg        54

SEQ ID NO: 581          moltype = RNA  length = 54
FEATURE                 Location/Qualifiers
source                  1..54
                        mol_type = other RNA
                        organism = synthetic construct
SEQUENCE: 581
gtgactggag ttcagacgtg tgctcttccg atctcggaga gggggagagc aggc        54

SEQ ID NO: 582          moltype = DNA  length = 58
FEATURE                 Location/Qualifiers
source                  1..58
                        mol_type = other DNA
                        organism = synthetic construct
SEQUENCE: 582
gtgactggag ttcagacgtg tgctcttccg atctatccat tgcctgtcta aagaacac    58

SEQ ID NO: 583          moltype = DNA  length = 60
FEATURE                 Location/Qualifiers
source                  1..60
                        mol_type = other DNA
                        organism = synthetic construct
SEQUENCE: 583
gtgactggag ttcagacgtg tgctcttccg atcttgttat taatatgagt attgttaacc  60

SEQ ID NO: 584          moltype = DNA  length = 54
FEATURE                 Location/Qualifiers
source                  1..54
                        mol_type = other DNA
                        organism = synthetic construct
SEQUENCE: 584
gtgactggag ttcagacgtg tgctcttccg atcttgaagg ctgttccctg tttc        54

SEQ ID NO: 585          moltype = DNA  length = 58
FEATURE                 Location/Qualifiers
source                  1..58
                        mol_type = other DNA
                        organism = synthetic construct
SEQUENCE: 585
gtgactggag ttcagacgtg tgctcttccg atctgcgcaa caagcccact gtctatgg    58

SEQ ID NO: 586          moltype = DNA  length = 55
```

```
FEATURE                Location/Qualifiers
source                 1..55
                       mol_type = other DNA
                       organism = synthetic construct
SEQUENCE: 586
gtgactggag ttcagacgtg tgctcttccg atctatctcc cacttgtcgt agttg      55

SEQ ID NO: 587         moltype = DNA  length = 54
FEATURE                Location/Qualifiers
source                 1..54
                       mol_type = other DNA
                       organism = synthetic construct
SEQUENCE: 587
gtgactggag ttcagacgtg tgctcttccg atctagacgc cttgccccac gtac       54

SEQ ID NO: 588         moltype = DNA  length = 60
FEATURE                Location/Qualifiers
source                 1..60
                       mol_type = other DNA
                       organism = synthetic construct
SEQUENCE: 588
gtgactggag ttcagacgtg tgctcttccg atctaaagca cttcctgaaa taatttcacc  60

SEQ ID NO: 589         moltype = DNA  length = 54
FEATURE                Location/Qualifiers
source                 1..54
                       mol_type = other DNA
                       organism = synthetic construct
SEQUENCE: 589
gtgactggag ttcagacgtg tgctcttccg atctcgagac cctctcttca gagc       54

SEQ ID NO: 590         moltype = DNA  length = 59
FEATURE                Location/Qualifiers
source                 1..59
                       mol_type = other DNA
                       organism = synthetic construct
SEQUENCE: 590
gtgactggag ttcagacgtg tgctcttccg atcttgttga agtcctcgtt gtcttgttg   59

SEQ ID NO: 591         moltype = DNA  length = 55
FEATURE                Location/Qualifiers
source                 1..55
                       mol_type = other DNA
                       organism = synthetic construct
SEQUENCE: 591
gtgactggag ttcagacgtg tgctcttccg atctggctgg ggctttttgt aaaag      55

SEQ ID NO: 592         moltype = DNA  length = 60
FEATURE                Location/Qualifiers
source                 1..60
                       mol_type = other DNA
                       organism = synthetic construct
SEQUENCE: 592
gtgactggag ttcagacgtg tgctcttccg atctatgcaa catttctaaa gttacctact  60

SEQ ID NO: 593         moltype = DNA  length = 55
FEATURE                Location/Qualifiers
source                 1..55
                       mol_type = other DNA
                       organism = synthetic construct
SEQUENCE: 593
gtgactggag ttcagacgtg tgctcttccg atctacaatc atgttgcagc aattc      55

SEQ ID NO: 594         moltype = DNA  length = 60
FEATURE                Location/Qualifiers
source                 1..60
                       mol_type = other DNA
                       organism = synthetic construct
SEQUENCE: 594
gtgactggag ttcagacgtg tgctcttccg atcttatcat tacaccagtt cgtccctttc  60

SEQ ID NO: 595         moltype = DNA  length = 54
FEATURE                Location/Qualifiers
source                 1..54
                       mol_type = other DNA
                       organism = synthetic construct
SEQUENCE: 595
gtgactggag ttcagacgtg tgctcttccg atcttcagat ccaggaagag gaaa       54
```

```
SEQ ID NO: 596          moltype = DNA  length = 54
FEATURE                 Location/Qualifiers
source                  1..54
                        mol_type = other DNA
                        organism = synthetic construct
SEQUENCE: 596
gtgactggag ttcagacgtg tgctcttccg atctctacga cccagttacc atag        54

SEQ ID NO: 597          moltype = DNA  length = 58
FEATURE                 Location/Qualifiers
source                  1..58
                        mol_type = other DNA
                        organism = synthetic construct
SEQUENCE: 597
gtgactggag ttcagacgtg tgctcttccg atctacatgg aaggatgaga atttcaag    58

SEQ ID NO: 598          moltype = DNA  length = 60
FEATURE                 Location/Qualifiers
source                  1..60
                        mol_type = other DNA
                        organism = synthetic construct
SEQUENCE: 598
gtgactggag ttcagacgtg tgctcttccg atctttcctg tgaaataata ctggtatgta  60

SEQ ID NO: 599          moltype = DNA  length = 60
FEATURE                 Location/Qualifiers
source                  1..60
                        mol_type = other DNA
                        organism = synthetic construct
SEQUENCE: 599
gtgactggag ttcagacgtg tgctcttccg atcttcttca taccaggacc agaggaaacc  60

SEQ ID NO: 600          moltype = DNA  length = 60
FEATURE                 Location/Qualifiers
source                  1..60
                        mol_type = other DNA
                        organism = synthetic construct
SEQUENCE: 600
gtgactggag ttcagacgtg tgctcttccg atcttttgtc tttatttgct ttgtcaagat  60

SEQ ID NO: 601          moltype = DNA  length = 60
FEATURE                 Location/Qualifiers
source                  1..60
                        mol_type = other DNA
                        organism = synthetic construct
SEQUENCE: 601
gtgactggag ttcagacgtg tgctcttccg atcttcagct gtactcctag aattaaacac  60

SEQ ID NO: 602          moltype = DNA  length = 60
FEATURE                 Location/Qualifiers
source                  1..60
                        mol_type = other DNA
                        organism = synthetic construct
SEQUENCE: 602
gtgactggag ttcagacgtg tgctcttccg atctgttggt agaagacttg gatcgaattc  60

SEQ ID NO: 603          moltype = DNA  length = 55
FEATURE                 Location/Qualifiers
source                  1..55
                        mol_type = other DNA
                        organism = synthetic construct
SEQUENCE: 603
gtgactggag ttcagacgtg tgctcttccg atctttgggc gaatgcagtt tttcc       55

SEQ ID NO: 604          moltype = DNA  length = 60
FEATURE                 Location/Qualifiers
source                  1..60
                        mol_type = other DNA
                        organism = synthetic construct
SEQUENCE: 604
gtgactggag ttcagacgtg tgctcttccg atctctgatt tgtgaatatg cctactgttc  60

SEQ ID NO: 605          moltype = DNA  length = 54
FEATURE                 Location/Qualifiers
source                  1..54
                        mol_type = other DNA
                        organism = synthetic construct
SEQUENCE: 605
gtgactggag ttcagacgtg tgctcttccg atcttggagt tcatggagga gctg        54
```

```
SEQ ID NO: 606          moltype = DNA  length = 60
FEATURE                 Location/Qualifiers
source                  1..60
                        mol_type = other DNA
                        organism = synthetic construct
SEQUENCE: 606
gtgactggag ttcagacgtg tgctcttccg atctaggtag tctggggaag ctgtaatctc  60

SEQ ID NO: 607          moltype = DNA  length = 55
FEATURE                 Location/Qualifiers
source                  1..55
                        mol_type = other DNA
                        organism = synthetic construct
SEQUENCE: 607
gtgactggag ttcagacgtg tgctcttccg atctctcttt gtccgtggtg ttaac       55

SEQ ID NO: 608          moltype = DNA  length = 58
FEATURE                 Location/Qualifiers
source                  1..58
                        mol_type = other DNA
                        organism = synthetic construct
SEQUENCE: 608
gtgactggag ttcagacgtg tgctcttccg atctgtggcc aaacccatga aggagacc    58

SEQ ID NO: 609          moltype = DNA  length = 58
FEATURE                 Location/Qualifiers
source                  1..58
                        mol_type = other DNA
                        organism = synthetic construct
SEQUENCE: 609
gtgactggag ttcagacgtg tgctcttccg atctgtcact gacagccctc tggacaac    58

SEQ ID NO: 610          moltype = DNA  length = 57
FEATURE                 Location/Qualifiers
source                  1..57
                        mol_type = other DNA
                        organism = synthetic construct
SEQUENCE: 610
gtgactggag ttcagacgtg tgctcttccg atctggacta cgcgcaatgc cttcagc     57

SEQ ID NO: 611          moltype = DNA  length = 54
FEATURE                 Location/Qualifiers
source                  1..54
                        mol_type = other DNA
                        organism = synthetic construct
SEQUENCE: 611
gtgactggag ttcagacgtg tgctcttccg atctctcccg ggccagcctc acgg        54

SEQ ID NO: 612          moltype = DNA  length = 55
FEATURE                 Location/Qualifiers
source                  1..55
                        mol_type = other DNA
                        organism = synthetic construct
SEQUENCE: 612
gtgactggag ttcagacgtg tgctcttccg atctacggaa ggtcctgagg gggtc       55

SEQ ID NO: 613          moltype = DNA  length = 54
FEATURE                 Location/Qualifiers
source                  1..54
                        mol_type = other DNA
                        organism = synthetic construct
SEQUENCE: 613
gtgactggag ttcagacgtg tgctcttccg atctcagctg ctggcacctg gacg        54

SEQ ID NO: 614          moltype = DNA  length = 57
FEATURE                 Location/Qualifiers
source                  1..57
                        mol_type = other DNA
                        organism = synthetic construct
SEQUENCE: 614
gtgactggag ttcagacgtg tgctcttccg atctaggaga ccctgtagga ggacccc     57

SEQ ID NO: 615          moltype = DNA  length = 60
FEATURE                 Location/Qualifiers
source                  1..60
                        mol_type = other DNA
                        organism = synthetic construct
SEQUENCE: 615
```

```
gtgactggag ttcagacgtg tgctcttccg atctctcatt aaaagaggtg ttcttgtgac  60

SEQ ID NO: 616         moltype = DNA  length = 59
FEATURE                Location/Qualifiers
source                 1..59
                       mol_type = other DNA
                       organism = synthetic construct
SEQUENCE: 616
gtgactggag ttcagacgtg tgctcttccg atctaaaatc acatggcatc tgtacagtg   59

SEQ ID NO: 617         moltype = DNA  length = 54
FEATURE                Location/Qualifiers
source                 1..54
                       mol_type = other DNA
                       organism = synthetic construct
SEQUENCE: 617
gtgactggag ttcagacgtg tgctcttccg atcttgagac atgtctgaga ctcc        54

SEQ ID NO: 618         moltype = DNA  length = 59
FEATURE                Location/Qualifiers
source                 1..59
                       mol_type = other DNA
                       organism = synthetic construct
SEQUENCE: 618
gtgactggag ttcagacgtg tgctcttccg atctactggg ctctctggag gtgtatatg   59

SEQ ID NO: 619         moltype = DNA  length = 55
FEATURE                Location/Qualifiers
source                 1..55
                       mol_type = other DNA
                       organism = synthetic construct
SEQUENCE: 619
gtgactggag ttcagacgtg tgctcttccg atctcgccac ttcatgttcc agtgc       55

SEQ ID NO: 620         moltype = DNA  length = 57
FEATURE                Location/Qualifiers
source                 1..57
                       mol_type = other DNA
                       organism = synthetic construct
SEQUENCE: 620
gtgactggag ttcagacgtg tgctcttccg atctactggg ctacgtcatc cctgctc     57

SEQ ID NO: 621         moltype = DNA  length = 60
FEATURE                Location/Qualifiers
source                 1..60
                       mol_type = other DNA
                       organism = synthetic construct
SEQUENCE: 621
gtgactggag ttcagacgtg tgctcttccg atctcaaaga ggactttcgc tatcgatctc  60

SEQ ID NO: 622         moltype = DNA  length = 54
FEATURE                Location/Qualifiers
source                 1..54
                       mol_type = other DNA
                       organism = synthetic construct
SEQUENCE: 622
gtgactggag ttcagacgtg tgctcttccg atctcggagg tcatactgca tcag        54

SEQ ID NO: 623         moltype = DNA  length = 55
FEATURE                Location/Qualifiers
source                 1..55
                       mol_type = other DNA
                       organism = synthetic construct
SEQUENCE: 623
gtgactggag ttcagacgtg tgctcttccg atctgatggc ctgggggtcc tctgg       55

SEQ ID NO: 624         moltype = DNA  length = 55
FEATURE                Location/Qualifiers
source                 1..55
                       mol_type = other DNA
                       organism = synthetic construct
SEQUENCE: 624
gtgactggag ttcagacgtg tgctcttccg atctccgcct gaagagcacg ccatg       55

SEQ ID NO: 625         moltype = DNA  length = 60
FEATURE                Location/Qualifiers
source                 1..60
                       mol_type = other DNA
                       organism = synthetic construct
```

```
SEQUENCE: 625
gtgactggag ttcagacgtg tgctcttccg atctgcaact gatagacgta atcccaaagc  60

SEQ ID NO: 626          moltype = DNA  length = 56
FEATURE                 Location/Qualifiers
source                  1..56
                        mol_type = other DNA
                        organism = synthetic construct
SEQUENCE: 626
gtgactggag ttcagacgtg tgctcttccg atctgatccc aacggactgg ctcgac      56

SEQ ID NO: 627          moltype = DNA  length = 58
FEATURE                 Location/Qualifiers
source                  1..58
                        mol_type = other DNA
                        organism = synthetic construct
SEQUENCE: 627
gtgactggag ttcagacgtg tgctcttccg atctctggac attttctcat aggtcatg    58

SEQ ID NO: 628          moltype = DNA  length = 60
FEATURE                 Location/Qualifiers
source                  1..60
                        mol_type = other DNA
                        organism = synthetic construct
SEQUENCE: 628
gtgactggag ttcagacgtg tgctcttccg atctctctca tttacataat ctgctctgtc  60

SEQ ID NO: 629          moltype = DNA  length = 57
FEATURE                 Location/Qualifiers
source                  1..57
                        mol_type = other DNA
                        organism = synthetic construct
SEQUENCE: 629
gtgactggag ttcagacgtg tgctcttccg atctggccag aaggaaccat cgggaac     57

SEQ ID NO: 630          moltype = DNA  length = 60
FEATURE                 Location/Qualifiers
source                  1..60
                        mol_type = other DNA
                        organism = synthetic construct
SEQUENCE: 630
gtgactggag ttcagacgtg tgctcttccg atctttcagc agaaagagga ctcagaatag  60

SEQ ID NO: 631          moltype = DNA  length = 56
FEATURE                 Location/Qualifiers
source                  1..56
                        mol_type = other DNA
                        organism = synthetic construct
SEQUENCE: 631
gtgactggag ttcagacgtg tgctcttccg atctctacct tatatccctt ctcacc      56

SEQ ID NO: 632          moltype = DNA  length = 54
FEATURE                 Location/Qualifiers
source                  1..54
                        mol_type = other DNA
                        organism = synthetic construct
SEQUENCE: 632
gtgactggag ttcagacgtg tgctcttccg atctaggtag tccagggtat gtgg        54

SEQ ID NO: 633          moltype = DNA  length = 57
FEATURE                 Location/Qualifiers
source                  1..57
                        mol_type = other DNA
                        organism = synthetic construct
SEQUENCE: 633
gtgactggag ttcagacgtg tgctcttccg atctccccat ccattcttcc tattccc     57

SEQ ID NO: 634          moltype = DNA  length = 54
FEATURE                 Location/Qualifiers
source                  1..54
                        mol_type = other DNA
                        organism = synthetic construct
SEQUENCE: 634
gtgactggag ttcagacgtg tgctcttccg atctcccaac cctccaccac cttc        54

SEQ ID NO: 635          moltype = DNA  length = 55
FEATURE                 Location/Qualifiers
source                  1..55
                        mol_type = other DNA
```

```
                        organism = synthetic construct
SEQUENCE: 635
gtgactggag ttcagacgtg tgctcttccg atctacgaac tgtgctgatg ggaag       55

SEQ ID NO: 636          moltype = DNA  length = 60
FEATURE                 Location/Qualifiers
source                  1..60
                        mol_type = other DNA
                        organism = synthetic construct
SEQUENCE: 636
gtgactggag ttcagacgtg tgctcttccg atctggtgcc tatgggacag tgtacaaggc  60

SEQ ID NO: 637          moltype = DNA  length = 55
FEATURE                 Location/Qualifiers
source                  1..55
                        mol_type = other DNA
                        organism = synthetic construct
SEQUENCE: 637
gtgactggag ttcagacgtg tgctcttccg atctggtgat aggagtctgt gattg       55

SEQ ID NO: 638          moltype = DNA  length = 58
FEATURE                 Location/Qualifiers
source                  1..58
                        mol_type = other DNA
                        organism = synthetic construct
SEQUENCE: 638
gtgactggag ttcagacgtg tgctcttccg atctcccttg cctcccttc caatggac     58

SEQ ID NO: 639          moltype = DNA  length = 60
FEATURE                 Location/Qualifiers
source                  1..60
                        mol_type = other DNA
                        organism = synthetic construct
SEQUENCE: 639
gtgactggag ttcagacgtg tgctcttccg atctacaagg gagcagcaga ctttgtggtc  60

SEQ ID NO: 640          moltype = DNA  length = 60
FEATURE                 Location/Qualifiers
source                  1..60
                        mol_type = other DNA
                        organism = synthetic construct
SEQUENCE: 640
gtgactggag ttcagacgtg tgctcttccg atctgtctct gagtccacta aaagttgtgc  60

SEQ ID NO: 641          moltype = DNA  length = 54
FEATURE                 Location/Qualifiers
source                  1..54
                        mol_type = other DNA
                        organism = synthetic construct
SEQUENCE: 641
gtgactggag ttcagacgtg tgctcttccg atctagcgta tccaagaggc ctag        54

SEQ ID NO: 642          moltype = DNA  length = 56
FEATURE                 Location/Qualifiers
source                  1..56
                        mol_type = other DNA
                        organism = synthetic construct
SEQUENCE: 642
gtgactggag ttcagacgtg tgctcttccg atctgtggcc atctggatgc gtgcac      56

SEQ ID NO: 643          moltype = DNA  length = 55
FEATURE                 Location/Qualifiers
source                  1..55
                        mol_type = other DNA
                        organism = synthetic construct
SEQUENCE: 643
gtgactggag ttcagacgtg tgctcttccg atctttagaa tcatcctggc ttctg       55

SEQ ID NO: 644          moltype = DNA  length = 56
FEATURE                 Location/Qualifiers
source                  1..56
                        mol_type = other DNA
                        organism = synthetic construct
SEQUENCE: 644
gtgactggag ttcagacgtg tgctcttccg atctccatcc caggagctta cttccc      56

SEQ ID NO: 645          moltype = DNA  length = 57
FEATURE                 Location/Qualifiers
source                  1..57
```

```
                        mol_type = other DNA
                        organism = synthetic construct
SEQUENCE: 645
gtgactggag ttcagacgtg tgctcttccg atctttggct ttatgcttat tttgtcc     57

SEQ ID NO: 646          moltype = DNA  length = 58
FEATURE                 Location/Qualifiers
source                  1..58
                        mol_type = other DNA
                        organism = synthetic construct
SEQUENCE: 646
gtgactggag ttcagacgtg tgctcttccg atctacacaa cacaaaatag ccgtataa    58

SEQ ID NO: 647          moltype = DNA  length = 57
FEATURE                 Location/Qualifiers
source                  1..57
                        mol_type = other DNA
                        organism = synthetic construct
SEQUENCE: 647
gtgactggag ttcagacgtg tgctcttccg atctcatcac agtaaataac actctgg     57

SEQ ID NO: 648          moltype = DNA  length = 57
FEATURE                 Location/Qualifiers
source                  1..57
                        mol_type = other DNA
                        organism = synthetic construct
SEQUENCE: 648
gtgactggag ttcagacgtg tgctcttccg atctccccca aatctgaatc ccgagag     57

SEQ ID NO: 649          moltype = DNA  length = 55
FEATURE                 Location/Qualifiers
source                  1..55
                        mol_type = other DNA
                        organism = synthetic construct
SEQUENCE: 649
gtgactggag ttcagacgtg tgctcttccg atctctctca ccacccgcac gtctg       55

SEQ ID NO: 650          moltype = DNA  length = 57
FEATURE                 Location/Qualifiers
source                  1..57
                        mol_type = other DNA
                        organism = synthetic construct
SEQUENCE: 650
gtgactggag ttcagacgtg tgctcttccg atctccaggt cagtggatcc cctctcc     57

SEQ ID NO: 651          moltype = DNA  length = 54
FEATURE                 Location/Qualifiers
source                  1..54
                        mol_type = other DNA
                        organism = synthetic construct
SEQUENCE: 651
gtgactggag ttcagacgtg tgctcttccg atctttgaaa gatggcggct gcag        54

SEQ ID NO: 652          moltype = DNA  length = 54
FEATURE                 Location/Qualifiers
source                  1..54
                        mol_type = other DNA
                        organism = synthetic construct
SEQUENCE: 652
gtgactggag ttcagacgtg tgctcttccg atctggccaa cttgttcagt ggag        54

SEQ ID NO: 653          moltype = DNA  length = 55
FEATURE                 Location/Qualifiers
source                  1..55
                        mol_type = other DNA
                        organism = synthetic construct
SEQUENCE: 653
gtgactggag ttcagacgtg tgctcttccg atctgtcatc tctcctccct gcttc       55

SEQ ID NO: 654          moltype = DNA  length = 54
FEATURE                 Location/Qualifiers
source                  1..54
                        mol_type = other DNA
                        organism = synthetic construct
SEQUENCE: 654
gtgactggag ttcagacgtg tgctcttccg atctctttga ccatgaaggc agga        54

SEQ ID NO: 655          moltype = DNA  length = 60
FEATURE                 Location/Qualifiers
```

```
source                  1..60
                        mol_type = other DNA
                        organism = synthetic construct
SEQUENCE: 655
gtgactggag ttcagacgtg tgctcttccg atctggtact gtgtatatac ttacttctcc  60

SEQ ID NO: 656          moltype = DNA  length = 60
FEATURE                 Location/Qualifiers
source                  1..60
                        mol_type = other DNA
                        organism = synthetic construct
SEQUENCE: 656
gtgactggag ttcagacgtg tgctcttccg atctggcatt ttgagtgtta gactggaaac  60

SEQ ID NO: 657          moltype = DNA  length = 60
FEATURE                 Location/Qualifiers
source                  1..60
                        mol_type = other DNA
                        organism = synthetic construct
SEQUENCE: 657
gtgactggag ttcagacgtg tgctcttccg atctattcac ttttatcacc tttccttgcc  60

SEQ ID NO: 658          moltype = DNA  length = 54
FEATURE                 Location/Qualifiers
source                  1..54
                        mol_type = other DNA
                        organism = synthetic construct
SEQUENCE: 658
gtgactggag ttcagacgtg tgctcttccg atctccgctt cttgtcctgc ttgc        54

SEQ ID NO: 659          moltype = DNA  length = 60
FEATURE                 Location/Qualifiers
source                  1..60
                        mol_type = other DNA
                        organism = synthetic construct
SEQUENCE: 659
gtgactggag ttcagacgtg tgctcttccg atcttgcctc ttgcttctct tttcctatcc  60

SEQ ID NO: 660          moltype = DNA  length = 54
FEATURE                 Location/Qualifiers
source                  1..54
                        mol_type = other DNA
                        organism = synthetic construct
SEQUENCE: 660
gtgactggag ttcagacgtg tgctcttccg atctgcccag gggtcagagg caag        54

SEQ ID NO: 661          moltype = DNA  length = 58
FEATURE                 Location/Qualifiers
source                  1..58
                        mol_type = other DNA
                        organism = synthetic construct
SEQUENCE: 661
gtgactggag ttcagacgtg tgctcttccg atctgcctca tcttgggcct gtgttatc    58

SEQ ID NO: 662          moltype = DNA  length = 54
FEATURE                 Location/Qualifiers
source                  1..54
                        mol_type = other DNA
                        organism = synthetic construct
SEQUENCE: 662
gtgactggag ttcagacgtg tgctcttccg atctctccca gagaccccag ttgc        54

SEQ ID NO: 663          moltype = DNA  length = 55
FEATURE                 Location/Qualifiers
source                  1..55
                        mol_type = other DNA
                        organism = synthetic construct
SEQUENCE: 663
gtgactggag ttcagacgtg tgctcttccg atctcccagg cctctgattc ctcac       55

SEQ ID NO: 664          moltype = DNA  length = 55
FEATURE                 Location/Qualifiers
source                  1..55
                        mol_type = other DNA
                        organism = synthetic construct
SEQUENCE: 664
gtgactggag ttcagacgtg tgctcttccg atcttgtcgt ctctccagcc ccagc       55

SEQ ID NO: 665          moltype = DNA  length = 59
```

```
FEATURE                Location/Qualifiers
source                 1..59
                       mol_type = other DNA
                       organism = synthetic construct
SEQUENCE: 665
gtgactggag ttcagacgtg tgctcttccg atctgacttt caactctgtc tccttcctc   59

SEQ ID NO: 666         moltype = DNA  length = 54
FEATURE                Location/Qualifiers
source                 1..54
                       mol_type = other DNA
                       organism = synthetic construct
SEQUENCE: 666
gtgactggag ttcagacgtg tgctcttccg atctcaggca ttgaagtctc atgg        54

SEQ ID NO: 667         moltype = DNA  length = 57
FEATURE                Location/Qualifiers
source                 1..57
                       mol_type = other DNA
                       organism = synthetic construct
SEQUENCE: 667
gtgactggag ttcagacgtg tgctcttccg atcttctggg aagggacaga agatgac     57

SEQ ID NO: 668         moltype = DNA  length = 54
FEATURE                Location/Qualifiers
source                 1..54
                       mol_type = other DNA
                       organism = synthetic construct
SEQUENCE: 668
gtgactggag ttcagacgtg tgctcttccg atctagctcc cagaatgcca gagg        54

SEQ ID NO: 669         moltype = DNA  length = 55
FEATURE                Location/Qualifiers
source                 1..55
                       mol_type = other DNA
                       organism = synthetic construct
SEQUENCE: 669
gtgactggag ttcagacgtg tgctcttccg atcttgactg ctcttttcac ccatc       55

SEQ ID NO: 670         moltype = DNA  length = 54
FEATURE                Location/Qualifiers
source                 1..54
                       mol_type = other DNA
                       organism = synthetic construct
SEQUENCE: 670
gtgactggag ttcagacgtg tgctcttccg atctccccag cccaaccctt gtcc        54

SEQ ID NO: 671         moltype = DNA  length = 55
FEATURE                Location/Qualifiers
source                 1..55
                       mol_type = other DNA
                       organism = synthetic construct
SEQUENCE: 671
gtgactggag ttcagacgtg tgctcttccg atctaattcc atgggactga ctttc       55

SEQ ID NO: 672         moltype = DNA  length = 54
FEATURE                Location/Qualifiers
source                 1..54
                       mol_type = other DNA
                       organism = synthetic construct
SEQUENCE: 672
gtgactggag ttcagacgtg tgctcttccg atcttgctag gggctgggg ttgg         54

SEQ ID NO: 673         moltype = DNA  length = 55
FEATURE                Location/Qualifiers
source                 1..55
                       mol_type = other DNA
                       organism = synthetic construct
SEQUENCE: 673
gtgactggag ttcagacgtg tgctcttccg atctcatgct ggatccccac ttttc       55

SEQ ID NO: 674         moltype = DNA  length = 60
FEATURE                Location/Qualifiers
source                 1..60
                       mol_type = other DNA
                       organism = synthetic construct
SEQUENCE: 674
gtgactggag ttcagacgtg tgctcttccg atctgtgcaa gtgaaagcct tatatctttc  60
```

```
SEQ ID NO: 675          moltype = DNA  length = 58
FEATURE                 Location/Qualifiers
source                  1..58
                        mol_type = other DNA
                        organism = synthetic construct
SEQUENCE: 675
gtgactggag ttcagacgtg tgctcttccg atctacatgg gaaaacataa ccttgaat    58

SEQ ID NO: 676          moltype = DNA  length = 54
FEATURE                 Location/Qualifiers
source                  1..54
                        mol_type = other DNA
                        organism = synthetic construct
SEQUENCE: 676
gtgactggag ttcagacgtg tgctcttccg atctggctga gtcctggcgc tgtg        54

SEQ ID NO: 677          moltype = DNA  length = 55
FEATURE                 Location/Qualifiers
source                  1..55
                        mol_type = other DNA
                        organism = synthetic construct
SEQUENCE: 677
gtgactggag ttcagacgtg tgctcttccg atctccccaa cgctgcccct gctca       55

SEQ ID NO: 678          moltype = DNA  length = 59
FEATURE                 Location/Qualifiers
source                  1..59
                        mol_type = other DNA
                        organism = synthetic construct
SEQUENCE: 678
gtgactggag ttcagacgtg tgctcttccg atctggcttt ggtgagatcc attgacctc   59

SEQ ID NO: 679          moltype = DNA  length = 57
FEATURE                 Location/Qualifiers
source                  1..57
                        mol_type = other DNA
                        organism = synthetic construct
SEQUENCE: 679
gtgactggag ttcagacgtg tgctcttccg atcttgtcaa gaaaccatga tctctgt     57

SEQ ID NO: 680          moltype = DNA  length = 55
FEATURE                 Location/Qualifiers
source                  1..55
                        mol_type = other DNA
                        organism = synthetic construct
SEQUENCE: 680
gtgactggag ttcagacgtg tgctcttccg atcttaacca gctgtcctcc tcccc       55

SEQ ID NO: 681          moltype = DNA  length = 54
FEATURE                 Location/Qualifiers
source                  1..54
                        mol_type = other DNA
                        organism = synthetic construct
SEQUENCE: 681
gtgactggag ttcagacgtg tgctcttccg atctaacaac acagaagcaa agcg        54

SEQ ID NO: 682          moltype = DNA  length = 60
FEATURE                 Location/Qualifiers
source                  1..60
                        mol_type = other DNA
                        organism = synthetic construct
SEQUENCE: 682
gtgactggag ttcagacgtg tgctcttccg atctgaacca agttcttccg agggaattcc  60

SEQ ID NO: 683          moltype = DNA  length = 55
FEATURE                 Location/Qualifiers
source                  1..55
                        mol_type = other DNA
                        organism = synthetic construct
SEQUENCE: 683
gtgactggag ttcagacgtg tgctcttccg atctggaaat ccttccgggc agcca       55

SEQ ID NO: 684          moltype = DNA  length = 59
FEATURE                 Location/Qualifiers
source                  1..59
                        mol_type = other DNA
                        organism = synthetic construct
SEQUENCE: 684
gtgactggag ttcagacgtg tgctcttccg atctaaatat ggtcgacggt ccaaatttg   59
```

```
SEQ ID NO: 685          moltype = DNA  length = 54
FEATURE                 Location/Qualifiers
source                  1..54
                        mol_type = other DNA
                        organism = synthetic construct
SEQUENCE: 685
gtgactggag ttcagacgtg tgctcttccg atctggacac aactgccaca agcc        54

SEQ ID NO: 686          moltype = DNA  length = 57
FEATURE                 Location/Qualifiers
source                  1..57
                        mol_type = other DNA
                        organism = synthetic construct
SEQUENCE: 686
gtgactggag ttcagacgtg tgctcttccg atctcctcag cccgaccaag gacaaga     57

SEQ ID NO: 687          moltype = DNA  length = 54
FEATURE                 Location/Qualifiers
source                  1..54
                        mol_type = other DNA
                        organism = synthetic construct
SEQUENCE: 687
gtgactggag ttcagacgtg tgctcttccg atcttctgcc tcatgctctc tcca        54

SEQ ID NO: 688          moltype = DNA  length = 54
FEATURE                 Location/Qualifiers
source                  1..54
                        mol_type = other DNA
                        organism = synthetic construct
SEQUENCE: 688
gtgactggag ttcagacgtg tgctcttccg atcttcaagt gggctgaaaa tgag        54

SEQ ID NO: 689          moltype = DNA  length = 58
FEATURE                 Location/Qualifiers
source                  1..58
                        mol_type = other DNA
                        organism = synthetic construct
SEQUENCE: 689
gtgactggag ttcagacgtg tgctcttccg atctgcagca ggagagcttt gccattca    58

SEQ ID NO: 690          moltype = DNA  length = 54
FEATURE                 Location/Qualifiers
source                  1..54
                        mol_type = other DNA
                        organism = synthetic construct
SEQUENCE: 690
gtgactggag ttcagacgtg tgctcttccg atctcatatg ccaagagtcc agac        54

SEQ ID NO: 691          moltype = DNA  length = 54
FEATURE                 Location/Qualifiers
source                  1..54
                        mol_type = other DNA
                        organism = synthetic construct
SEQUENCE: 691
gtgactggag ttcagacgtg tgctcttccg atcttgaggg cctccttctc atca        54

SEQ ID NO: 692          moltype = DNA  length = 55
FEATURE                 Location/Qualifiers
source                  1..55
                        mol_type = other DNA
                        organism = synthetic construct
SEQUENCE: 692
gtgactggag ttcagacgtg tgctcttccg atctgcctcc accaccttcc caaag       55

SEQ ID NO: 693          moltype = DNA  length = 60
FEATURE                 Location/Qualifiers
source                  1..60
                        mol_type = other DNA
                        organism = synthetic construct
SEQUENCE: 693
gtgactggag ttcagacgtg tgctcttccg atctctctcg atgatcttcc agcggacctg  60

SEQ ID NO: 694          moltype = DNA  length = 54
FEATURE                 Location/Qualifiers
source                  1..54
                        mol_type = other DNA
                        organism = synthetic construct
SEQUENCE: 694
```

```
gtgactggag ttcagacgtg tgctcttccg atctacatgc aggcgaccac cact        54

SEQ ID NO: 695          moltype = DNA  length = 57
FEATURE                 Location/Qualifiers
source                  1..57
                        mol_type = other DNA
                        organism = synthetic construct
SEQUENCE: 695
gtgactggag ttcagacgtg tgctcttccg atctcttgtg gaagggctcc tggctca     57

SEQ ID NO: 696          moltype = DNA  length = 55
FEATURE                 Location/Qualifiers
source                  1..55
                        mol_type = other DNA
                        organism = synthetic construct
SEQUENCE: 696
gtgactggag ttcagacgtg tgctcttccg atctgccgtt gatgaatgtc catat       55

SEQ ID NO: 697          moltype = DNA  length = 54
FEATURE                 Location/Qualifiers
source                  1..54
                        mol_type = other DNA
                        organism = synthetic construct
SEQUENCE: 697
gtgactggag ttcagacgtg tgctcttccg atctgatcca gaggaggaag tcag        54

SEQ ID NO: 698          moltype = DNA  length = 55
FEATURE                 Location/Qualifiers
source                  1..55
                        mol_type = other DNA
                        organism = synthetic construct
SEQUENCE: 698
gtgactggag ttcagacgtg tgctcttccg atctcctctc ccaggggttt gccta       55

SEQ ID NO: 699          moltype = DNA  length = 54
FEATURE                 Location/Qualifiers
source                  1..54
                        mol_type = other DNA
                        organism = synthetic construct
SEQUENCE: 699
gtgactggag ttcagacgtg tgctcttccg atctttgcag gatgggccgg tgag        54

SEQ ID NO: 700          moltype = DNA  length = 55
FEATURE                 Location/Qualifiers
source                  1..55
                        mol_type = other DNA
                        organism = synthetic construct
SEQUENCE: 700
gtgactggag ttcagacgtg tgctcttccg atctgtccat tatgatgctc caggt       55

SEQ ID NO: 701          moltype = DNA  length = 60
FEATURE                 Location/Qualifiers
source                  1..60
                        mol_type = other DNA
                        organism = synthetic construct
SEQUENCE: 701
gtgactggag ttcagacgtg tgctcttccg atctatcttt tctggggatg tccaatatgg  60

SEQ ID NO: 702          moltype = DNA  length = 59
FEATURE                 Location/Qualifiers
source                  1..59
                        mol_type = other DNA
                        organism = synthetic construct
SEQUENCE: 702
gtgactggag ttcagacgtg tgctcttccg atctctctga agaggagtca tcatcatca   59

SEQ ID NO: 703          moltype = DNA  length = 54
FEATURE                 Location/Qualifiers
source                  1..54
                        mol_type = other DNA
                        organism = synthetic construct
SEQUENCE: 703
gtgactggag ttcagacgtg tgctcttccg atctccactt ccacaggggc tccc        54

SEQ ID NO: 704          moltype = DNA  length = 54
FEATURE                 Location/Qualifiers
source                  1..54
                        mol_type = other DNA
                        organism = synthetic construct
```

```
SEQUENCE: 704
gtgactggag ttcagacgtg tgctcttccg atctacgagt gcttcatcaa ggtg       54

SEQ ID NO: 705          moltype = DNA  length = 55
FEATURE                 Location/Qualifiers
source                  1..55
                        mol_type = other DNA
                        organism = synthetic construct
SEQUENCE: 705
gtgactggag ttcagacgtg tgctcttccg atctgagttg ttgaggaagc cagac      55

SEQ ID NO: 706          moltype = DNA  length = 54
FEATURE                 Location/Qualifiers
source                  1..54
                        mol_type = other DNA
                        organism = synthetic construct
SEQUENCE: 706
gtgactggag ttcagacgtg tgctcttccg atctcccact gtgttactgc catc       54

SEQ ID NO: 707          moltype = DNA  length = 60
FEATURE                 Location/Qualifiers
source                  1..60
                        mol_type = other DNA
                        organism = synthetic construct
SEQUENCE: 707
gtgactggag ttcagacgtg tgctcttccg atcttgttct ggcggtgttt tgaaattagt  60

SEQ ID NO: 708          moltype = DNA  length = 57
FEATURE                 Location/Qualifiers
source                  1..57
                        mol_type = other DNA
                        organism = synthetic construct
SEQUENCE: 708
gtgactggag ttcagacgtg tgctcttccg atctgcatca aagcagagga caagatc     57

SEQ ID NO: 709          moltype = DNA  length = 60
FEATURE                 Location/Qualifiers
source                  1..60
                        mol_type = other DNA
                        organism = synthetic construct
SEQUENCE: 709
gtgactggag ttcagacgtg tgctcttccg atctgcttct tggtcgtgtt cttcattcgg  60

SEQ ID NO: 710          moltype = DNA  length = 59
FEATURE                 Location/Qualifiers
source                  1..59
                        mol_type = other DNA
                        organism = synthetic construct
SEQUENCE: 710
gtgactggag ttcagacgtg tgctcttccg atctgcatag gggtcttctt aatcgcctg   59

SEQ ID NO: 711          moltype = DNA  length = 60
FEATURE                 Location/Qualifiers
source                  1..60
                        mol_type = other DNA
                        organism = synthetic construct
SEQUENCE: 711
gtgactggag ttcagacgtg tgctcttccg atctggcctg cttatctgtt cctcctcctg  60

SEQ ID NO: 712          moltype = DNA  length = 60
FEATURE                 Location/Qualifiers
source                  1..60
                        mol_type = other DNA
                        organism = synthetic construct
SEQUENCE: 712
gtgactggag ttcagacgtg tgctcttccg atctgatgtg ctgggtcctt ttcagttgcg  60

SEQ ID NO: 713          moltype = DNA  length = 58
FEATURE                 Location/Qualifiers
source                  1..58
                        mol_type = other DNA
                        organism = synthetic construct
SEQUENCE: 713
gtgactggag ttcagacgtg tgctcttccg atctaacgag aagcacatca acctgagc    58

SEQ ID NO: 714          moltype = DNA  length = 60
FEATURE                 Location/Qualifiers
source                  1..60
                        mol_type = other DNA
```

```
                        organism = synthetic construct
SEQUENCE: 714
gtgactggag ttcagacgtg tgctcttccg atctaaacca aacaacttcc acctctaaag  60

SEQ ID NO: 715          moltype = DNA  length = 60
FEATURE                 Location/Qualifiers
source                  1..60
                        mol_type = other DNA
                        organism = synthetic construct
SEQUENCE: 715
gtgactggag ttcagacgtg tgctcttccg atctcggaag agatgtctaa tattaacttg  60

SEQ ID NO: 716          moltype = DNA  length = 56
FEATURE                 Location/Qualifiers
source                  1..56
                        mol_type = other DNA
                        organism = synthetic construct
SEQUENCE: 716
gtgactggag ttcagacgtg tgctcttccg atctaggaaa cacaattagc ctggac      56

SEQ ID NO: 717          moltype = DNA  length = 55
FEATURE                 Location/Qualifiers
source                  1..55
                        mol_type = other DNA
                        organism = synthetic construct
SEQUENCE: 717
gtgactggag ttcagacgtg tgctcttccg atctgagctc caaaccaagt gttag       55

SEQ ID NO: 718          moltype = DNA  length = 60
FEATURE                 Location/Qualifiers
source                  1..60
                        mol_type = other DNA
                        organism = synthetic construct
SEQUENCE: 718
gtgactggag ttcagacgtg tgctcttccg atctgagggg tgcagcattg gtgaacattc  60

SEQ ID NO: 719          moltype = DNA  length = 59
FEATURE                 Location/Qualifiers
source                  1..59
                        mol_type = other DNA
                        organism = synthetic construct
SEQUENCE: 719
gtgactggag ttcagacgtg tgctcttccg atctcacatt ctaaagtgtt caaattcct   59

SEQ ID NO: 720          moltype = DNA  length = 59
FEATURE                 Location/Qualifiers
source                  1..59
                        mol_type = other DNA
                        organism = synthetic construct
SEQUENCE: 720
gtgactggag ttcagacgtg tgctcttccg atctacctcc atgtgggttt ataaatgtg   59

SEQ ID NO: 721          moltype = DNA  length = 57
FEATURE                 Location/Qualifiers
source                  1..57
                        mol_type = other DNA
                        organism = synthetic construct
SEQUENCE: 721
gtgactggag ttcagacgtg tgctcttccg atctggggaa ctgtaacgct gcctatc     57

SEQ ID NO: 722          moltype = DNA  length = 56
FEATURE                 Location/Qualifiers
source                  1..56
                        mol_type = other DNA
                        organism = synthetic construct
SEQUENCE: 722
gtgactggag ttcagacgtg tgctcttccg atctagcctc ttcaccccgt ctgctg      56

SEQ ID NO: 723          moltype = DNA  length = 53
FEATURE                 Location/Qualifiers
source                  1..53
                        mol_type = other DNA
                        organism = synthetic construct
SEQUENCE: 723
gtgactggag ttcagacgtg tgctcttccg atctcaccct aacggcccgt gca         53

SEQ ID NO: 724          moltype = DNA  length = 55
FEATURE                 Location/Qualifiers
source                  1..55
```

```
                         mol_type = other DNA
                         organism = synthetic construct
SEQUENCE: 724
gtgactggag ttcagacgtg tgctcttccg atctctctcc acgctccctc cactc       55

SEQ ID NO: 725           moltype = DNA  length = 57
FEATURE                  Location/Qualifiers
source                   1..57
                         mol_type = other DNA
                         organism = synthetic construct
SEQUENCE: 725
gtgactggag ttcagacgtg tgctcttccg atctcctgag agtggagctg gagagac     57

SEQ ID NO: 726           moltype = DNA  length = 54
FEATURE                  Location/Qualifiers
source                   1..54
                         mol_type = other DNA
                         organism = synthetic construct
SEQUENCE: 726
gtgactggag ttcagacgtg tgctcttccg atctgtgtcc tgaggcaccc aagc        54

SEQ ID NO: 727           moltype = DNA  length = 54
FEATURE                  Location/Qualifiers
source                   1..54
                         mol_type = other DNA
                         organism = synthetic construct
SEQUENCE: 727
gtgactggag ttcagacgtg tgctcttccg atctcccatc cagttctgcc ccat        54

SEQ ID NO: 728           moltype = DNA  length = 57
FEATURE                  Location/Qualifiers
source                   1..57
                         mol_type = other DNA
                         organism = synthetic construct
SEQUENCE: 728
gtgactggag ttcagacgtg tgctcttccg atctgaggac ctgtgggact ctgcact     57

SEQ ID NO: 729           moltype = DNA  length = 53
FEATURE                  Location/Qualifiers
source                   1..53
                         mol_type = other DNA
                         organism = synthetic construct
SEQUENCE: 729
gtgactggag ttcagacgtg tgctcttccg atctcagtga ccgccggcag gac         53

SEQ ID NO: 730           moltype = DNA  length = 59
FEATURE                  Location/Qualifiers
source                   1..59
                         mol_type = other DNA
                         organism = synthetic construct
SEQUENCE: 730
gtgactggag ttcagacgtg tgctcttccg atcttagctc cttgtcggtg gtgttagcg   59

SEQ ID NO: 731           moltype = DNA  length = 53
FEATURE                  Location/Qualifiers
source                   1..53
                         mol_type = other DNA
                         organism = synthetic construct
SEQUENCE: 731
gtgactggag ttcagacgtg tgctcttccg atcttcgtca gcctccacca gct         53

SEQ ID NO: 732           moltype = DNA  length = 56
FEATURE                  Location/Qualifiers
source                   1..56
                         mol_type = other DNA
                         organism = synthetic construct
SEQUENCE: 732
gtgactggag ttcagacgtg tgctcttccg atctgctcat ggacgcgttg gactcc      56

SEQ ID NO: 733           moltype = DNA  length = 56
FEATURE                  Location/Qualifiers
source                   1..56
                         mol_type = other DNA
                         organism = synthetic construct
SEQUENCE: 733
gtgactggag ttcagacgtg tgctcttccg atctgggacc caagctggac ttccca      56

SEQ ID NO: 734           moltype = DNA  length = 59
FEATURE                  Location/Qualifiers
```

```
source                  1..59
                        mol_type = other DNA
                        organism = synthetic construct
SEQUENCE: 734
gtgactggag ttcagacgtg tgctcttccg atctcaggac ctccacctct gagctattg   59

SEQ ID NO: 735          moltype = DNA  length = 60
FEATURE                 Location/Qualifiers
source                  1..60
                        mol_type = other DNA
                        organism = synthetic construct
SEQUENCE: 735
gtgactggag ttcagacgtg tgctcttccg atctagcccg acgcgtacag gatgatgtcc  60

SEQ ID NO: 736          moltype = DNA  length = 55
FEATURE                 Location/Qualifiers
source                  1..55
                        mol_type = other DNA
                        organism = synthetic construct
SEQUENCE: 736
gtgactggag ttcagacgtg tgctcttccg atctcttgcc ggaagagcct gactc       55

SEQ ID NO: 737          moltype = DNA  length = 54
FEATURE                 Location/Qualifiers
source                  1..54
                        mol_type = other DNA
                        organism = synthetic construct
SEQUENCE: 737
gtgactggag ttcagacgtg tgctcttccg atcttggagg cgctggacaa ggtc        54

SEQ ID NO: 738          moltype = DNA  length = 60
FEATURE                 Location/Qualifiers
source                  1..60
                        mol_type = other DNA
                        organism = synthetic construct
SEQUENCE: 738
gtgactggag ttcagacgtg tgctcttccg atctctttcc attctctgct ggatgacgtg  60

SEQ ID NO: 739          moltype = DNA  length = 59
FEATURE                 Location/Qualifiers
source                  1..59
                        mol_type = other DNA
                        organism = synthetic construct
SEQUENCE: 739
gtgactggag ttcagacgtg tgctcttccg atctgagtat gcctgccgtg tgaaccatg   59

SEQ ID NO: 740          moltype = DNA  length = 60
FEATURE                 Location/Qualifiers
source                  1..60
                        mol_type = other DNA
                        organism = synthetic construct
SEQUENCE: 740
gtgactggag ttcagacgtg tgctcttccg atctgccagt aggtcatgaa tataaagaca  60

SEQ ID NO: 741          moltype = DNA  length = 60
FEATURE                 Location/Qualifiers
source                  1..60
                        mol_type = other DNA
                        organism = synthetic construct
SEQUENCE: 741
gtgactggag ttcagacgtg tgctcttccg atctactcta ccacatatag gtccttggga  60

SEQ ID NO: 742          moltype = DNA  length = 60
FEATURE                 Location/Qualifiers
source                  1..60
                        mol_type = other DNA
                        organism = synthetic construct
SEQUENCE: 742
gtgactggag ttcagacgtg tgctcttccg atctgtgact ggatccacaa ccaaaattct  60

SEQ ID NO: 743          moltype = DNA  length = 55
FEATURE                 Location/Qualifiers
source                  1..55
                        mol_type = other DNA
                        organism = synthetic construct
SEQUENCE: 743
gtgactggag ttcagacgtg tgctcttccg atctcctgag gaaaaccata cagct       55

SEQ ID NO: 744          moltype = DNA  length = 59
```

```
FEATURE                 Location/Qualifiers
source                  1..59
                        mol_type = other DNA
                        organism = synthetic construct
SEQUENCE: 744
gtgactggag ttcagacgtg tgctcttccg atctatgcct tggtgtagca ctgacattc   59

SEQ ID NO: 745          moltype = DNA  length = 60
FEATURE                 Location/Qualifiers
source                  1..60
                        mol_type = other DNA
                        organism = synthetic construct
SEQUENCE: 745
gtgactggag ttcagacgtg tgctcttccg atctagtttg tatcttggat gccacatttt  60

SEQ ID NO: 746          moltype = DNA  length = 60
FEATURE                 Location/Qualifiers
source                  1..60
                        mol_type = other DNA
                        organism = synthetic construct
SEQUENCE: 746
gtgactggag ttcagacgtg tgctcttccg atctgcacca agtcttttgc catgatgcga  60

SEQ ID NO: 747          moltype = DNA  length = 54
FEATURE                 Location/Qualifiers
source                  1..54
                        mol_type = other DNA
                        organism = synthetic construct
SEQUENCE: 747
gtgactggag ttcagacgtg tgctcttccg atctgggtgt caccaaggcc atgg        54

SEQ ID NO: 748          moltype = DNA  length = 56
FEATURE                 Location/Qualifiers
source                  1..56
                        mol_type = other DNA
                        organism = synthetic construct
SEQUENCE: 748
gtgactggag ttcagacgtg tgctcttccg atctaccatg tagggtcttg aatgag      56

SEQ ID NO: 749          moltype = DNA  length = 58
FEATURE                 Location/Qualifiers
source                  1..58
                        mol_type = other DNA
                        organism = synthetic construct
SEQUENCE: 749
gtgactggag ttcagacgtg tgctcttccg atctattgag tgagccccaa gaatgacc    58

SEQ ID NO: 750          moltype = DNA  length = 60
FEATURE                 Location/Qualifiers
source                  1..60
                        mol_type = other DNA
                        organism = synthetic construct
SEQUENCE: 750
gtgactggag ttcagacgtg tgctcttccg atcttcacat cgtccccctt tttaggtaga  60

SEQ ID NO: 751          moltype = DNA  length = 57
FEATURE                 Location/Qualifiers
source                  1..57
                        mol_type = other DNA
                        organism = synthetic construct
SEQUENCE: 751
gtgactggag ttcagacgtg tgctcttccg atctccctcg cacaacaaag ggcttcc     57

SEQ ID NO: 752          moltype = DNA  length = 53
FEATURE                 Location/Qualifiers
source                  1..53
                        mol_type = other DNA
                        organism = synthetic construct
SEQUENCE: 752
gtgactggag ttcagacgtg tgctcttccg atctacgagc agggctgggg aga         53

SEQ ID NO: 753          moltype = DNA  length = 55
FEATURE                 Location/Qualifiers
source                  1..55
                        mol_type = other DNA
                        organism = synthetic construct
SEQUENCE: 753
gtgactggag ttcagacgtg tgctcttccg atctgtgggc tgtgggcact tctgc       55
```

-continued

```
SEQ ID NO: 754          moltype = DNA  length = 55
FEATURE                 Location/Qualifiers
source                  1..55
                        mol_type = other DNA
                        organism = synthetic construct
SEQUENCE: 754
gtgactggag ttcagacgtg tgctcttccg atctgaagga tgcccaggag gagca      55

SEQ ID NO: 755          moltype = DNA  length = 53
FEATURE                 Location/Qualifiers
source                  1..53
                        mol_type = other DNA
                        organism = synthetic construct
SEQUENCE: 755
gtgactggag ttcagacgtg tgctcttccg atcttgcagc gggggagtgt gta        53

SEQ ID NO: 756          moltype = DNA  length = 55
FEATURE                 Location/Qualifiers
source                  1..55
                        mol_type = other DNA
                        organism = synthetic construct
SEQUENCE: 756
gtgactggag ttcagacgtg tgctcttccg atctggtaca cggcagggtc agggt      55

SEQ ID NO: 757          moltype = DNA  length = 54
FEATURE                 Location/Qualifiers
source                  1..54
                        mol_type = other DNA
                        organism = synthetic construct
SEQUENCE: 757
gtgactggag ttcagacgtg tgctcttccg atctagcgac ctcgggtggg aaca       54

SEQ ID NO: 758          moltype = DNA  length = 59
FEATURE                 Location/Qualifiers
source                  1..59
                        mol_type = other DNA
                        organism = synthetic construct
SEQUENCE: 758
gtgactggag ttcagacgtg tgctcttccg atctcgatgt cccggcgctt gatgtggtg  59
```